United States Patent
Novas et al.

(10) Patent No.: US 11,007,166 B2
(45) Date of Patent: *May 18, 2021

(54) METHODS OF TREATING MULTIPLE SCLEROSIS

(71) Applicant: Biogen MA Inc., Cambridge, MA (US)

(72) Inventors: Mark Novas, Lexington, MA (US); Rui (Ray) Zhang, Sharon, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/936,398

(22) Filed: Jul. 22, 2020

(65) Prior Publication Data

US 2020/0345679 A1 Nov. 5, 2020

Related U.S. Application Data

(63) Continuation of application No. 15/527,252, filed as application No. PCT/US2015/060850 on Nov. 16, 2015.

(60) Provisional application No. 62/232,963, filed on Sep. 25, 2015, provisional application No. 62/140,255, filed on Mar. 30, 2015, provisional application No. 62/080,783, filed on Nov. 17, 2014.

(51) Int. Cl.
| | | |
|---|---|---|
| *A61K 31/225* | (2006.01) | |
| *G01N 33/49* | (2006.01) | |
| *A61K 47/54* | (2017.01) | |
| *A61P 25/00* | (2006.01) | |
| *A61K 9/00* | (2006.01) | |
| *A61K 9/28* | (2006.01) | |
| *A61K 9/48* | (2006.01) | |
| *G09B 19/00* | (2006.01) | |

(52) U.S. Cl.
CPC .......... *A61K 31/225* (2013.01); *A61K 9/0053* (2013.01); *A61K 9/28* (2013.01); *A61K 9/485* (2013.01); *A61K 9/4808* (2013.01); *A61K 9/4825* (2013.01); *A61K 9/4858* (2013.01); *A61K 9/4866* (2013.01); *A61K 47/542* (2017.08); *A61K 47/545* (2017.08); *G01N 33/492* (2013.01); *G09B 19/00* (2013.01); *A61P 25/00* (2018.01); *Y02A 50/30* (2018.01)

(58) Field of Classification Search
None
See application file for complete search history.

(56) References Cited

U.S. PATENT DOCUMENTS

| | | |
|---|---|---|
| 4,959,389 A | 9/1990 | Speiser et al. |
| 6,436,992 B1 | 8/2002 | Joshi et al. |
| 6,509,376 B1 | 1/2003 | Joshi et al. |
| 8,148,414 B2 | 4/2012 | Gangakhedkar et al. |
| 8,669,281 B1 | 3/2014 | Zeidan et al. |
| 9,326,947 B1 | 5/2016 | Dyakonov et al. |
| 9,326,965 B2 | 5/2016 | Dyakonov et al. |
| 9,511,043 B2 | 12/2016 | Dyakonov et al. |
| 9,517,209 B2 | 12/2016 | Dyakonov et al. |
| 9,566,259 B1 | 2/2017 | Vaughn et al. |
| 9,636,318 B2 | 5/2017 | Vaughn et al. |
| 9,636,319 B1 | 5/2017 | Vaughn et al. |
| 9,814,691 B2 | 11/2017 | Dyakonov et al. |
| 9,814,692 B2 | 11/2017 | Vaughn et al. |
| 9,820,960 B2 | 11/2017 | Dyakonov et al. |
| 9,820,961 B2 | 11/2017 | Vaughn et al. |
| 10,098,863 B2 | 10/2018 | Vaughn et al. |
| 10,391,160 B2 | 8/2019 | Viglietta |
| 2007/0207141 A1 | 9/2007 | Lieberburg |
| 2010/0048651 A1 | 2/2010 | Gangakhedkar et al. |
| 2010/0130607 A1 | 5/2010 | Gold |
| 2013/0216615 A1 | 8/2013 | Goldman et al. |
| 2014/0057918 A1 | 2/2014 | Wustrow et al. |
| 2014/0179778 A1 | 6/2014 | Mao et al. |
| 2014/0179779 A1 | 6/2014 | Chao |
| 2014/0322251 A1* | 10/2014 | Ruff .......................... C07K 7/06 424/185.1 |
| 2015/0038499 A1 | 2/2015 | Virsik |
| 2017/0000873 A1 | 1/2017 | Viglietta |
| 2017/0354630 A1 | 12/2017 | Novas et al. |

(Continued)

FOREIGN PATENT DOCUMENTS

| | | |
|---|---|---|
| CN | 103732062 A | 4/2014 |
| JP | 2009-528359 A | 8/2009 |

(Continued)

OTHER PUBLICATIONS

Tecfidera FDA Prescribing Information (Mar. 27, 2013).*

(Continued)

*Primary Examiner* — Bong-Sook Baek
(74) *Attorney, Agent, or Firm* — Choate, Hall & Stewart LLP; Brenda Herschbach Jarrell; Tracy L. Vrablik

(57) ABSTRACT

Provided herein are methods of treating multiple sclerosis with a fumarate, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing. The methods provided herein improve the safety of treatment by informing and monitoring patients undergoing treatment regarding progressive multifocal leukoencephalopathy, and/or by monitoring lymphocyte count.

16 Claims, 4 Drawing Sheets

(56) References Cited

U.S. PATENT DOCUMENTS

Figure 1:
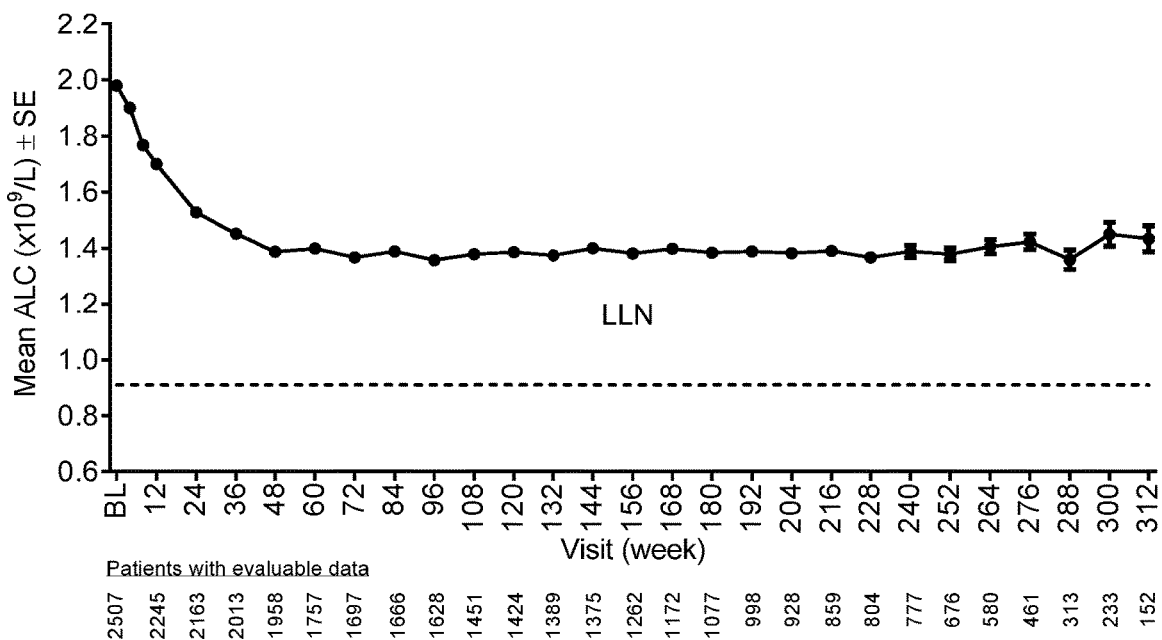

| | | |
|---|---|---|
| 2017/0368013 A1 | 12/2017 | Novas et al. |
| 2018/0000770 A1 | 1/2018 | Novas et al. |
| 2018/0055804 A1 | 3/2018 | Vaughn et al. |
| 2018/0055806 A1 | 3/2018 | Dyakonov et al. |
| 2018/0278918 A1 | 9/2018 | Peri |
| 2019/0008817 A1 | 1/2019 | Novas et al. |
| 2019/0125710 A1 | 5/2019 | Novas et al. |
| 2019/0247485 A1 | 8/2019 | Viglietta |

FOREIGN PATENT DOCUMENTS

| | | |
|---|---|---|
| WO | WO-2006/037342 A2 | 4/2006 |
| WO | WO-2007/100770 A2 | 9/2007 |
| WO | WO-2011/085369 A1 | 7/2011 |
| WO | WO-2012/162669 A1 | 11/2012 |
| WO | WO-2012/166971 A2 | 12/2012 |
| WO | WO-2013/119677 A1 | 8/2013 |
| WO | WO-2014/096425 A2 | 6/2014 |
| WO | WO-2015/130998 A1 | 9/2015 |
| WO | WO-2015/138917 A1 | 9/2015 |
| WO | WO-2016/057133 A1 | 4/2016 |
| WO | WO-2016/081355 A1 | 5/2016 |
| WO | WO-2017/040272 A1 | 3/2017 |
| WO | WO-2017/151184 A1 | 9/2017 |

OTHER PUBLICATIONS

Assessment Report Tecifdera®, published by the European Medicines Agency, Nov. 26, 2013.
Babij, R. et al., Comparative efficacy of alemtuzumab and established treatment in the management of multiple sclerosis, Neuropsychiatric Disease and Treatment 11:1221-1229 (2015).
Bartsch, T. et al., Progressive Neurologic Dysfunction in a Psoriasis Patient Treated With Dimethyl Fumarate, Ann. Neurol., 78(4): 501-514 (2015).
Bellizzi, A. et al., New Insights on Human Polyomavims JC and Pathogenesis of Progressive Multifocal Leukoencephalopathy, Clinical and Developmental Immunology, 2013:1-17 (2013).
Berger, J. R. et al., Progressive multifocal leukoencephalopathy in patients with HIV infection, J. NeuroVirology, 4:59-68 (1998).
Berger, J. R. et al., Predictive Factors for Prolonged Survival in Acquired Immunodeficiency Syndrome—Associated Progressive Multifocal Lenkoencephalopathy, Ann. Neural., 44(3):341-349 (1998).
Berger, J. R., The clinical features of PML, Cleveland Clinic Journal of Medicine, 78(2): S8-S12 (2011).
BG 12 BG 00012, BG 12/Oral Fumarate, FAG-201, Second-Generation Fumarate Derivative—Fumapharm/Biogen Idec, Drugs in R&D 6(4):229-230 (2005).
Bharat, A. et al., Incidence and Risk Factors for Progressive Multifocal Leukoencephalopathy among Patients with Selected Rheumatic Diseases, Arthritis Care Res (Hoboken) 64(4):612-615 (2012).
Bloomgren, G. et al., Risk of natalizumab-associated progressive multifocal leukoencephalopathy, N. Engl. J. Med., 366:1870-1880 (2012).
Brass, D. et al., Investigating an incidental finding of lymphopenia, BMJ, 348:gl 721 (2014).
Campath (alemtuzumab), Highlights of Prescribing Information, Full Prescribing Information, Injection for intravenous use, Genzvme Corporation, Revised Sep. 2014.
Carson, K. R. et al.., Monoclonal antibody-associated progressive multifocal leukoencephalopathy in patients treated with rituximab, natalizumab, and efalizumab: a Review from the Research on Adverse Drug Events and Reports (RADAR) Project, Lancet Oncology, 10:816-824 (2009).
Castelino, D. J., Lymphocytopenia in a hospital population—what does it signify, Aust. NZ J. Med., 27:170-174 (1997).
Cellcept (mycophenolate mofetil) Medication Guide, Genentech USA, Inc., Revised Sep. 2013.

Center for Drug Evaluation and Research: "Application No. 2040630rigls000: Medical Review(s)". Mar. 2013 [retrieved Feb. 15, 2019]. Retrieved from the internet <URL: https://www.accessdata.fda.gov/drugsatfda_docs/nda/2013/2040630rigls000MedR.pdf>.
Center for Drug Evaluation and Research: "Approval Package for Application No. NDA 204063/S10 [Tecfidera]". Dec. 2014 [retrieved Feb. 12, 2019]. Retrieved from the internet <URL: https://www.accessdata.fda.gov/dmgsatfdadocs/nda/2014/2040630rigls010.pdf>.
Chaves, C. et al., Lymphocyte subtypes in relapsing-remitting multiple sclerosis patients treated with dimethyl fumarate, MSJ—Exoerimental Translation and Clinical (2017).
Clifford, D. B. et al., A Study of Mefloquine Treatment for Progressive Multifocal Lenkoencephalopathy: Results and Exploration of Predictors of PML Outcomes, J. Neurovirol., 19:351-358 (2013).
Collazos, J., Opportunistic Infections of the CNS in Patients With AIDS: Diagnosis and Management, CNS Drugs, 17(12):869-887 (2003).
Cordiali-Fei, P. et al., Immunogenic Biomarkers for Clinical and therapeutic Management of Psoriasis, Mediators of Inflanunation, 2014:1-11 (2014).
Dammeier, N. et al., Case report of a patient with progressive multifocal leukoencephalopathy under treatment with dimethyl fumarate, BMC Neurology, 15:108 (2015).
De Jong, E. et al., The Course of Psoriasis, Clinics in Dermatology, 15:687-692 (1997).
De Raedt, S. et al., Progressive multifocal leukoencephalopathy as first manifestation of sarcoidosis, Clin. Neural. Neurosur., 110:186-189 (2008).
Declaration of Jacobus C. Rasser dated Mar. 4, 2013, submitted in the Opposition against European Patent No. EP 2316430 (including Annexes 1-7), 14 pages.
Dimethyl Fumarate (TECFIDERA) and PML Resulting in Death, National PBM Bulletin, Nov. 7, 2014 [retrieved on Jun. 16, 2017]. Retrieved from the Internet <URL:https://www.pbm.va.gov/PBM/vacenterformedicationsafety/nationalpbmbulletin/Dimethyl_Fumarate_T_cfidera_and_PML_Resulting_in_Death_NATIONAL_PBM_Bulletin.pdf>.
Diotti, R. A. et al. 2013 JC Polyomavims (JCV) and Monoclonal Antibodies: Friends or Potential Foes?, Clinical and Developmental Immunology, 2013:1-11 (2013).
Dovonex® Prescribing Information, NDA 20-61IS/007, NDA 20-554/S-007, NDA 20-273/S-009, revised 2007.
Durali, D. et al. 2015: B cells and progressive multifocal leukoencephalopathy: search for the missing link, Frontiers in Immunology, 6(241):1-9 (2015).
Durez et al., Safety of Combination of Methotrexate (MTX) and Infliximab (IFX) in a Large Belgian Observational Patient Cohort With Refracotry Rheumatoid Arthritis, Arthritis Rheum., 46(9):S536 (2002).
Dworkin, M. S., A Review of Progressive Multifocal Lenkoencephalopathy in Persons With and Without AIDS, Curr. Clin. Top. Infect. Dis., 22:181-195 (2002).
Edited Transcript: BIIB—Q3 2014 Biogen Idec Inc Earnings Call. Event date/time: Oct. 22, 2014/12:20 GMT. Published by Thomson Reuters Streetevents.
Efficacy and Safety of Oral BGOOO 12 in Relapsing-Remitting Multiple Sclerosis (DEFINE), ClinicalTrials.gov, accessed at http://www.clinicaltrials.gov/ct2/show/NCT00420212?term=bgOOO_12&rank=_1, accessed on Sep. 19, 2008, 4 pages.
Efficacy and Safety Study of Oral BGOOO 12 with Active Reference in Relapsing-Remitting Multiple Sclerosis (CONFIRM), ClinicalTrials.gov, [retrieved on Jul. 7, 2017], accessed at http://www.clinicaltrials.gov/ct2/showlNCT0045 l45 l?term=bgOOO12&rank=8, first received on Mar. 21, 2007, 4 pages.
Elidel® Prescribing Information, NDA21-302/S-OII, revised Jan. 2006.
Elphick, G. F. et al., The Human Polyomavirus, JCV, Uses Serotonin Receptors to Infect Cells, Science, 306(5700):1380-1383 (2004).
Emrich, L., Tecfidera and PML—What's the story, Multiplesclerosis.net, Apr. 25, 2013; accessed Nov. 10, 2014.

(56) References Cited

OTHER PUBLICATIONS

English language information leaflet "Psoriasis" by the Psorinovo Association; submitted Mar. 6, 2013 by Dr. Christian Hollatz as Document D2 in the Opposition against European Patent No. 2 316 430, 4 pages.
Engsig, F. N. et al., Incidence, clinical preparation, and outcome of progressive multifocal leukoencephalopathy in HIV-infected patients during the highly active antiretroviral therapy era: a nationwide cohort study, J. Infect. Dis., 199:77-83 (2009).
Ermis, et al., Fumaric acid-associated progressive multifocal leukencephalopathy (PML), treatment and survival in a patient with psoriasis, [online], Mar. 23, 2013. Retrieved from the Internet: <URL: http://www.ccsvi.nl/prikbord/Direct.aspx?guid=www.facebook.com/notification/a497368459950f_433ce72b8712b45e7c>.
Ermis et al., PML in a Patient Treated with Fumaric Acid, N. Engl. J. Med., 368(17):1657-1658 (including Supplementrarv Appendix) (2013).
European Commission, Commission Implementing Decision dated Jan. 30, 2014, granting marketing authorization under Regulation (EC) No. 726/2004 of the European Parliament and of the Council for "Tecfidera-Dimethylfumarate", a medicinal product for human use (4 pages).
FDA Drug Safety Communication 2014 "FDA warns about case of rare brain infection PML with MS drug Tecfidera (dimethyl fumarate)"[online] Nov. 25, 2014 [retrieved Dec. 11, 2018] retrieved form the internet: URL<https://www.fda.gov/Drugs/DrugSafetv/ucm424625_.htm>.
FDA Drug Safety Communication: FDA warns about cases of rare brain infection with MS drug Gilenya (fingolimod) in two patients with no prior exposure to immunosuppressant drugs, [online] Aug. 4, 2015 [retrieved on May 6, 2019] retrieved from the internet:URL<https://wayback. archive-it.org/7993/20I6I022203738/htto://www.fda.gov/Drugs/DrugSafety/ucm366529.htm>.
FDA Drug Safety Communication: safety update on progressive multifocal leukoencephalopathy (PML) associated with Tysabri (natalizumab) [online], Apr. 22, 2011 [retrieved Jan. 15, 2019]. Retrieved from the Internet <URL: https://www.fda.gov/Drugs/DrugSafety/ucm252045.htm>.
Ferenczy et al., Molecular Biology, Epidemiology, and Pathogenesis of Progressive Multifocal Leukoencephalopathy, the JC Vims-Induced Demyelinating Disease of the Human Brain, Clinical Microbiology Reviews, 25(3):471-506 (2012).
Fludara (fludarabine phosphate), For Injection, For Intravenous Use Only, Ben Venue Laboratories, Rev. Oct. 2003 (5 pages).
Fox, R. et al., Lymphocyte Count Reductions in Relapsing-Remitting Multiple Sclerosis (RRMS) Patients treated with delayed-release Dimethyl Fumarate: An integrated Analysis of Placebo-controlled Studies (P3.179), Neurology, 82 (2014).
Fox et al., Placebo-Controlled Phase 3 Study of Oral BG-12 or Glatiramer in Multiple Sclerosis, 367:1087-97 (2012).
Fox et al., Characterization of Absolute Lymphocyte Count Profiles in MS Patients Treated With Delayed-Release Dimethyl Fumarate: Considerations for Patient Management, AAN Annual Meeting Abstract published in Neurology, 85(4):e48 (2015).
Fox et al., Characterization of Absolute Lymphocyte Count Profiles in MS Patients Treated With Delayed-Release Dimethyl Fumarate: Considerations for Patient Management, poster from the 671 h Annual Meeting of the American Academy of Neurology, Apr. 18-25, 2015, Washington, DC, United States.
Fox et al., Characterizing Absolute Lymphocyte Count Profiles in Dimethyl Fumarate-Treated Patients With MS—Patient Management Considerations, Neurol. Clin. Pract., 6:220-229 (2016).
Frost et al., The importance of mouse models to define immunovirologic determinants of progressive multifocal leukoencephalopathy. Frontiers in Immunology, 5(646):1-10 (2015).
Fumaarzuur—Een Derde Soort Fumaazuur Tabletten, Psoriant, Mar.-May 2004, pp. 4-5 (incl. English Translation), 7 pages.
Garrels et al., Progressive Multifocal Leukoencephalopathy: Clinical and MR Response to Treatment, Am. J. Neuroradiol., 17(3):597-600 (1996).

Gascun et al., Human Polyomavims Reactivation: Disease Pathogenesis and Treatment Approaches, Clinical and Developmental Immunology, 2013:1:27 (2013).
Gesser, et al., Dimethylfumarate specifically inhibits the mitogen and stress-activated kinases 1 and 2 (MSKI/2): possible role for its anti-psoriatic effect, Journal of Investigative Dermatology, 127:2129-2137 (2007).
Gheuens, et al., Progressive multifocal leukoencephalopathy in individuals with minimal or occult immunosuppression, J. Neurol, Neurosurg. Psychiatry, 81(3):247-254 (2010).
Gheuens, et al., Progressive multifocal leukoencephalopathy: Why gray and white matter, Annu. Rev. Pathol. Mech. Dis., 8:189-215 (2013).
Gibson, et al., Detection of JC Vims DNA in the Cerebrospinal Fluid of Patients With Progressive Multifocal Leukoencephalopathy, J. Med. Virol., 39(4):278-281 (1993).
Gold, et al., Placebo-Controlled Phase 3 Study of Oral BG-12 for Relapsing Multiple Sclerosis, N. Engl. J. Med., 367(12):1098-1107 (2102).
Gosert, et al., CMXOOI (1-0-Hexadecyloxypropyl-Cidofovir) Inhibits Polyomavims JC Replication in Human Brain Progenitor-Derived Astrocytes, Antimicrob. Agents Chemother., 55(5):2129-2136 (2011).
Goupil, et al., Lymphopenia and treatment-related infectious complications in ANCA-associated vasculitis, Clin. J Am. Soc. Nephrol., 8:416-423 (2013).
Green, Clinicopatholgic reports, case reports, and small case series, Arch. Ophthalmol., 119:1376-1386 (2001).
Guo, L-P. et al., Developing Treatment in Multiple Sclerosis, Chin J. Clin Neurosci, 20(4): 444-448 (2012).
Habib, et al., Blood B Cell and Regulatory Subset Content in Multiple Sclerosis Patients, J. Mult. Scler. (Foster City), 2(2):1-12 (2015).
Haghikia, et al., Functional energetics of CD4+-cellular immunity in monoclonal antibody-associated progressive multifocal leukoencephalopathy in autoimmune disorders, PLoS One, 6(4):e18506 (2011).
Hatchwell, et al., Is there a (host) genetic predisposition to progressive multifocal leukoencephalopathy?, Frontiers in Immunology, 6(216):1-5 (2015).
Henson et al., Amplification of JC Vims DNA From Brain and Cerebrospinal Fluid of Patients With Progressive Multifocal Leukoencephalopathy, Neurology, 41(12):1967-1971 (1991).
Highlights of Prescribing Information (with Full Prescribing Information), AUBAGIO.TM (teriflunomide) tablets, for oral administration; revised Sep. 2012, 27 pages.
Highlights of Prescribing Information (with Full Prescribing Information), AVONEX.TM (interferon beta-1a) injection, for intramuscular injection, revised Mar. 2013, 19 pages.
Highlights of Prescribing Information (with Full Prescribing Information), BETASERON.TM (interferon beta-1b) for injection, for subcutaneous use, revised Jan. 2014, 30 pages.
Highlights of Prescribing Information (with Full Prescribing Information), COPAXONE.TM (glatiramer acetate injection) solution for subcutaneous injection, revised Aug. 2012, 22 pages.
Highlights of Prescribing Information (with Full Prescribing Information), EXTAVIA.TM (Interferon beta-1b) Kit for subcutaneous use, revised Jul. 2009, 21 pages.
Highlights of Prescribing Information (with Full Prescribing Information), GILENYA.TM (fingolimod) capsules, revised Apr. 2014, 23 pages.
Highlights of Prescribing Information (with Full Prescribing Information), GILENYA.TM (fingolimod) capsules, revised May 2012, 17 pages.
Highlights of Prescribing Information (with Full Prescribing Information), LEMTRADA.TM (alemtuzumab) injection, for intravenous use; revised Nov. 2014, 36 pages.
Highlights of Prescribing Information (with Full Prescribing Information), LEMTRADA.TM., (alemtuzumab) injection, for intravenous use; revised Dec. 2017, 29 pages.
Highlights of Prescribing Information (with Full Prescribing Information), TYSABRI.TM (natalizumab) injection, for intravenous use; revised Dec. 2013, 34 pages.

(56) References Cited

OTHER PUBLICATIONS

Highlights of Prescribing Information for Tecfidera ® (dimethyl fumarate) delayed-release capsules, for oral use; revised Dec. 2014.
Highlights of Prescribing Information for Tecfidera ® (dimethyl fumarate) delayed-release capsules, for oral use; revised Feb. 2016.
Highlights of Prescribing Information for Tecfidera ® (dimethyl fumarate) delayed-release capsules, for oral use; revised Mar. 2013.
Highlights of Prescribing Information Humira (adalimumab) injection, for subcutaneous use. Revised Sep. 2014.
Highlights of Prescribing Information Prograf® (tacrolimus) capsules and injection for intravenous use, Revised Aug. 2013.
Highlights of Prescribing Information Rasuvo (methotrexate) injection, for subcutaneous use. Revised Jul. 2014.
Highlights of Prescribing Information Stelara™ (ustekinumab) injection, for subcutaneous use. Revised Sep. 2009.
Hoffmann, et al., Progressive Multifocal Leucoencephalopathy with Unusual Inflammatory Response During Antiretroviral Treatment, J. Neural. Neurosurg. Psychiatry, 74(8):1142-1144 (2003).
International Preliminary Report on Patentability for International Patent Application No. PCT/US2015/060850, International Bureau of WIPO, Switzerland, dated Jun. 1, 2017.
International Search Report for PCT/US2015/060850 (Methods of Treating Multiple Sclerosis, filed Nov. 16, 2015), issued by ISA/EPO, 4 pages (dated Feb. 16, 2016).
Jamilloux, et al., Progressive multifocal leukoencephalopathy in patients with sarcoidosis, Neurology, 82:1307-1313 (2014).
Jarosz, P.J. and Parrott, E.L., Comparison of Granule Strength and Tablet Tensile Strength, Journal of Pharmaceutical Sciences, 72(5):530-535 (1983).
Kakar, et al., Absolute lymphocyte count: a cost-effective method of monitoring HIV-infected individuals, Indian J. Pathol. Microbial., 54(1):107-111 (2011).
Kalashnikova, A. A., Changes in immunity parameters in patients with multiple sclerosis depending on variants of disease process and activity, Author's abstract, Saint-Petersburg (2002).
Kappos, et al., Efficacy and Safety of Oral Fumarate in Patients With Relapsing-Remitting Multiple Sclerosis: A Multicentre, Randomised, Double-Blind, Placebo-Controlled Phase IIb Study, Lancet. 372:1463-1472 (2008).
Khatri, et al., The Effect of Dimethyl Fumarate (Tecfidera™) on Lymphocyte Counts: A Potential Contributor to Progressive Multifocal Leukoencephalopathy Risk, Mult. Scler. Relat. Disord., 4(4):377-379 (2015).
Klastersky, et al., Opportunistic infections in patients with cancer, Ann. Oneal., 15(Suppl. 4):iv329-iv335 (2004).
Koralnik, et al., New Insights into Progressive Multifocal Leukoencephalopathy, Curr. Opin. Neurol., 17(3):365-370 (2004).
Kunst, L., Fumaarzuurtherapie bij Psoriasis, Tijdschrift voor Integrale Geneeskunde, Dutch Journal of Integral Medicine, 14:243-251:1-19 (including English language translation) (1998).
Kurukulasuriva, N. C. et al., Five-Year Follow-up of Delayed-Release Dimethyl Furnarate in RRMS: Integrated Clinical Efficacy Data From the DEFINE, CONFIRM, and ENDORSE studies, Poster presented at Joint ECTRIMS-ACTRIMS Meeting, Sep. 10-13, 2014, Boston, MA; Poster Abstract P110.
Kurukulasuriya, N. C. et al., Five-Year Follow-up of Delayed-Release Dimethyl Fumarate in Relapsing-Remitting Multiple Sclerosis: MRI Outcomes from DEFINE, CONFIRM, and ENDORSE, Poster presented at Joint ECTRIMS-ACTRIMS Meeting, Sep. 10-13, 2014, Boston, MA; Poster Abstract P059.
Lachman, et al. The Theory & Practice of Industrial Pharmacy, 3rd edition, 295-303, Lea & Febiger, United States, 1986.
Langer-Gould, et al., Progressive Multifocal Leukoencephalopathy in a Patient Treated with Natalizumab, N. Engl. J. Med., 353(4):375-381 (2005).
Langewouters, et al., Lymphocyte subsets in peripheral blood of patients with moderate-to-severe versus mild plaque psoriasis, Arch Dermatol Res 300(3):107-113 (2008).

Lecewicz-Torun, et al., The peripheral blood lymphocyte pattern in psoriasis preceded by an Infection, Med Sci Monit. 7(5):889-893 (2001).
Lehmann et al., Dimethylfumarate induces immunosuppression via glutathione depletion and subsequent induction of heme oxvgenase I, Journal of Investigative Dermatology, 127:835-845 (2007).
Lehmann-Horn et al., PML During Dimethyl Fumarate Treatment of Multiple Sclerosis: How Does Lymphopenia Matter?, Neurology, 87(4):440-441 (2016).
Lemtrada™ (alemtuzumab) injection, for intravenous use, Highlights of Prescribing Information and Medication Guide, Genzyme Corporation, Nov. 2014.
Letter from Amit Rakhit, MD, SVP, Head, Global Medical Organization, Biogen Idec, "Important Drug Warning," Feb. 13, 2015.
Lim, et al., Lymphopenia in treatment-nai′ve relapsing multiple sclerosis, Neurol. Neuroimmunol., 2016:e275 (2016).
Linker, et al., Dimethy1 Fumarate in Multiple Sclerosis: Latest Developments, Evidence and Place in Therapy, Ther. Adv. Chronic Dis., 7(4) 198-207 (2016).
Liu et al., Peripheral Leukocytes in Psoriasis, Int. J. Dermatol. 27(9):638-641 (1988).
Longbrake et al., Dimethyl fumarate-associated lymphopenia: Risk factors and clinical significance, Multiple Sclerosis Journal—Experimental, Translational and Clinical, 1:1-8 (2015).
Lowes et al., Current concepts in the immunopathogenesis of psoriasis, Dermatol Clin 22 (2204): 349-369 (2004).
Lublin et al., Defining the clinical course of multiple sclerosis: Results of an international survey, Neurology 46:907-911(1996).
Lugaresi et al., Risk-benefit considerations in the treatment of relaspin-remitting multiple sclerosis, Neuropsychiatric Disease and Treatment, 9:893-914 (2013).
Luo et al., Idiopathic CD4 lymphocytopenia and opportunistic infection—an update, FEMS Immunol. Med. Microbial., 54:283-289 (2008).
Lynch et al., Treating moderate to severe psoriasis—best use of biologics, Expert Rev. Immunol. 10(2):269-279 (2014).
Major et al., Pathogenesis and molecular biology of progressive multifocal leukoencephalopathy, the JC virus-induced demyelinating disease of the human brain, Clin. Microbial. Rev., 5(1):49-73 (1992).
Major, Progressive Multifocal Leukoencephalopathy in Patients on Immunomodulatory Therapies, Annu. Rev. Med., 61:35-47 (2010).
Mamidi et al., Central Nervous System Infections in Individuals With HIV-1 Infection, J. Neurovirol., 8(3):158-167 (2002).
Mateen et al., Progressive multifocal leukoencephalopathy in transplant recipients, Ann. Neural., 70:305-322 (2011).
Matos et al., Characterization of JC human polyomavirus infection in a Portuguese population, J. Med. Viral., 82:494-504 (2010).
Mease et al., Managing Patients with Psoriatic Disease: The Diagnosis and Pharmacologic Treatment of Psoriatic Arthritis in Patients with Psoriasis, Drug 74:423-441 (2014).
Medical Communication Brief, "Progressive Multifocal Leukoencephalopathy (PML) in a Patient Receiving Tecfidera", Biogen idec, Dec. 10, 2014.
Medication Safety in Seconds 10(4):2 "FDA warns about case of rare brain infection PML with MS drug Tecfidera (dimethyl fumarate)" Nov. 25, 2014 [retrieved Feb. 12, 2019]. Published by VA Medsafe. Retrieved from the internet <URL: https://www.pbm.va.gov/PBM/vacenterformedicationsafety/newsletter/Medication_Safety_in_Second_s_NovDec_2014_FINAL.pdf>.
Medscape Website "FDA Warns of PML Risk With Fingolimod (Gilenya) in MS," [online] Aug. 4, 2015 [retrieved on May 6, 2019] retrieved from the internet: URL<https://www.medscape.com/viewarticle/849015>.
Menter et al., Guidelines of care for the management of psoriasis and psoriatic arthritis, J. Am. Acad. Dermatl. 58(5):826-850 (2008).
Miller, The Importance of Early Diagnosis of Multiple Sclerosis, J. Manag. Care Pharm. 10(3):S4-SII (2004).
Mocroft et al., The incidence of AIDS-defining illnesses at a current CD4 count 2':200 cells/µL in the post-combination antiretroviral therapy era, Clin. Infect. Dis., 57(7):1083-1047 (2013).
Molloy, PML and rheumatology: The contribution of disease and drugs, Cleveland Clinic Journal of Medicine, 78(2):S28-S32 (2011).

(56) References Cited

OTHER PUBLICATIONS

Molloy et al., Progressive multifocal leukoencephalopathy associated with immunosuppressive therapy in rheumatic diseases, Arthritis Rheum., 64(9):3043-3051 (2012).
Molloy et al., Progressive multifocal leukoencephalopathy: a national estimate of frequency in systemic lupus erythematosus and other rheumatic diseases, Arthritis Rheum., 60(12):3761-3765 (2009).
Mouzaki et al., Immune Parameters That Distinguish Multiple Sclerosis Patients from Patients with Other Neurological Disorders at Presentation, PLoS One, 10(8):e013543492015).
Mrowietz et al., Treatment of Severe Psoriasis with Fumaric Acid Esters: Scientific Background and Guidelines for Therapeutic Use, Br. J. Dermatol., 141(3):424-29 (1999).
National Cancer Institute. Common Terminology Criteria for Adverse Events v4.0, NCI, NIH, DHHS, May 28, 2009, NIH publication# 09-7473.
Neoral® Soft Gelatin Capsules and Oral Solution Prescribing Information. Revised Aug. 2012.
Nestle et al. 2009: "Psoriasis". NEJM 361(5):496-509.
Newton, J. M, The Calculation of the Tensile Strength of Tablets, J. Pharm. Pharmacol. 26:215-216 (1974).
Nieuwkamp et al., PML in a Patient without Severe Lymphocytopenia Receiving Dimethyl Fumarate, N. Engl. J. Med., 372(15):1474-1476 (2015).
Ontaneda, D. et al., Risk stratification and mitigation in Multiple Sclerosis, Mult. Scler. Relat. Disord., 3(5): 639-649 (2014).
Ortiz et al., A Treatment Strategy for Psoriasis: Transitioning from Systemic Therapy to Biologic Agents, SKINMed 6(5):285-290 (2007).
Package Insert, NOVATRONE.TM.,mitoxantrone, for injection concentrate, 2000, 35 pages.
Padgett and Walker, Virologic and Serologic Studies of Progressive Multifocal Leukoencephalopathv, Prog. Clin. Biol. Res.,105:107-117 (1983).
Palazzo et al., Progressive multifocal leukoencephalopathy in autoimmune diseases, Joint Bone Spine, 79:351-55 (2012).
Pandeya, A. and Puri, V.M., Feasibility of Relationships between Tablet Physical Quality Parameters and Mechanical Properties of Dry Powder Formulation, KONA Powder and Particle Journal, 30:211-220 (2013).
Pavlovic et al., T cell deficiencies as a common risk factor for drug associated progressive multifocal leukoencephalopathy, Immunobiology, 223:508-517 (2018).
Polman et al., Diagnostic Criteria for Multiple Sclerosis: 2005 Revisions to the 'McDonald Criteria', Ann. Neurol. 58(6):840-846 (2005).
Post et al., Progressive Multifocal Leukoencephalopathy in AIDS: Are There Any MR Findings Useful to Patient Management and Predictive of Patient Survival? AIDS Clinical Trials Group, 243 Team, Am. J. Neuroradiol., 20(10):1896-1906 (1999).
Pozzilli et al., Long-Term Follow-up of the Safety of Delayed-Release Dimethyl Fumarate inRRMS: Interim Results From the ENDORSE Extension Study, Poster presented at Joint ECTRIMS-ACTRIMS Meeting, Sep. 10-13, 2014, Boston, MA; Poster Abstract P066.
Protopic® (tacrolimus) ointment 0.03% and 0.1% Prescribing Information. Revised Nov. 2011.
Przepiorka et al., Successful Treatment of Progressive Multifocal Leukoencephalopathy With Low-Dose Interleukin-2., Bone Marrow Transplant, 20(11):983-987 (1997).
Puissant-Lubrano et al., Thymic output and peripheral T lymphocyte subsets in relapse-remitting multiple sclerosis patients treated or not by IFN-B, J. Neuro. Im., 193:188-194 (2008).
Ramirez-Fort et al, Continuous versus intermittent therapy for moderate-to-sever psoriasis, Clinical and Experimental Rheumatology 31(4); Supplementary 78 (2013).
Rankin et al., Progressive Multifocal Leukoencephalopathy in a Patient with Rheumatoid Arthritis and Polymyositis, J. Rheumatol., 22(4):777-779 (1995).

Redington and Tyler, Viral Infections of the Nervous System, 2002: Update on Diagnosis and Treatment, Arch. Neural., 59(5):712-718 (2002).
Rice et al., Anti-a4 integrin therapy for multiple sclerosis: Mechanisms and rationale, Neurology, 64:1336-1342 (2005).
Rieckmann et al., Haematological Effects of Interferon-la (Rebif®) Therapy in Multiple Sclerosis, Drug Safety 27(10):745-756 (2004).
Rituxan (rituximab), Highlights of Prescribing Information, Full Prescribing Information, Biogen Idec Inc. and Genentech, Inc., Revised Oct. 2012.
Rosenkranz et al., PML in a Patient with Lymphocytopenia Treated with Dimethyl Furnarate, N. Engl. J. Med., 372(15):1476-1478 (2015).
Sagar et al., Lymphocyte subpopulations in Multiple Sclerosis, J. Neuro. Sci., 43:133-148 (1979).
Scalfari et al., Mortality in patients with multiple sclerosis, Neurology, 81:184-192 (2013).
Schimrigk et al., Oral Fumaric Acid Esters for the Treatment of Active Multiple Sclerosis: An Open-Label, Baseline-Controlled Pilot Study, European Journal of Neurology, 13(6):604-610 (2006).
Schmedt et al., Signals of progressive multifocal leukoencephalopathy for immunosuppressants: a disproportionality analysis of spontaneous reports within the US adverse event reporting system (AERS), Pharmacoepidemiology and Drug Safety, published online in John Wiley Library, (wilevonlinelibrarv.com), DOI: 10.1002/pds.3320 (2012).
Seth et al., Advances in the Biology of JC Vims and Induction of Progressive Multifocal Leukoencephalopathy, J. Neurovirol., 9(2):236-246 (2003).
Shapiro et al., Absolute lymphocyte count as a predictor of CD4 count, Ann. Emerg. Med., 32:323-328 (1998).
Sheremata et al., Dimethyl fumarate for treating relapsing multiple sclerosis, Expert Opin. Drug Saf, 14(1):161-170 (2014).
Song et al., Peripheral Blood T Cell Dynamics Predict Relapse in Multiple Sclerosis Patients on Fingolimod, PLoS One 10(4):e0124923 (2015).
Sponzilli et al., Progressive Multifocal Leukoencephalopathy: A Complication of Immunosuppressive Treatment, Neurology, 25(7):664-668 (1975).
Stoppe, M. et al., Cerebellar manifestation of PML under fumarate and after efalizumab treatment of psoriasis, J. Neurol., 261(5): 1021-4 (2014).
Summary of Product Characteristics for Fumaderm® Initial/ Fumaderm®; date ofrevision Sep. 2010.
Summary of Product Characteristics for Fumaderm® Initial/ Fumaderm® (English translation of original German version) (2006).
Summary of Product Characteristics for Fumaderm® Initial/ Fumaderm®, dated Jan. 2004 (cited as Document D7 in the Opposition against European Patent No. 2 316 430).
Summary of Product Characteristics for Fumaderm® Initial/ Fumaderm®; date of revision Apr. 2005.
Summary of Product Characteristics Tecfidera, retrieved from internet <<https://web.archive.org/web/20141011193051/http://www.ema.europa.eu/docs/en GB/document library/EPAR - Product Information/human/002601/WC500162069.pdf>>, accessed on Feb. 2, 2016, pp. 1-49 (Oct. 11, 2014). {Specifically Sections on Blood/ Laboratory Tests and Haematological pp. 3, 7, 17, 21] [Annex 1].
Sweetser et al., Manufacturer's Reponse to Case Reports of PML, N. Engl. J. Med., 368(17):1659-1660 (2013).
Tan et al., HIV-associated opportunistic infections of the CNS, Lancet Neural., 11:605-617 (2012).
Tazorac®(tazarotene) Gel 0.05% and 0.1% NDA 020600, Revised Feb. 2011.
Tecfidera® (dimethyl fumarate): Lymphopenia, Biogen idec, Oct. 24, 2014.
Tedfidera® (dimethyl fumarate): PML Case Report, Biogen idec, Oct. 24, 2014.
Tedfidera® (dimethyl fumarate): Treatment Interruption or Discontinuation Due to Low Lymphocyte Levels, Biogen idec, Oct. 24, 2014.
The HIV-Causal Collaboration et al., "Opportunistic infections and AIDS malignancies early after initiating combination antiretroviral therapy in high-income countries," AIDS, 28(16):2461-2473 (2014).

(56) References Cited

OTHER PUBLICATIONS

Thompson et al., Peripheral blood T lymphocyte changes in multiple sclerosis: a marker of disease progression rather than of relapse?, Journal of Neurology, Neurosurgery and Psychiatry, 49:905-912 (1986).
Tourbah, A. et al, Immunology of multiple sclerosis. Recent data and therapeutic perspectives, Rev. Neurol. (Paris). 149(6-7): 373-84 (1993). [French with English Abstract].
Treumer et al., Dimethylfumarate is a potent inducer of apoptosis in human T cells, Journal of Investigative Dermatology, 121(6):1383-1388 (2003).
Tyler et al, Progressive Multifocal Leukoencephalopathy: Can We Reduce Risk in Patients Receiving Biological Immunomodulatory Therapies?, Annals of Neurology 68(3):271-274. (2010).
Tyler, PML Therapy: 'It's Deja vu All Over Again', J. Neurovirol., 19(4):311-313 (2013).
Vago et al., JCV-DNA and BKV-DNA in the CNS Tissue and CSF of AIDS Patients and Normal Subjects. Study of 41 Cases and Review of the Literature, J. Acquir. Imm. Defic. Syndr. Hum. Retrovirol., 12(2):139-146 (1996).
Van Der Ryst et al., Correlation among total lymphocyte count, absolute CD4+ count, and CD4+ percentage in a group of HIV-I-infected South African patients, J. Acquired Immune Deficiency Syndromes & Human Retrovirology, 19:238-244 (1998).
Vandermeeren et al., Dimethylfumarate is an inhibitor of cytokine-induced E-selectin, VCAM-1, and ICAM-1 expression in human endothelial cells, Biochemical and Biophysical Research Communications, 234:19-23 (1997).
Vanoosten et al., PML in a Patient Treated with Dimethyl Fumarate from a Compounding Pharmacy, N. Engl. J. Med., 368(17):1658-1659 (including Supplementary Appendix and Correction) (2013).
Verma et al., Mirtazapine in Progressive Multifocal Leukoencephalopathy Associated With Polycythemia Vera, J. IufectDis., 196(5):709-711 (2007).
VHA Pharmacy Benefits Management Services, Medical Advisory Panel and VISN Pharmacist Executives: "Dimethyl Fumarate (Tecfidera) Criteria for Use" [online], Aug. 2013 (update Mar. 2014) [retrieved Jan. 25, 2019]. Retrieved from the Internet: <URL:https://web.archive.org/web/20160309225124/https://www.pbm.va.gov/PBM/clinicalguidance/criteriafomse/Dimethyl_Fumarate_Tecfidera_CFU_update_March_2014.doc> (with screenshot inserted at end of document showing "Content created Mar. 31, 2014 12:16 PM").
VHA Pharmacy Benefits Management Services, Medical Advisory Panel and VISN Pharmacist Executives: "Dimethyl Fumarate (Tecfidera) Criteria for Use" [online], Aug. 2013 (update Mar. 2014, Mar. 2017, Aug. 2018) [retrieved Jan. 15, 2019]. Retreived from the Internet: <URL: https://www.pbm.va.gov/aoosNANationalFormularv/GetFile.aspx>.
VHA Pharmacy Benefits Management Services, Medical Advisory Panel and VISN Pharmacist Executives: "Dimethyl Fumarate (Tecfidera) Criteria for Use" [online], Aug. 2013 [retrieved Feb. 26, 2019]. Retrieved from the Internet <URL: https://web.archive.org/web/20131001053646/http://www.pbm.va.gov/PBM/clinicalguidance/criteriaf_oruse/Dimethyl_Fumarate_Tecfidera_CFU.doc >.
VHA Pharmacy Benefits Management Services, Medical Advisory Panel and VISN Pharmacist Executives: "Dimethyl Fumarate (Tecfidera) National Drug Monograph" [online], May 2013 [retrieved Jan. 15, 2019]. Retrieved from the Internet: <URL: https://www.pbm.va.gov/PBM/clinicalguidance/drugmonographs/Dimethyl_Fumarate_Tecfidera_NM_E_Monograph.doc>.
Walker et al., Idiopathic CD4 lymphocytopenia, Curr. Opin. Rheumatol., 18:389-395 (2006).
Weber et al., Progressive Multifocal Leukoencephalopathy Diagnosed by Amplification of JC Vims-Specific DNA From Cerebrospinal Fluid, AIDS, 8(1):49-57 (1994).
Weber et al., Specific Diagnosis of Progressive Multifocal Leukoencephalopathy by Polymerase Chain Reaction, J. Infect. Dis., 169(5): 1138-1141 (1994).
Weiner et al., Lymphocytes in Multiple Sclerosis, Neurology, 29(11): (1979).
Written Opinion for PCT/US2015/060850 (Methods of Treating Multiple Sclerosis, filed Nov. 16, 2015), issued by ISA/EPO, 7 pages (dated Feb. 16, 2016).
Yin et al., Systemic abnormalities of psoriatic patients a retrospective study, Clinical, Cosmetic and Investigational Dermatology, 2016:9 443-449 (2016).
Young et al., Progressive Multifocal Leukoencephalopathy with Immune Reconstitution Inflammatory Syndrome (PML-IRIS): Two Case Reports of Successful Treatment with Mefloquine and a Review of the Literature, Ann. Acad. Med. Singap., 41(12):620-624 (2012).
Yousry et al., Evaluation of Patients Treated with Natalizumab for Progressive Multifocal Leukoencephalopathy, N. Engl. J. Med., 354(9):924-933 (2006).
Zaheer et al., Treatment-related progressive multifocal leukoencephalopathy: current understanding and future steps, Ther. Adv. Drug Safety, 3(5):227-239 (2012).
Zhou, G. et al, Advance in New Oral Drugs for Multiple Sclerosis, Chinese Journal of Contemporary Neurology and Neurosurgery, 12(2): 147-151 (2012).
Zonios et al., Idiopathic CD4 lymphocytopenia: a case of missing, wandering or ineffective T cells, Arthritis Res. Ther., 14:222 (2012).
Zonios et al., Idiopathic CD4+ lymphocytopenia: natural history and prognostic factors, Blood, 112:287-294 (2008).
Statement of Relatedness, Methods of Treating Multiple Sclerosis Patent Family, Aug. 10, 2020.
Declaration of Dr. Mark Novas under 37 C.F.R. § 1.132 that was filed in U.S. Appl. No. 15/647,016 on Jul. 20, 2020, with accompanying exhibits, 25 pages.
Declaration of Dr. Cahir-McFarland under 37 C.F.R. § 1.132 that was filed in U.S. Appl. No. 15/647,016 on Aug. 5, 2019, with accompanying exhibits, 374 pages.

\* cited by examiner

METHODS OF TREATING MULTIPLE SCLEROSIS

CROSS-REFERENCES TO RELATED APPLICATIONS

This application is a continuation of U.S. application Ser. No. 15/527,252, filed May 16, 2017, which is the National Stage of International Application No. PCT/US2015/060850, filed Nov. 16, 2015, which claims the benefit of U.S. Provisional Patent Application No. 62/080,783, filed Nov. 17, 2014, U.S. Provisional Patent Application No. 62/140,255, filed Mar. 30, 2015, and U.S. Provisional Patent Application No. 62/232,963, filed Sep. 25, 2015, the contents of all of are incorporated herein by reference in their entirety.

1. FIELD

Provided herein are methods of treating multiple sclerosis with a fumarate, such as a dialkyl fumarate, monoalkyl fumarate, a combination of a dialkyl fumarate and a monoalkyl fumarate, a prodrug of monoalkyl fumarate, a deuterated form of any of the foregoing, and a pharmaceutically acceptable salt, clathrate, solvate, tautomer, or stereoisomer of any of the foregoing, or a combination of any of the foregoing. The methods provided herein improve the safety of treatment by informing and monitoring patients undergoing treatment regarding progressive multifocal leukoencephalopathy (PML), and/or by monitoring lymphocyte count.

2. BACKGROUND

Multiple sclerosis (MS) is an autoimmune disease with the autoimmune activity directed against central nervous system (CNS) antigens. The disease is characterized by inflammation in parts of the CNS, leading to the loss of the myelin sheathing around neuronal axons (demyelination), axonal loss, and the eventual death of neurons, oligodendrocytes and glial cells. For a comprehensive review of MS and current therapies, see, e.g., McAlpine's Multiple Sclerosis, by Alastair Compston et al., 4th edition, Churchill Livingstone Elsevier, 2006.

An estimated 2,500,000 people in the world suffer from MS. It is one of the most common diseases of the CNS in young adults. MS is a chronic, progressing, disabling disease, which generally strikes its victims some time after adolescence, with diagnosis generally made between 20 and 40 years of age, although onset may occur earlier. The disease is not directly hereditary, although genetic susceptibility plays a part in its development. MS is a complex disease with heterogeneous clinical, pathological and immunological phenotype.

There are four major clinical types of MS: 1) relapsing-remitting MS (RR-MS), characterized by clearly defined relapses with full recovery or with sequelae and residual deficit upon recovery; periods between disease relapses characterized by a lack of disease progression; 2) secondary progressive MS (SP-MS), characterized by initial relapsing remitting course followed by progression with or without occasional relapses, minor remissions, and plateaus; 3) primary progressive MS (PP-MS), characterized by disease progression from onset with occasional plateaus and temporary minor improvements allowed; and 4) progressive relapsing MS (PR-MS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS (RR-MS) presents in the form of recurrent attacks of focal or multifocal neurologic dysfunction. Attacks may occur, remit, and recur, seemingly randomly over many years. Remission is often incomplete and as one attack follows another, a stepwise downward progression ensues with increasing permanent neurological deficit. The usual course of RR-MS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes.

Periods between relapses during the relapsing-remitting phase are clinically stable. On the other hand, patients with progressive MS exhibit a steady increase in deficits, as defined above and either from onset or after a period of episodes, but this designation does not preclude the further occurrence of new relapses.

MS pathology is, in part, reflected by the formation of focal inflammatory demyelinating lesions in the white matter, which are the hallmarks in patients with acute and relapsing disease. In patients with progressive disease, the brain is affected in a more global sense, with diffuse but widespread (mainly axonal) damage in the normal appearing white matter and massive demyelination also in the grey matter, particularly, in the cortex.

Salts of fumaric acid esters, in combination with dimethyl fumarate (DMF), such as present in FUMADERM®, have been proposed for the treatment of MS (see, e.g., Schimrigk et al., Eur. J. Neurol., 2006, 13(6):604-610; Drugs R&D, 2005, 6(4):229-30; U.S. Pat. No. 6,436,992). FUMADERM® contains dimethyl fumarate, calcium salt of ethyl hydrogen fumarate, magnesium salt of ethyl hydrogen fumarate, and zinc salt of ethyl hydrogen fumarate (see, e.g., Schimrigk et al., Eur. J. Neurol., 2006, 13(6):604-610).

TECFIDERA®, dimethyl fumarate delayed-release capsules for oral use, was approved in 2013 by the U.S. Food and Drug Administration for the treatment of subjects with relapsing forms of multiple sclerosis. TECFIDERA© contains dimethyl fumarate (DMF), which has the following structure:

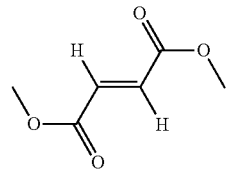

The first Phase 3 study, DEFINE (ClinicalTrials.gov identifier NCT00420212), demonstrated that DMF significantly reduced clinical relapses, accumulation of disability progression, and lesion number and volume compared with placebo after two years of treatment. See, e.g., Gold et al., N. Engl. J. Med., 2012, 367(12):1098-1107. These findings were supported by the results of the second phase 3 study, CONFIRM (ClinicalTrials.gov identifier NCT00451451), which additionally evaluated subcutaneous glatiramer acetate as an active reference treatment (rater-blind). See, e.g., Fox et al., N. Engl. J. Med., 2012, 367(12):1087-1097. DMF has demonstrated an acceptable safety profile in the DEFINE and CONFIRM studies.

There have been case reports of patients with psoriasis, treated with FUMADERM® or compounded fumaric acid esters, who developed PML (Ermis et al., N. Engl. J. Med., 2013, 368(17):1657-1658; van Oosten et al., N. Engl. J. Med., 2013, 368(17):1658-1659; Sweetser et al., N. Engl. J. Med., 2013, 368(17):1659-1658; Emrich, Lisa, "Tecfidera and PML—What's the story." Multiplesclerosis.net, Apr. 25, 2013; accessed Nov. 10, 2014).

PML is an opportunistic viral infection caused by a type of polymavirus called the JC virus (JCV) that typically only occurs in patients who are immunocompromised, and that usually leads to death or severe disability. The virus is very common in the general population, occurs in childhood, and persists for life. JCV seroprevalence of ~33-84% has been demonstrated, depending on the studies (see WO 2011/085369 A1, WO2007/100770 A2, and WO 2012/166971 A2). PML is a severe and rapidly progressive viral disease of the central nervous system that destroys the myelin coating, which protects the nerve cells. PML occurs almost exclusively in patients who are severely immunocompromised, and is often associated with lymphoproliferative and other chronic diseases, such as AIDS, Hodgkin's disease, chronic lymphocytic leukemia, sarcoidosis, tuberculosis, systemic lupus erythematosus, and organ transplantation. Cases of PML have also been reported in patients with autoimmune disorders who received immunosuppressive therapy; among these, three patients with rheumatoid arthritis (Sponzilli et al., Neurology, 1975, 25(7):664-668; Rankin et al., J. Rheumatol., 1995, 22(4):777-779; Durez et al., Arthritis Rheum., 2002, 46(98):536), one of whom was treated with tumor necrosis factor (TNF) antagonist (Durez et al., Arthritis Rheum., 2002, 46(98):536). PML also was reported in a Crohn's Disease patient, but the concomitant treatments were not specified (Garrels et al., Am. J. Neuroradiol., 1996, 17(3):597-600), and in patients treated with natalizumab, a humanized monoclonal antibody used in the treatment of multiple sclerosis, and Crohn's disease. In 2005, the first cases of PML associated with biological immunomodulatory therapy were reported, initially with natalizumab and subsequently in association with other agents including efalizumab, rituximab, and alemtuzumab (reviewed in: Major et al., Annu. Rev. Med., 2010, 61:35-47).

There is need in the art for safer methods of treating patients with fumarates that take into account the possibility of contracting PML.

3. SUMMARY

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) monitoring the patient for a sign or symptom suggestive of progressive multifocal leukoencephalopathy (PML) in the patient.

Provided herein is a method of improving safety in treatment of a patient with multiple sclerosis comprising monitoring a patient with multiple sclerosis who is being treated with a fumarate for a sign or symptom suggestive of PML in the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) informing the patient that PML has occurred in a patient who received dimethyl fumarate.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a fumarate that PML has occurred in a patient who received dimethyl fumarate, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of improving safety in treatment of a patient with multiple sclerosis comprising instructing a patient with multiple sclerosis who is being treated with a fumarate of the importance of contacting the patient's doctor if the patient develops any symptoms suggestive of PML, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

In one embodiment, the method further comprises withholding treatment with the fumarate from the patient at the first sign or symptom suggestive of PML in the patient.

In one embodiment, the method further comprises performing a diagnostic evaluation for PML in the patient at the first sign or symptom suggestive of PML in the patient.

In one embodiment, the method further comprises administering a therapeutic to the patient for the treatment for the treatment of PML when the diagnostic evaluation indicates PML in the patient.

In one embodiment, the method further comprises instructing the patient to continue to look for new signs and symptoms suggestive of PML for approximately 6 months following discontinuation of treatment with the fumarate.

In one embodiment, the method further comprises instructing the patient that typical symptoms associated with PML are diverse, progress over days to weeks, and include progressive weakness on one side of the body or clumsiness of limbs, disturbance of vision, and changes in thinking, memory, and orientation leading to confusion and personality changes.

In one embodiment, the method further comprises instructing the patient that progression of deficits associated with PML usually leads to death or severe disability over weeks or months.

In one embodiment, the diagnostic evaluation comprises a test for the presence of JC viral DNA in the cerebrospinal fluid of the patient.

In one embodiment, the sign or symptom suggestive of PML is selected from the group consisting of progressive weakness on one side of the body or clumsiness of limbs, disturbance of vision, and changes in thinking, memory, and orientation leading to confusion and personality changes.

In one embodiment, administering is done orally.

In one embodiment, the pharmaceutical composition comprises a therapeutically effective amount of the fumarate and a pharmaceutically acceptable carrier.

In one embodiment, the pharmaceutical composition is in the form of a tablet or a capsule.

In one embodiment, the pharmaceutical composition is in the form of an enterically coated tablet.

In one embodiment, the pharmaceutical composition is in the form of a capsule containing enterically coated microtablets.

In one embodiment, the fumarate is dimethyl fumarate and/or monomethyl fumarate.

In one embodiment, the fumarate is dimethyl fumarate

In one embodiment, the administering is of 240 mg twice daily of dimethyl fumarate.

In one embodiment, the administering is of 120 mg dimethyl fumarate twice daily for 7 days, followed by 240 mg dimethyl fumarate twice daily as a maintenance dose.

In one embodiment, the administering is of not greater than 720 mg daily total fumarates.

In one embodiment, the administering is of not greater than 480 mg daily total fumarates.

In one embodiment, the pharmaceutical composition consists essentially of dimethyl fumarate, and the administering is of not greater than 720 mg daily dimethyl fumarate.

In one embodiment, the pharmaceutical composition consists essentially of dimethyl fumarate, and the administering is of not greater than 480 mg daily dimethyl fumarate.

In one embodiment, the pharmaceutical composition consists essentially of dimethyl fumarate.

In one embodiment, the multiple sclerosis is a relapsing form of multiple sclerosis.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method od treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition consisting essentially of dimethyl fumarate and/or monomethyl fumarate to the patient; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition consisting essentially of dimethyl fumarate and/or monomethyl fumarate for a sign or symptom suggestive of PML in the patient.

Provided herein is a method of treating a patient with multiple sclerosis comprising (a) administering a pharmaceutical composition consisting essentially of dimethyl fumarate and/or monomethyl fumarate to the patient; and (b) informing the patient that PML has occurred in a patient who received dimethyl fumarate.

Provided herein is a method of treating a patient with multiple sclerosis comprising (a) administering a pharmaceutical composition consisting essentially of dimethyl fumarate and/or monomethyl fumarate to the patient; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition consisting essentially of dimethyl fumarate and/or monomethyl fumarate that PML has occurred in a patient who received dimethyl fumarate.

Provided herein is a method of improving safety in treatment of a patient with multiple sclerosis comprising instructing a patient with multiple sclerosis who is being treated with a pharmaceutical composition consisting essentially of dimethyl fumarate and/or monomethyl fumarate of the importance of contacting the patient's doctor if the patient develops any symptoms suggestive of PML.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition consisting essentially of dimethyl fumarate and/or monomethyl fumarate to the patient; and (b) obtaining a complete blood count including lymphocyte count after 6 months of repeated administering of said pharmaceutical composition to said patient, and every 6 to 12 months thereafter.

In one embodiment, the method further comprises interrupting administering of said pharmaceutical composition to said patient when the patient has a lymphocyte count less than $0.5 \times 10^9$/L persisting for more than six months.

In one embodiment, the method further comprises measuring lymphocyte count in said patient until lymphopenia is resolved in said patient.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a A method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient;

wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a A method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition consisting essentially of dimethyl fumarate and/or monomethyl fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient.

Provided herein is a method of treating a patient with multiple sclerosis comprising (a) repeatedly administering a pharmaceutical composition consisting essentially of dimethyl fumarate and/or monomethyl fumarate to the patient; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition consisting essentially of dimethyl fumarate and/or monomethyl fumarate to the patient; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition consisting essentially of dimethyl fumarate and/or monomethyl fumarate, and who experiences lymphopenia, for signs or symptoms of appearance of new neurological dysfunction.

Provided herein is a method of treating multiple sclerosis in a patient who is being treated with a multiple sclerosis disease-modifying therapy other than a pharmaceutical composition consisting essentially of dimethyl fumarate and/or monomethyl fumarate; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition consisting essentially of dimethyl fumarate and/or monomethyl fumarate.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering a pharmaceutical composition consisting essentially of dimethyl fumarate and/or monomethyl fumarate to the patient.

Provided herein is a method of treating a patient with multiple sclerosis comprising (a) administering a pharmaceutical composition consisting essentially of dimethyl fumarate and/or monomethyl fumarate to the patient; and (b) prior to the initial administering of said pharmaceutical composition to the patient, and periodically during treatment of said patient with said pharmaceutical composition, having a blood test done to count the number of white blood cells in the patient; and (c) considering stopping said treatment with said pharmaceutical composition if the number of white blood cells decreases during said treatment.

In one embodiment, the method further comprises discontinuing administering of said pharmaceutical composition to said patient when the patient has a lymphocyte count less than $0.7 \times 10^9/L$ that is confirmed on repeat testing after 3 months.

In one embodiment, the signs or symptoms of appearance of new neurological dysfunction comprise motor dysfunction and cognitive or psychiatric symptoms.

In one embodiment, the method further comprises: if PML is suspected, withholding treatment with said pharmaceutical composition immediately and performing further evaluations.

In one embodiment, the method further comprises performing an MRI on the patient before said starting administering to the patient of the pharmaceutical composition comprising the fumarate.

3.1 Terminology

In order to provide a clear and consistent understanding of the specification and claims, the following definitions are provided:

The term "alkanediyl," as used herein refers to linear or branched alkyl chains with, for example 1 to 6 carbon atoms. Representative examples of aklanediyl groups include, but are not limited to —$CH_2$—, —$(CH_2)_2$—, —$CH(CH_3)$—, —$(CH_2)_3$—, —$CH_2CH(CH_3)$—, —$CH(CH_3)CH_2$—, —$CH(C_2H_5)$—, —$C(CH_3)_2$—, —$(CH_2)_4$—, —$(CH_2)_2CH(CH_3)$—, —$CH_2CH(CH_3)CH_2$—, —$CH(CH_3)(CH_2)_2$—, —$CH(C_2H_5)CH_2$—, —$CH_2CH(C_2H_5)$—, —$C(CH_3)_2CH_2$—, —$CH_2C(CH_3)_2$—, —$CH(CH_3)CH(CH_3)$, —$CH(C_3H_7)$—, —$(CH_2)_5$, —$(CH_2)_3CH(CH_3)$, —$(CH_2)_2CH(CH_3)CH_2$—, —$CH_2CHCH_3(CH_2)_2$—, —$CH_2C(CH_3)_2CH_2$—, —$(CH_2)_2C(CH_3)_2$—, —$(CH_2)_6$—, —$(CH_2)_4CH(CH_3)$—, —$(CH_2)_3CH(CH_3)CH_2$—, —$CH_2CHCH_3(CH_2)_3$—, —$(CH_2)_3C(CH_3)_2$—, and —$(CH_2)_2C(CH_3)_2CH_2$—.

The term "alkenyl," as used herein, refers to a monovalent straight or branched chain hydrocarbon having from two to six carbons and at least one carbon-carbon double bond.

Representative examples of alkenyl groups include, but are not limited to, —$CH=CH_2$, —$CH=CH—CH_3$, —$CH_2—CH=CH—CH_3$, or —$CH(CH_3)—CH=CH—CH_3$.

The term "alkyl," as used herein, refers to a fully saturated branched or unbranched hydrocarbon moiety. In one embodiment, the alkyl comprises 1 to 20 carbon atoms, 1 to 16 carbon atoms, 1 to 10 carbon atoms, 1 to 6 carbon atoms, or 1 to 4 carbon atoms.

Representative examples of alkyl groups include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

The term "alkynyl," as used herein, refers to a monovalent straight or branched chain hydrocarbon having from two to six carbons and at least one carbon-carbon triple bond.

Representative examples of alkynyl groups include, but are not limited to, 2-propynyl, 3-butynyl, 2-butynyl, 4-pentynyl, 3-pentynyl.

The term "aryl," as used herein, refers to monocyclic, bicyclic or tricyclic aromatic hydrocarbon groups having, for example, from 5 to 14 carbon atoms in the ring portion.

In one embodiment, the aryl refers to monocyclic and bicyclic aromatic hydrocarbon groups having from 6 to 10 carbon atoms. Representative examples of aryl groups include, but are not limited to, phenyl, naphthyl, fluorenyl, and anthracenyl.

The term "arylalkyl," as used herein, refers to an acyclic alkyl group in which one of the hydrogen atoms bonded to a carbon atom, typically a terminal or $sp^3$ carbon atom, is replaced with an aryl group. Representative examples of arylalkyl groups include, but are not limited to, benzyl, 2-phenylethan-1-yl, naphthylmethyl, 2-naphthylethan-1-yl, naphthobenzyl, or 2-naphthophenylethan-1-yl. In certain embodiments, an arylalkyl group is $C_{7-30}$ arylalkyl, e.g., the alkyl moiety of the arylalkyl group is $C_{1-10}$ and the aryl moiety is $C_{6-20}$. In certain embodiments, an arylalkyl group is $C_{6-18}$ is arylalkyl, e.g., the alkyl moiety of the arylalkyl group is $C_{1-8}$ and the aryl moiety is $C_{6-10}$. In certain embodiments, the arylalkyl group is $C_{7-12}$ arylalkyl.

The term "alkyl linker," as used herein, refers to $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. In one embodiment, a $C_{1-6}$ alkyl linker is a $C_1$, $C_2$, $C_3$, $C_4$, $C_5$, or $C_6$ alkyl linker group. Representative examples of alkyl linkers include, but are not limited to, moieties having from one to six carbon atoms, such as, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—), or n-hexyl (—$CH_2CH_2CH_2CH_2CH_2CH_2$—). The term "substituted alkyl linker" refers to alkyl linkers having substituents replacing one or more hydrogen atoms on one or more carbons of the hydrocarbon backbone. Such substituents do not alter the $sp^3$-hybridization of the carbon atom to which they are attached and include those substituents listed below in the definition of the term "substituted."

The term "carbocycle," as used herein, refers to any stable monocyclic, bicyclic or tricyclic ring having the specified number of carbons, any of which may be saturated or unsaturated. In one embodiment, a $C_{3-14}$ carbocycle is intended to include a monocyclic, bicyclic, tricyclic, or spirocyclic (mono- or polycyclic) ring having 3, 4, 5, 6, 7, 8, 9, 10, 11, 12, 13, or 14 carbon atoms. Representative examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantly, tetrahydronaphthyl, octahydropentalene, ocatahydro-1H-indene, bicyclo[2.2.2]octane, spiro[3.4]octane, spiro[4.5]decane, spiro[4.5]deca-1,6-diene, and dispiro[2.2.4.2]dodecane. In one embodiment, the bridge linking to non-adjacent carbon atoms to form a tricyclic ring is a $C_1$ or $C_2$ bridge. When a ring is bridged, the substituents recited for the ring may also be present on the bridge.

The term "cycloalkyl," as used herein, refers to a saturated or partially unsaturated cyclic alkyl group. Representative examples of cycloalkyl groups include, but are not limited to, cyclopropane, cyclobutane, cyclopentane, or cyclohexane. In one embodiment, a cycloalkyl group is $C_{3-15}$ cycloalkyl, $C_{3-12}$ cycloalkyl, or $C_{3-8}$ cycloalkyl.

The term "cycloalkylalkyl," as used herein, refers to an acyclic alkyl group in which one of the hydrogen atoms bonded to a carbon atom, typically a terminal or sp$^3$ carbon atom, is replaced with a cycloalkyl group. In certain embodiments, a cycloalkylalkyl group is $C_{4-30}$ cycloalkylalkyl, and, for example, the alkyl moiety of the cycloalkylalkyl group is $C_{1-10}$ and the cycloalkyl moiety is $C_{3-20}$. In another embodiment, a cycloalkylalkyl group is $C_{3-20}$ cycloalkylalkyl, and, for example, the alkyl moiety of the cycloalkylalkyl group is $C_{1-8}$ and the cycloalkyl moiety is $C_{3-12}$. In a particular embodiment, a cycloalkylalkyl group is $C_{4-12}$ cycloalkylalkyl.

The term "deuterium enrichment factor", as used herein, refers to the ratio between the isotopic abundance and the natural abundance of deuterium in a given sample of a compound.

The term "deuterium incorporation percentage," as used herein, refers to the percentage of the molecules having deuterium at a particular position in a given sample of a compound out of the total amount of the molecules including deuterated and non-deuterated.

The terms "deuterated methyl" and "deuterated ethyl," as used herein, refer to a methyl group and ethyl group, respectively, that contains at least one deuterium atom. Examples of deuterated methyl include —CDH$_2$, —CD$_2$H, and —CD$_3$. Examples of deuterated ethyl include, but are not limited to, —CHDCH$_3$, —CD$_2$CH$_3$, —CHDCDH$_2$, —CH$_2$CD$_3$.

The term "halogen," as used herein, refers to fluoro, choro, bromo, or iodo.

The term "heteroalkyl," as used herein, by itself or as part of another substituent refers to an alkyl group in which one or more of the carbon atoms (and certain associated hydrogen atoms) are independently replaced with heteroatomic groups. Examples of heteroatomic groups include, but are not limited to, —O—, —S—, —O—O—, —S—S—, —O—S—, —NR', =N—N=, —N=N—, —N=N—NR'—, —PR'—, —P(O)$_2$—, —POR'—, —O—P(O)$_2$—, —SO—, —SO$_2$—, and —Sn(R')$_2$—, where each R' is independently hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-15}$ heteroarylalkyl, or substituted $C_{7-18}$ heteroarylalkyl. In one embodiment, $C_{1-6}$ heteroalkyl, means, for example, a $C_{1-6}$ alkyl group in which at least one of the carbon atoms (and certain associated hydrogen atoms) is replaced with a heteroatom. In a particular embodiment, a $C_{1-6}$ heteroalkyl, for example, includes groups having five carbon atoms and one heteroatom, groups having four carbon atoms and two heteroatoms, etc. In one embodiment, each R' is independently hydrogen or $C_{1-3}$ alkyl. In another embodiment, a heteroatomic group is —O—, —S—, —NH—, —N(CH$_3$)—, or —SO$_2$—. In a specific embodiment, the heteroatomic group is —O—.

The term "heteroaryl," as used herein, refers to, for example, a 5-14 membered monocyclic-, bicyclic-, or tricyclic-ring system, having 1 to 10 heteroatoms independently selected from N, O, or S, wherein N and S can be optionally oxidized to various oxidation states, and wherein at least one ring in the ring system is aromatic. In one embodiment, the heteroaryl is monocyclic and has 5 or 6 ring members. Representative examples of monocyclic heteroaryl groups include, but are not limited to, pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Representative examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline, and 6,7-dihydro-5H-pyrrolo[3,2-d]pyrimidine.

The term "heteroarylalkyl," as used herein, refers to an acyclic alkyl group in which one of the hydrogen atoms bonded to a carbon atom, typically a terminal or sp$^3$ carbon atom, is replaced with a heteroaryl group. In certain embodiments, a heteroarylalkyl group is $C_{7-12}$ heteroarylalkyl, and, for example, the alkyl moiety of the heteroarylalkyl group is $C_{1-2}$ and the heteroaryl moiety is $C_{6-10}$.

The term "heterocycle," as used herein, refers to any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

The term "heterocycloalkyl," as used herein, refers to a saturated or unsaturated cyclic alkyl group in which one or more carbon atoms (and certain associated hydrogen atoms) are independently replaced with one or more heteroatoms; or to a parent aromatic ring system in which one or more carbon atoms (and certain associated hydrogen atoms) are independently replaced with one or more heteroatoms such that the ring system no longer contains at least one aromatic ring. Representative examples of heteroatoms to replace the carbon atom(s) include, but are not limited to, N, P, O, S, and Si. Representative examples of heterocycloalkyl groups include, but are not limited to, epoxides, azirines, thiuranes, imidazolidine, morpholine, piperazine, piperidine, pyrazolidine, pyrrolidine, and quinuclidine. In one embodiment, a heterocycloalkyl group is $C_{5-10}$ heterocycloalkyl, $C_{5-8}$ heterocycloalkyl. In a specific embodiment, a heterocycloalkyl group is $C_{5-6}$ heterocycloalkyl.

The term "heterocycloalkylalkyl," as used herein, refers to an acyclic alkyl group in which one of the hydrogen atoms bonded to a carbon atom, typically a terminal or sp$^3$ carbon atom, is replaced with a heterocycloalkyl group. In certain embodiments, a heterocycloalkylalkyl group is $C_{7-12}$ heterocycloalkylalkyl, and, for example, the alkyl moiety of the heterocycloalkylalkyl group is $C_{1-2}$ and the heterocycloalkyl moiety is $C_{6-10}$.

The term "isotopologue," as used herein, refers to an isotopically enriched fumarate.

The term "isotopically enriched," as used herein, refers to an atom having an isotopic composition other than the natural isotopic composition of that atom. In one embodiment, an "isotopically enriched" fumarate contains at least one atom having an isotopic composition other than the natural isotopic composition of that atom.

The term "isotopic composition," as used herein, refers to the amount of each isotope present for a given atom.

The term "pharmaceutically acceptable salt," as used herein, refers to a salt prepared from a pharmaceutically acceptable non-toxic acid or base including an inorganic acid and base and an organic acid and base. Suitable pharmaceutically acceptable base addition salts of the fumarates provided herein include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Others are well known in the art, see for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

The term "stereoisomer" as used herein refers to one stereoisomer of a fumarate that is substantially free of other stereoisomers of that fumarate. For example, a "stereomerically pure" fumarate having one chiral center will be substantially free of the opposite enantiomer of the fumarate. A "stereomerically pure" fumarate having two chiral centers will be substantially free of the other diastereomers of the fumarate. A typical "stereomerically pure" fumarate comprises greater than about 80% by weight of one stereoisomer of the fumarate and less than about 20% by weight of other stereoisomers of the fumarate, greater than about 90% by weight of one stereoisomer of the fumarate and less than about 10% by weight of the other stereoisomers of the fumarate, greater than about 95% by weight of one stereoisomer of the fumarate and less than about 5% by weight of the other stereoisomers of the fumarate, or greater than about 97% by weight of one stereoisomer of the fumarate and less than about 3% by weight of the other stereoisomers of the fumarate. The fumarate can have chiral centers and can occur as racemates, individual enantiomers or diastereomers, and mixtures thereof. All such isomeric forms are included within the embodiments disclosed herein, including mixtures thereof. The use of stereomerically pure forms of such fumarates, as well as the use of mixtures of those forms, are encompassed by the embodiments disclosed herein. For example, mixtures comprising equal or unequal amounts of the enantiomers of a particular fumarate may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley Interscience, New York, 1981); Wilen, S. H., et al., Tetrahedron 33:2725 (1977); Eliel, E. L., Stereochemistry of Carbon Compounds (McGraw Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

The term "substituted," as used herein, refers to a group in which one or more hydrogen atoms are independently replaced with the same or different substituent group(s). In certain embodiments, each substituent group is independently halogen, —OH, —CN, —CF$_3$, =O, —NO$_2$, benzyl, —C(O)NH$_2$, —R", —OR", —C(O)R", —COOR", —S(O)$_2$R" or —NR$_2$" wherein each R" is independently hydrogen or C$_{1-6}$ alkyl. In certain embodiments, each substituent group is independently halogen, —OH, —CN, —CF$_3$, —NO$_2$, benzyl, —R", —OR", or —NR$_2$" wherein each R" is independently hydrogen or C$_{1-4}$ alkyl. In certain embodiments, each substituent group is independently halogen, —OH, —CN, —CF$_3$, =O, —NO$_2$, benzyl, —C(O)NR$_2$", —R", —OR", —C(O)R", —COOR", or —NR$_2$" wherein each R" is independently hydrogen or C$_{1-4}$ alkyl. In certain embodiments, each substituent group is independently —OH, C$_{1-4}$ alkyl, and —NH$_2$.

The number of carbon atoms in a group is specified herein by the prefix "CX-XX", wherein x and xx are integers. For example, "C$_{1-4}$ alkyl" is an alkyl group which has from 1 to 4 carbon atoms; "C$_{1-6}$ alkyl" is an alkyl group having from 1 to 6 carbon atoms; and "C$_{6-10}$ aryl" is an aryl group which has from 6 to 10 carbon atoms.

4. BRIEF DESCRIPTION OF DRAWINGS

FIG. 1 depicts mean ALCs (±SE) over time. ALC=absolute lymphocyte count; SE=standard error; BL=baseline; LLN=lower limit of normal.

Figure 2:
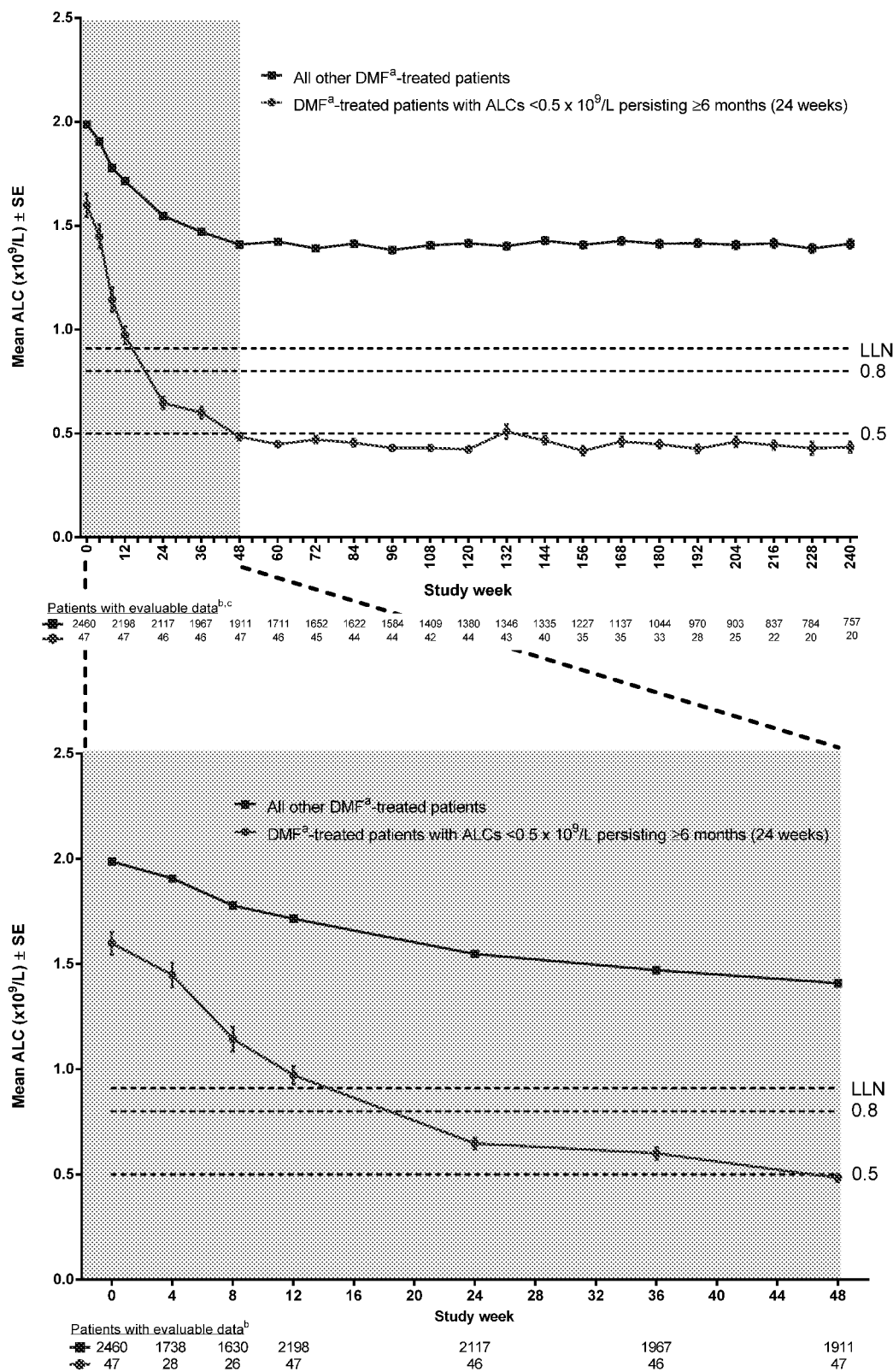

FIG. 2A and FIG. 2B depict mean ALCs over time in patients with ALCs less than 500/mm$^3$ persisting for greater than or equal to 6 months versus all other patients. Shaded area in FIG. 2A is expanded in FIG. 2B. ALC=absolute lymphocyte count; SE=standard error. [a]DMF is delayed-release DMF (also known as gastro-resistant DMF, and as TECFIDERA®). [b]Baseline (Week 0) n includes all patients for whom a baseline ALC value was available. [c]Mean ALCs over time are presented out to approximately 5 years (week 240), as this is the minimum follow-up for patients remaining on study in ENDORSE.

Figure 3:
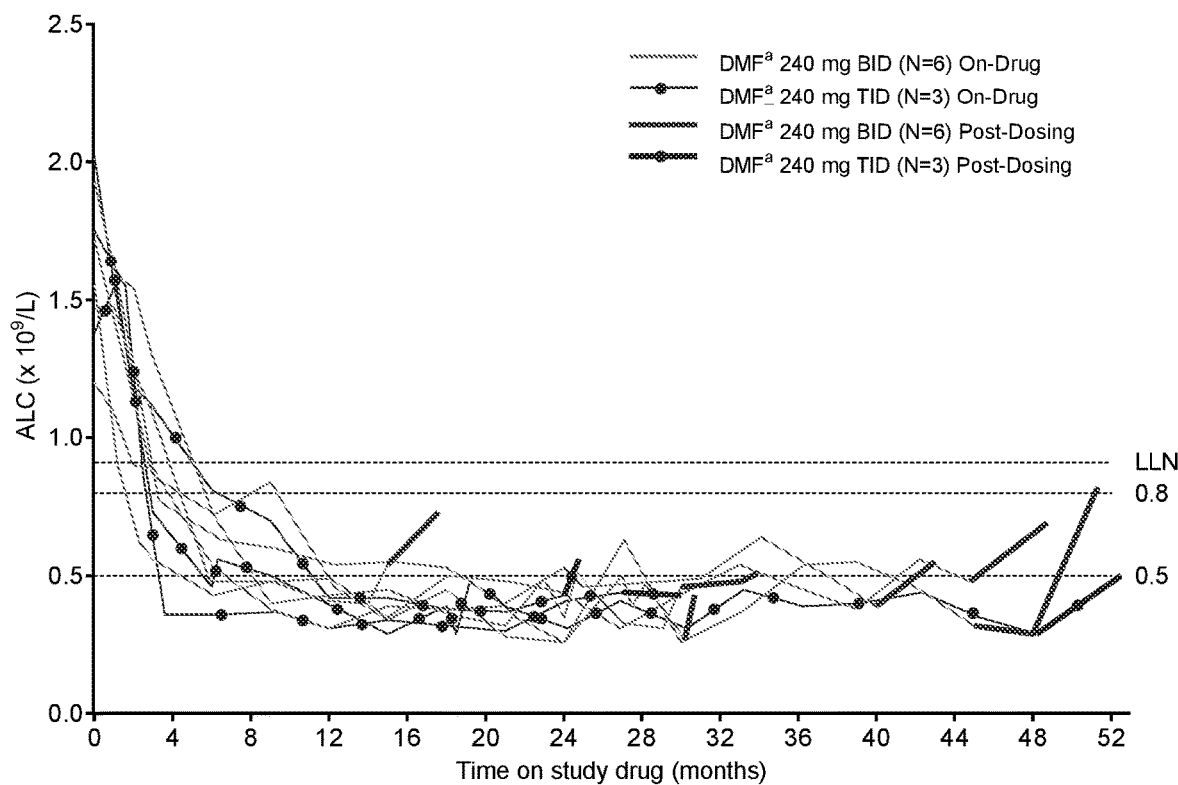

FIG. 3 depicts that ALCs generally increased post-dosing in the 4 weeks following discontinuation of treatment in 9 patients with ALCs less than 500 cells/µL for at least 6 months. ALC=absolute lymphocyte count; BID=twice daily; LLN=lower limit of normal; TID=three timers daily. [a]DMF is delayed-release DMF (also known as gastro-resistant DMF, and as TECFIDERA®).

Figure 4A:
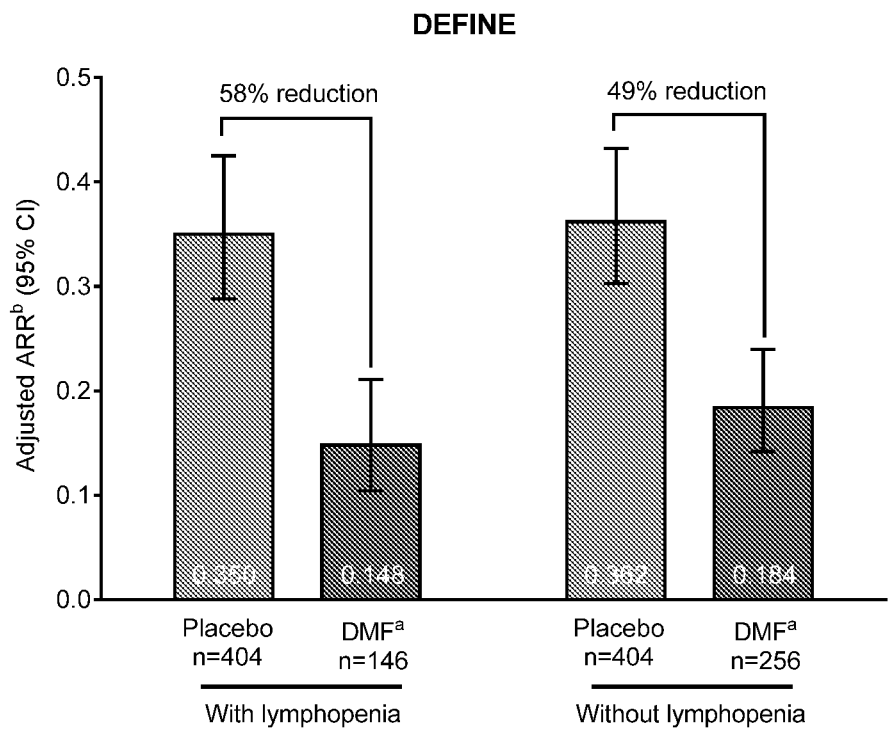
Figure 4B:
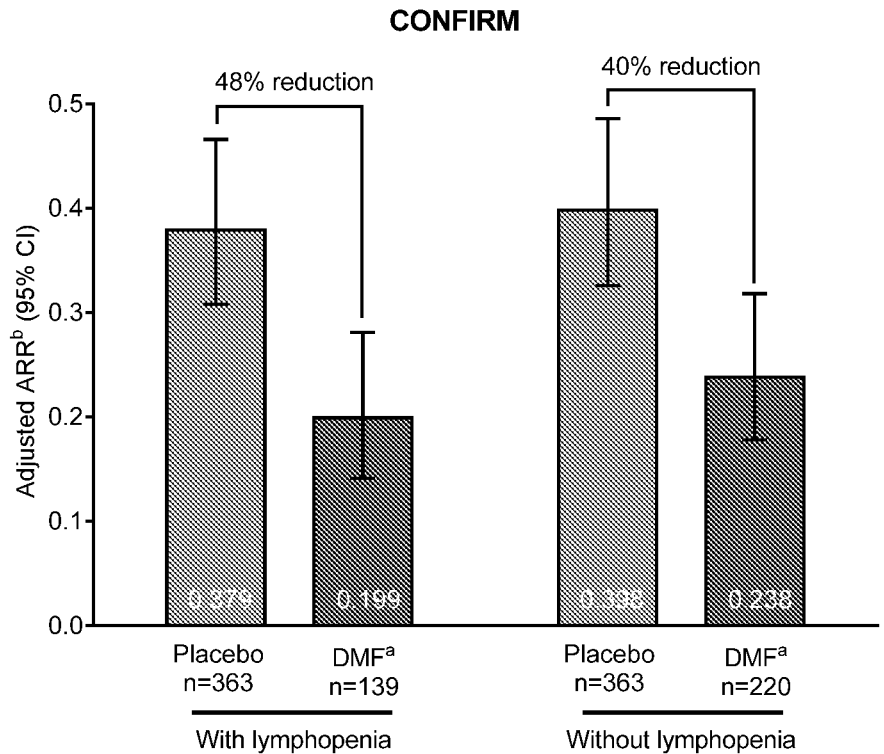

FIGS. 4A-4B depict reduction in ARR at 2 years in DEFINE (FIG. 4A) and CONFIRM (FIG. 4B) in patients in the DMF BID group with lymphopenia (at least 1 ALC less than LLN) or without lymphopenia (all ALCs greater than or equal to LLN) compared with all patients in placebo group. ARR=annualized relapse rate; CI=confidence interval. [a]DMF is delayed-release DMF (also known as gastro-resistant DMF, and as TECFIDERA®). [b]Based on negative binomial regression, adjusted for study, baseline EDSS (≤2.0 vs >2.0), baseline age (<40 vs ≥40), region, and number of relapses in the 1 year prior to study entry.

5. DETAILED DESCRIPTION

The invention provides methods of treating a patient with MS, and improving safety in treatment with MS, based on the recognition of PML as a complication of treatment with the fumarates described herein in some patients. One fatal case of progressive multifocal leukoencephalopathy (PML) occurred in a patient with MS who received TECFIDERA® for 4 years while enrolled in a clinical trial. The patient receiving TECFIDERA® had not previously been treated with immunosuppressive medications or natalizumab, which has a known association with PML, and had no identified systemic medical conditions resulting in compromised immune system function. The patient was also not taking any immunosuppressive or immunomodulatory medications concomitantly. During the clinical trial, the patient experienced prolonged lymphopenia (lymphocyte counts predominantly less than 0.5×10$^9$/L for 3.5 years) while taking TECFIDERA®.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) monitoring the patient for a sign or symptom suggestive of PML in the patient.

Provided herein is a method of improving safety in treatment of a patient with multiple sclerosis comprising monitoring a patient with multiple sclerosis who is being treated with a fumarate for a sign or symptom suggestive of PML in the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) informing the patient that PML has occurred in a patient who received dimethyl fumarate.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a fumarate that PML has occurred in a patient who received dimethyl fumarate, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of improving safety in treatment of a patient with multiple sclerosis comprising instructing a patient with multiple sclerosis who is being treated with a fumarate of the importance of contacting the patient's doctor if the patient develops any symptoms suggestive of PML, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition comprising a fumarate for a sign or symptom suggestive of PML in the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) informing the patient that PML has occurred in a patient who received dimethyl fumarate.

Provided herein is a method of treating a patient with multiple sclerosis comprising (a) administering a pharmaceutical composition comprising fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition comprising a fumarate that PML has occurred in a patient who received dimethyl fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of improving safety in treatment of a patient with multiple sclerosis comprising instructing a patient with multiple sclerosis who is being treated with a pharmaceutical composition comprising a fumarate of the importance of contacting the patient's doctor if the patient develops any symptoms suggestive of PML; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition consisting essentially of dimethyl fumarate and/or monomethyl fumarate to the patient; and (b) monitoring the patient for a sign or symptom suggestive of PML in the patient.

Provided herein is a method of improving safety in treatment of a patient with multiple sclerosis comprising monitoring a patient with multiple sclerosis who is being treated with a pharmaceutical composition consisting essentially of dimethyl fumarate and/or monomethyl fumarate for a sign or symptom suggestive of PML in the patient.

Provided herein is a method of treating a patient with multiple sclerosis comprising (a) administering a pharmaceutical composition consisting essentially of dimethyl fumarate and/or monomethyl fumarate to the patient; and (b) informing the patient that PML has occurred in a patient who received dimethyl fumarate.

Provided herein is a method of treating a patient with multiple sclerosis comprising (a) administering a pharmaceutical composition consisting essentially of dimethyl fumarate and/or monomethyl fumarate to the patient; and (b) instructing the patient of the importance of contacting the patient's doctor if the patient develops any symptoms suggestive of PML.

Provided herein is a method of improving safety in treatment of a patient with multiple sclerosis comprising informing a patient with multiple sclerosis who is being treated with a pharmaceutical composition consisting essentially of dimethyl fumarate and/or monomethyl fumarate that PML has occurred in a patient who received dimethyl fumarate.

Provided herein is a method of improving safety in treatment of a patient with multiple sclerosis comprising instructing a patient with multiple sclerosis who is being treated with a pharmaceutical composition consisting essentially of dimethyl fumarate and/or monomethyl fumarate of the importance of contacting the patient's doctor if the patient develops any symptoms suggestive of PML.

Provided herein is a method of treating a patient with multiple sclerosis comprising (a) administering a fumarate to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) obtaining a complete blood count including lymphocyte count after 6 months of repeated administering of said pharmaceutical composition to said patient, and every 6 to 12 months thereafter. In one embodiment of the foregoing method, the administering is done orally, and the administering is of not greater than 720 mg daily total fumarates. In another embodiment of the foregoing method, the administering is done orally, and the administering is of not greater than 480 mg daily total fumarates.

Provided herein is a method of treating a patient with multiple sclerosis comprising (a) administering a pharmaceutical composition consisting essentially of dimethyl fumarate and/or monomethyl fumarate to the patient; and (b) obtaining a complete blood count including lymphocyte count after 6 months of repeated administering of said pharmaceutical composition to said patient, and every 6 to 12 months thereafter.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a A method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

Provided herein is a A method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition comprising a fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient, wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) repeatedly administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition comprising a fumarate, and who experiences lymphopenia, for signs or symptoms of appearance of new neurological dysfunction; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating multiple sclerosis in a patient who is being treated with a multiple sclerosis disease-modifying therapy other than a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition comprising the fumarate to the patient.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering to the patient of a pharmaceutical composition comprising a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

Provided herein is a method of treating a patient with multiple sclerosis comprising (a) administering a pharmaceutical composition comprising a fumarate to the patient; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition; and (b) prior to the initial administering of the pharmaceutical composition comprising the fumarate to the patient, and periodically during treatment of said patient with said pharmaceutical composition comprising the fumarate, having a blood test done to count the number of white blood cells in the patient; and (c) considering stopping said treatment with said pharmaceutical composition comprising the fumarate if the number of white blood cells decreases during said treatment.

Provided herein is a method of treating a patient with multiple sclerosis comprising (a) prior to initiating treatment of the patient with a pharmaceutical composition consisting essentially of dimethyl fumarate and/or monomethyl fumarate: (i) performing a complete blood count including lymphocyte count; and (ii) if the lymphocyte count is found to be below the normal range, considering alternative causes of lymphopenia, and taking corrective measures as appropriate regarding said alternative causes; and (b) administering said pharmaceutical composition to the patient.

Provided herein is a method of treating a patient with multiple sclerosis comprising (a) repeatedly administering a pharmaceutical composition consisting essentially of dimethyl fumarate and/or monomethyl fumarate to the patient; and (b) obtaining a complete blood count including lymphocyte count every 3 months after starting therapy of said patient with said pharmaceutical composition.

Provided herein is a method of treating a patient with multiple sclerosis comprising (a) administering a pharmaceutical composition consisting essentially of dimethyl fumarate and/or monomethyl fumarate to the patient; and (b) monitoring the patient closely for signs or symptoms of appearance of new neurological dysfunction if the patient experiences lymphopenia after administering of said pharmaceutical composition.

Provided herein is a method of improving safety in treatment of a patient with multiple sclerosis comprising monitoring a patient with multiple sclerosis who is being treated with a pharmaceutical composition consisting essentially of dimethyl fumarate and/or monomethyl fumarate, and who experiences lymphopenia, for signs or symptoms of appearance of new neurological dysfunction.

Provided herein is a method of treating multiple sclerosis in a patient who is being treated with a multiple sclerosis disease-modifying therapy other than a pharmaceutical composition consisting essentially of dimethyl fumarate and/or monomethyl fumarate; said method comprising the following steps in the stated order: (a) stopping administration of said multiple sclerosis disease-modifying therapy to said patient; (b) considering the half-life and mode of action of said multiple sclerosis disease-modifying therapy in order to avoid an additive immune effect whilst at the same time minimizing the risk of disease reactivation; and (c) administering the pharmaceutical composition consisting essentially of dimethyl fumarate and/or monomethyl fumarate.

Provided herein is a method of treating multiple sclerosis in a patient who is being treated with interferon or glatiramer acetate, said method comprising (a) discontinuing administration of interferon or glatiramer acetate to the patient; and (b) immediately after said discontinuing, starting administering a pharmaceutical composition consisting essentially of dimethyl fumarate and/or monomethyl fumarate to the patient.

Provided herein is a method of treating a patient with multiple sclerosis comprising (a) administering a pharmaceutical composition consisting essentially of dimethyl fumarate and/or monomethyl fumarate to the patient; and (b) prior to the initial administering of said pharmaceutical composition to the patient, and periodically during treatment of said patient with said pharmaceutical composition, having a blood test done to count the number of white blood cells in the patient; and (c) considering stopping said treatment with said pharmaceutical composition if the number of white blood cells decreases during said treatment.

All of the various aspects, embodiments, and options disclosed herein can be combined in any and all variations. The compositions and methods provided are exemplary and are not intended to limit the scope of the claimed embodiments.

5.1 Active Agents for Use in the Methods Provided Herein

The active agents (i.e., drugs) for use in the methods and compositions of the invention are fumarates. Such a fumarate can be a dialkyl fumarate (e.g., dimethyl fumarate), a monoalkyl fumarate (e.g., monomethyl fumarate), a combination of dialkyl and monoalkyl fumarates (e.g., dimethyl fumarate and monomethyl fumarate), a prodrug of monoalkyl (e.g., monomethyl) fumarate, a deuterated form of any of the foregoing, or a pharmaceutically acceptable salt, clathrate, solvate, tautomer, or stereoisomer of any of the foregoing, or a combination of any of the foregoing. In one embodiment, the fumarate used in the methods, compositions and products described in this specification is dimethyl fumarate. In a specific embodiment, the fumarate is (i) a monoalkyl fumarate or prodrug thereof, or (ii) a dialkyl fumarate. In one embodiment, the monoalkylfumarate is monomethyl fumarate ("MMF"). In another embodiment, the dialkyl fumarate is dimethyl fumarate ("DMF").

5.1.1 Mono- and Dialkyl Fumarates

In particular, provided herein are mono- and dialkyl fumarates or pharmaceutically acceptable salts, clathrates, solvates, or stereoisomers thereof for use in the methods provided herein.

In one embodiment, the fumarate is a monoalkyl fumarate of Formula I:

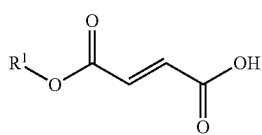

or a pharmaceutically acceptable salt, clathrate, solvate, or stereoisomer thereof, wherein $R^1$ is $C_{1-6}$ alkyl.

In certain embodiments of a compound of Formula (I), $R^1$ is methyl (monomethyl fumarate, "MMF").

In one embodiment, the compounds of Formula I may be prepared using methods known to those skilled in the art, for example, as disclosed in U.S. Pat. No. 4,959,389.

In another embodiment, the fumarate is a dialkyl fumarate of Formula II:

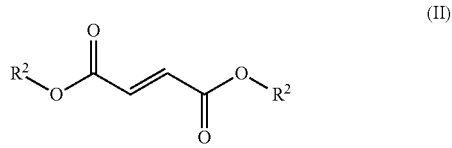

or a pharmaceutically acceptable salt, clathrate, solvate, or stereoisomer thereof, wherein each $R^2$ is independently $C_{1-6}$ alkyl.

In certain embodiments of a compound of Formula (II), each $R^2$ is methyl (dimethyl fumarate, "DMF"). In a specific embodiment, the agent is administered as a pharmaceutical composition, wherein the pharmaceutical composition is TECFIDERA®. In another specific embodiment, the agent is as a pharmaceutical composition, wherein the pharmaceutical composition is FUMADERM®. FUMADERM® comprises of the following active ingredients: dimethyl fumarate, calcium salt of ethyl hydrogen fumarate, magnesium salt of ethyl hydrogen fumarate, and zinc salt of ethyl hydrogen fumarate.

In one embodiment, the compounds of Formula (II) may be prepared using methods known to those skilled in the art, for example, as disclosed in U.S. Pat. No. 4,959,389.

In one embodiment, the fumarate is dimethyl fumarate and/or monomethyl fumarate.

In one embodiment, the fumarate is dimethyl fumarate 5.1.2 Prodrugs of Monoalkyl Fumarates Further provided herein are prodrugs of monoalkyl fumarates or pharmaceutically acceptable salts, clathrates, solvates, or stereoisomers thereof for use in the methods provided herein.

In particular, the prodrugs of monoalkyl fumarates are the prodrugs disclosed in WO2013/119677, such as the compounds of Formula (III):

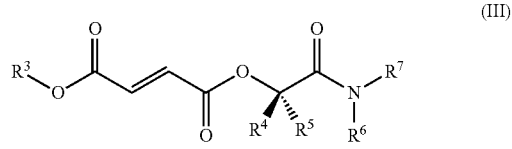

or a pharmaceutically acceptable salt, clathrate, solvate, tautomer, or stereoisomer thereof, $R^3$ is $C_{1-6}$ alkyl;

$R^4$ and $R^5$ are each independently hydrogen, $C_{1-6}$ alkyl, or substituted $C_{1-6}$ alkyl;

$R^6$ and $R^7$ are each independently hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, or substituted $C_{7-12}$ arylalkyl; or $R^6$ and $R^7$ together with the nitrogen to which they are attached form a ring chosen from $C_{5-10}$ heteroaryl, substituted $C_{5-10}$ heteroaryl, $C_{5-10}$ heterocycloalkyl, and substituted $C_{5-10}$ heterocycloalkyl; and wherein each substituent is independently halogen, —OH, —CN, —CF$_3$, =O, —NO$_2$, benzyl, —C(O)NR$^8{}_2$, —R$^8$, —OR$^8$, —C(O)R$^8$, —COOR$^B$, or —NR$^8{}_2$ wherein each $R^8$ is independently hydrogen or $C_{1-4}$ alkyl.

In certain embodiments of a compound of Formula (III), when $R^3$ is ethyl; then $R^6$ and $R^7$ are each independently hydrogen, $C_{1-6}$ alkyl, or substituted $C_{1-6}$ alkyl.

In certain embodiments of a compound of Formula (III), each substituent group is independently halogen, —OH, —CN, —CF$_3$, —R$^8$, —OR$^8$, or —NR$^8{}_2$ wherein each R$^8$ is independently hydrogen or C$_{1-4}$ alkyl. In certain embodiments, each substituent group is independently —OH or —COOH.

In certain embodiments of a compound of Formula (III), each substituent group is independently =O, C$_{1-4}$ alkyl, or —COOR$^8$, wherein R$^8$ is hydrogen or C$_{1-4}$ alkyl.

In certain embodiments of a compound of Formula (III), R$^3$ is methyl.

In certain embodiments of a compound of Formula (III), R$^3$ is ethyl.

In certain embodiments of a compound of Formula (III), R$^3$ is C$_{3-6}$ alkyl.

In certain embodiments of a compound of Formula (III), R$^3$ is methyl, n-propyl, isopropyl, n-butyl, sec-butyl, isobutyl, or tert-butyl.

In certain embodiments of a compound of Formula (III), R$^3$ is methyl, ethyl, n-propyl, isopropyl, n-butyl, sec-butyl, isobutyl, or tert-butyl.

In certain embodiments of a compound of Formula (III), each of R$^4$ and R$^5$ is hydrogen.

In certain embodiments of a compound of Formula (III), one of R$^4$ and R is hydrogen and the other of R$^4$ and R$^5$ is C$_{1-4}$ alkyl.

In certain embodiments of a compound of Formula (III), one of R$^4$ and R$^5$ is hydrogen and the other of R$^4$ and R$^5$ is methyl, ethyl, n-propyl, isopropyl, n-butyl, isobutyl, sec-butyl, or tert-butyl.

In certain embodiments of a compound of Formula (III), one of R$^4$ and R$^5$ is hydrogen and the other of R$^4$ and R$^5$ is methyl.

In certain embodiments of a compound of Formula (III), R$^6$ and R$^7$ are each independently hydrogen or C$_{1-6}$alkyl.

In certain embodiments of a compound of Formula (III), R$^6$ and R$^7$ are each independently hydrogen or C$_{1-4}$ alkyl.

In certain embodiments of a compound of Formula (III), R$^6$ and R$^7$ are each independently hydrogen, methyl, or ethyl.

In certain embodiments of a compound of Formula (III), R$^6$ and R$^7$ are each hydrogen; in certain embodiments, R$^6$ and R$^7$ are each methyl; and in certain embodiments, R$^6$ and R$^7$ are each ethyl.

In certain embodiments of a compound of Formula (III), R$^6$ is hydrogen; and R$^7$ is C$_{1-4}$ alkyl, substituted C$_{1-4}$ alkyl wherein each substituent independently is =O, —OR$^8$, —COOR$^8$, or —NR$^8{}_2$, and wherein each R$^8$ is independently hydrogen or C$_{1-4}$ alkyl.

In certain embodiments of a compound of Formula (III), R$^6$ is hydrogen; and R$^7$ is C$_{1-4}$ alkyl, benzyl, 2-methoxyethyl, carboxymethyl, carboxypropyl, 1,3,4-thiadiazolyl, methoxy, —COOCH$_3$, 2-oxo-1,3-oxazolidinyl, 2-(methylethoxy)ethyl, 2-ethoxyethyl, (tert-butyloxycarbonyl)methyl, (ethoxycarbonyl)methyl, (methylethyl)oxycarbonylmethyl, or ethoxycarbonylmethyl.

In certain embodiments of a compound of Formula (III), R$^6$ and R$^7$ together with the nitrogen to which they are attached form a ring chosen from a C$_{5-6}$ heterocycloalkyl, substituted C$_{5-6}$ heterocycloalkyl, C$_{5-6}$ heteroaryl, and substituted C$_{5-6}$ heteroaryl ring. In certain embodiments of a compound of Formula (III), R$^6$ and R$^7$ together with the nitrogen to which they are attached form a ring chosen from a C$_5$ heterocycloalkyl, substituted C$_5$ heterocycloalkyl, C$_5$ heteroaryl, and substituted C$_5$ heteroaryl ring. In certain embodiments of a compound of Formula (III), R$^6$ and R$^7$ together with the nitrogen to which they are attached form a ring chosen from a C$_6$ heterocycloalkyl, substituted C$_6$ heterocycloalkyl, C$_6$ heteroaryl, and substituted C$_6$ heteroaryl ring. In certain embodiments of a compound of Formula (III), R$^6$ and R$^7$ together with the nitrogen to which they are attached form a ring chosen from piperazine, 1,3-oxazolidinyl, pyrrolidine, and morpholine ring.

In certain embodiments of a compound of Formula (III), R$^6$ and R$^7$ together with the nitrogen to which they are attached form a C$_{5-10}$ heterocycloalkyl ring.

In certain embodiments of a compound of Formula (III), one of R$^4$ and R$^5$ is hydrogen and the other of R$^4$ and R$^5$ is C$_{1-6}$ alkyl; R$^6$ is hydrogen; R$^7$ is hydrogen, C$_{1-6}$ alkyl, or benzyl.

In certain embodiments of a compound of Formula (III), R$^3$ is methyl; one of R$^4$ and R$^5$ is hydrogen and the other of R$^4$ and R$^5$ is C$_{1-6}$ alkyl; R$^6$ is hydrogen; and R$^7$ is hydrogen, C$_{1-6}$ alkyl, or benzyl.

In certain embodiments of a compound of Formula (III), one of R$^4$ and R$^5$ is hydrogen and the other of R$^4$ and R$^5$ is hydrogen or C$_{1-6}$ alkyl; and each of R$^6$ and R$^7$ is C$_{1-6}$ alkyl.

In certain embodiments of a compound of Formula (III), R$^3$ is methyl; one of R$^4$ and R$^5$ is hydrogen and the other of R$^4$ and R$^5$ is hydrogen or C$_{1-6}$ alkyl; and each of R$^6$ and R$^7$ is C$_{1-6}$ alkyl. In certain embodiments of a compound of Formula (III), R$^5$ is methyl; each of R$^4$ and R$^5$ is hydrogen; and each of R$^6$ and R$^7$ is C$_{1-6}$ alkyl.

In certain embodiments of a compound of Formula (III), R$^3$ is methyl; one of R$^4$ and R$^5$ is hydrogen and the other of R$^4$ and R$^5$ is hydrogen or C$_{1-4}$ alkyl; R$^6$ is hydrogen; and R$^7$ is C$_{1-4}$ alkyl or substituted C$_{1-4}$ alkyl wherein the substituent group is =O, —OR$^8$, —COOR$^8$, or —NR$^8{}_2$, wherein each R$^8$ is independently hydrogen or C$_{1-4}$ alkyl. In certain embodiments of a compound of Formula (III), R$^3$ is methyl; one of R$^4$ and R$^5$ is hydrogen and the other of R$^4$ and R$^5$ is methyl; R$^6$ is hydrogen; and R$^7$ is C$_{1-4}$ alkyl or substituted C$_{1-4}$ alkyl wherein the substituent group is =O, —OR$^8$, —COOR$^8$, or —NR$^8{}_2$, wherein each R$^8$ is independently hydrogen or C$_{1-4}$ alkyl. In certain embodiments of a compound of Formula (III), R$^3$ is methyl; each of R$^4$ and R$^5$ is hydrogen; R$^6$ is hydrogen; and R$^7$ is C$_{1-4}$ alkyl or substituted C$_{1-4}$ alkyl wherein the substituent group is =O, —OR$^{11}$, —COOR$^{11}$, or —NR$^{11}{}_2$, wherein each R$^{11}$ is independently hydrogen or C$_{1-4}$ alkyl.

In certain embodiments of a compound of Formula (III), R$^6$ and R$^7$ together with the nitrogen to which they are attached form a C$_{5-10}$ heterocycloalkyl ring.

In certain embodiments of a compound of Formula (III), R$^3$ is methyl; one of R$^4$ and R$^5$ is hydrogen and the other of R$^4$ and R$^5$ is hydrogen or C$_{1-6}$ alkyl; and R$^6$ and R$^7$ together with the nitrogen to which they are attached form a ring chosen from C$_{1-6}$ heterocycloalkyl, substituted C$_{5-6}$ heterocycloalkyl, C$_{5-6}$ heteroaryl, and substituted C$_{5-6}$ heteroaryl ring. In certain embodiments of a compound of Formula (III), R$^3$ is methyl; one of R$^4$ and R$^5$ is hydrogen and the other of R$^4$ and R$^5$ is methyl; R$^6$ and R$^7$ together with the nitrogen to which they are attached form a ring chosen from a C$_{5-6}$ heterocycloalkyl, substituted C$_{1-6}$ heterocycloalkyl, C$_{5-6}$ heteroaryl, and substituted C$_{5-6}$ heteroaryl ring. In certain embodiments of a compound of Formula (III), R$^3$ is methyl; each of R$^4$ and R$^5$ is hydrogen; and R$^6$ and R$^7$ together with the nitrogen to which they are attached form a ring chosen from C$_{1-6}$ heterocycloalkyl, substituted C$_{5-6}$ heterocycloalkyl, C$_{5-6}$ heteroaryl, and substituted C$_{5-6}$ heteroaryl ring.

In certain embodiments of a compound of Formula (III), one of R$^4$ and R$^5$ is hydrogen and the other of R$^4$ and R$^5$ is hydrogen or C$_{1-6}$ alkyl; and R$^6$ and R$^7$ together with the nitrogen to which they are attached form a ring chosen from morpholine, piperazine, and N-substituted piperazine.

In certain embodiments of a compound of Formula (III), $R^3$ is methyl; one of $R^4$ and $R^5$ is hydrogen and the other of $R^4$ and $R^5$ is hydrogen or $C_{1-6}$ alkyl; and $R^6$ and $R^7$ together with the nitrogen to which they are attached form a ring chosen from morpholine, piperazine, and N-substituted piperazine.

In certain embodiments of a compound of Formula (III), $R^3$ is not methyl.

In certain embodiments of a compound of Formula (III), $R^4$ is hydrogen, and in certain embodiments, $R^5$ is hydrogen.

In certain embodiments of a compound of Formula (III), $R^6$ and $R^7$ are independently hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^6$ and $R^7$ together with the nitrogen to which they are attached form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

In certain embodiments of a compound of Formula (III), the compound is:
(N,N-diethylcarbamoyl)methyl methyl(2E)but-2-ene-1,4-dioate;
methyl[N-benzylcarbamoyl]methyl(2E)but-2-ene-1,4-dioate;
methyl 2-morpholin-4-yl-2-oxoethyl(2E)but-2-ene-1,4-dioate;
(N-butylcarbamoyl)methyl methyl(2E)but-2-ene-1,4-dioate;
[N-(2-methoxyethyl)carbamoyl]methyl methyl(2E)but-2-ene-1,4-dioate;
2-{2-[(2E)-3-(methoxycarbonyl)prop-2-enoyloxy]acetylamino}acetic acid;
4-{2-[(2E)-3-(methoxycarbonyl)prop-2-enoyloxy]acetylamino}butanoic acid;
methyl(N-(1,3,4-thiadiazol-2-yl)carbamoyl)methyl(2E)but-2ene-1,4-dioate;
(N,N-dimethylcarbamoyl)methyl methyl(2E)but-2-ene-1,4-dioate;
(N-methoxy-N-methylcarbamoyl)methyl methyl(2E)but-2-ene-1,4-dioate;
bis-(2-methoxyethylamino)carbamoyl]methyl methyl(2E)but-2-ene-1,4-dioate;
[N-(methoxycarbonyl)carbamoyl]methyl methyl(2E)but-2ene-1,4-dioate;
4-{2-[(2E)-3-(methoxycarbonyl)prop-2-enoyloxy]acetylamino}butanoic acid, sodium salt;
methyl 2-oxo-2-piperazinylethyl(2E)but-2-ene-1,4-dioate;
methyl 2-oxo-2-(2-oxo(1,3-oxazolidin-3-yl)ethyl(2E)but-2ene-1,4-dioate;
{N-[2-(dimethylamino)ethyl]carbamoyl}methyl methyl(2E)but-2ene-1,4 dioate;
methyl 2-(4-methylpiperazinyl)-2-oxoethyl(2E)but-2-ene-1,4-dioate;
methyl {N-[(propylamino)carbonyl]carbamoyl}methyl(2E)but-2ene-1,4-dioate;
2-(4-acetylpiperazinyl)-2-oxoethyl methyl(2E)but-2ene-1,4-dioate;
{N,N-bis[2-(methylethoxy)ethyl]carbamoyl}methyl methyl(2E)but-2-ene-1,4-dioate;
methyl 2-(4-benzylpiperazinyl)-2-oxoethyl(2E)but-2-ene-1,4-dioate;

[N,N-bis(2-ethoxyethyl)carbamoyl]methyl methyl(2E)but-2-ene-1,4-dioate;
2-{(2S)-2-[(tert-butyl)oxycarbonyl]pyrrolidinyl}-2-oxoethyl methyl(2E)but-2ene-1,4-dioate;
1-{2-{(2E)-3-(methoxycarbonyl)prop-2-enoyloxy]acetyl} (2S)pyrrolidine-2-carboxylic acid;
(N-{[(tert-butyl)oxycarbonyl]methyl}-N-methylcarbamoyl) methyl methyl(2E)but-2ene-1,4-dioate; {N-(ethoxycarbonyl)methyl]-N-methylcarbamoyl}methyl methyl(2E) but-2-ene-1,4-dioate;
methyl 1-methyl-2-morpholin-4-yl-2-oxoethyl(2E)but-2-ene-1,4-dioate;
[N,N-bis(2-methoxyethyl)carbamoyl]ethyl methyl(2E)but-2-ene-1,4-dioate;
(N,N-dimethylcarbamoyl)ethyl methyl(2E)but-2-ene-1,4-dioate;
2-{2-[(2E)-3-(methoxy carbonyl)prop-2-enoyloxyl]-N-methylacetylamino}acetic acid;
(N-{[(tert-butyl)oxycarbonyl]methyl}carbamoyl)methyl methyl(2E)but-2-ene-1,4-dioate;
(2E)but-methyl-N-{[(methylethyl)oxycarbonyl] methyl}carbamoyl)methyl(2E)but-2-ene-1,4-dioate; {N-[(ethoxycarbonyl)methyl]-N-benzylcarbamoyl}methyl methyl(2E)but-2-ene-1,4-dioate;
{N-[(ethoxycarbonyl)methyl]-N-benzylcarbamoyl}ethyl methyl(2E)but-2-ene-1,4-dioate;
{N-[(ethoxycarbonyl)methyl]-N-methylcarbamoyl}ethyl methyl(2E)but-2-ene-1,4-dioate;
(1S)-1-methyl-2-morpholin-4-yl-2-oxo ethyl methyl(2E) but-2-ene-1,4-dioate;
(1S)-1-[N,N-bis(2-methoxyethyl)carbamoyl]ethyl methyl (2E)but-2-ene-1,4-dioate;
(1R)-1-(N,N-diethylcarbamoyl)ethyl methyl(2E)but-2-ene-1,4-dioate; or
(1S)-1-(N,N-diethylcarbamoyl)ethyl methyl(2E)but-2-ene-1,4-dioate; or a pharmaceutically acceptable salt, clathrate, solvate, tautomer, or stereoisomer thereof.

In certain embodiments of a compound of Formula (III), the compound is:

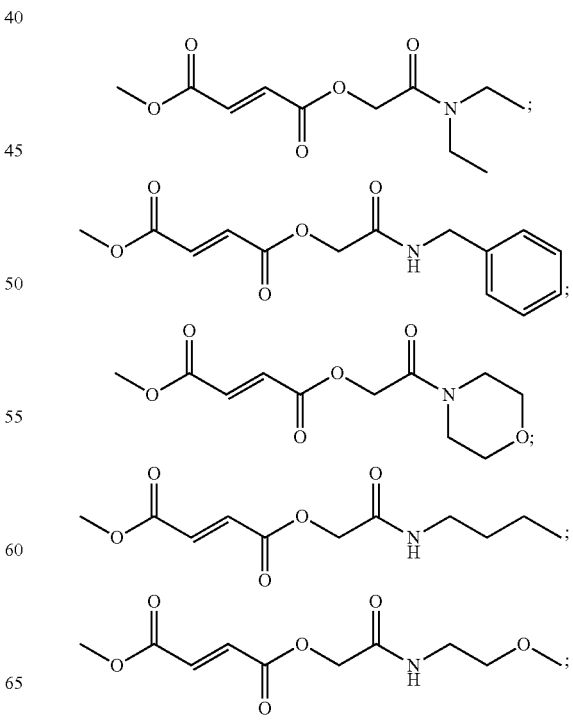

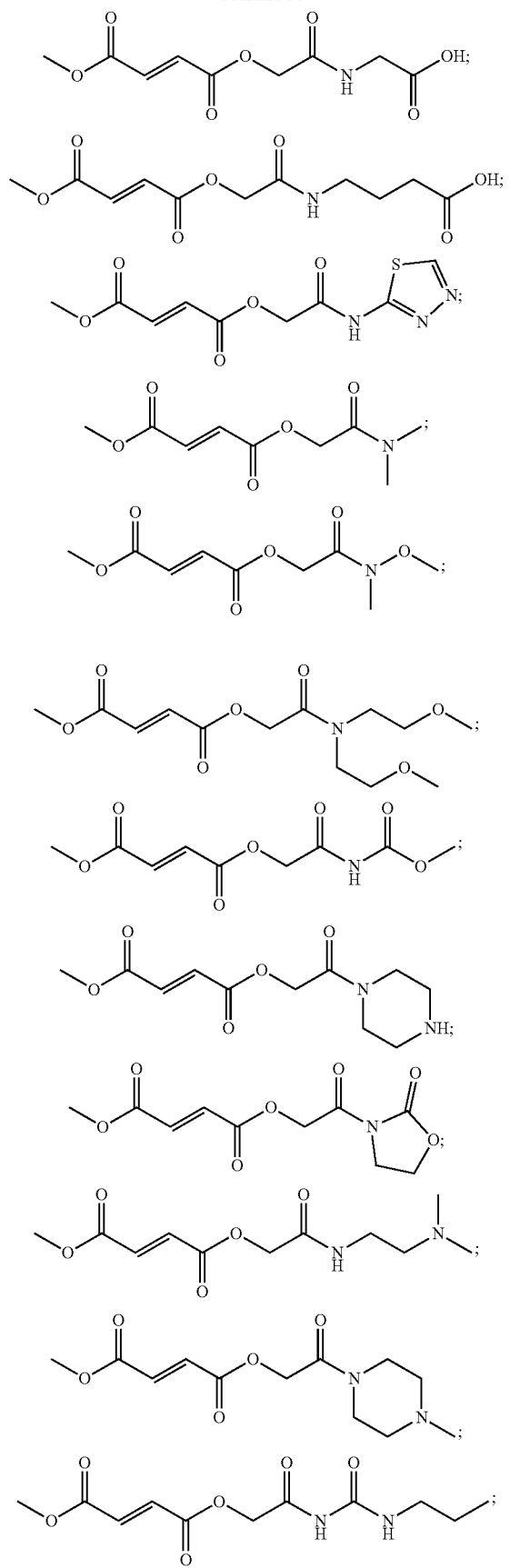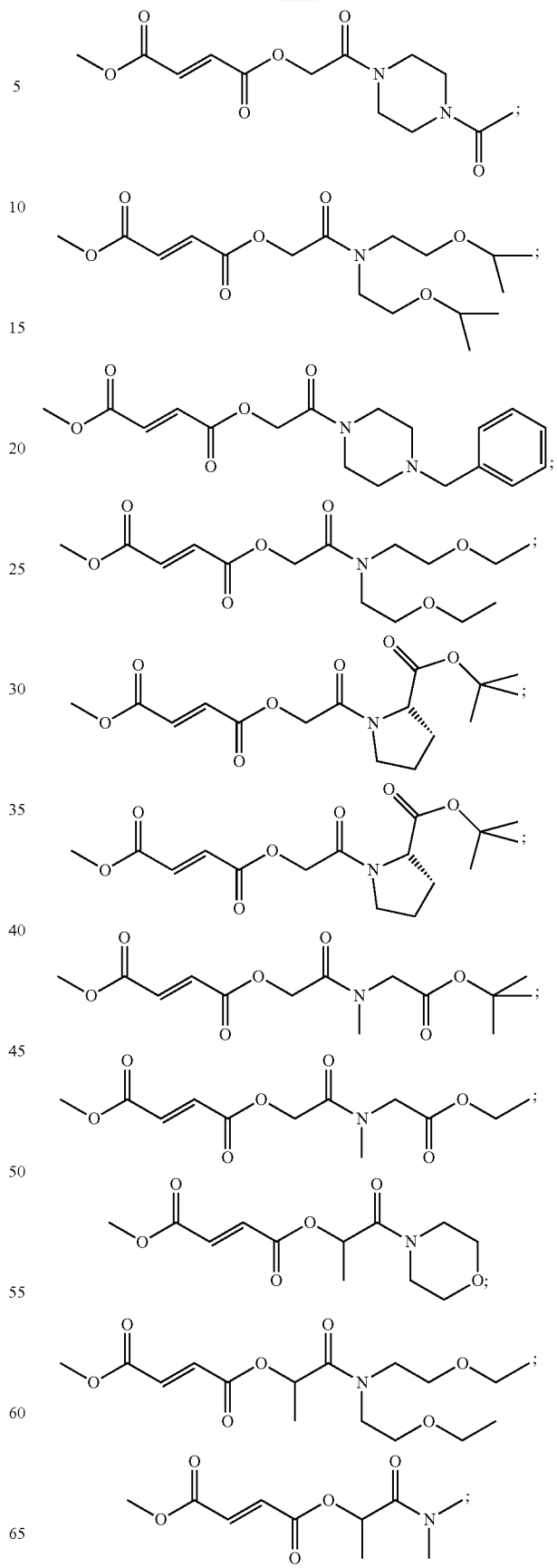

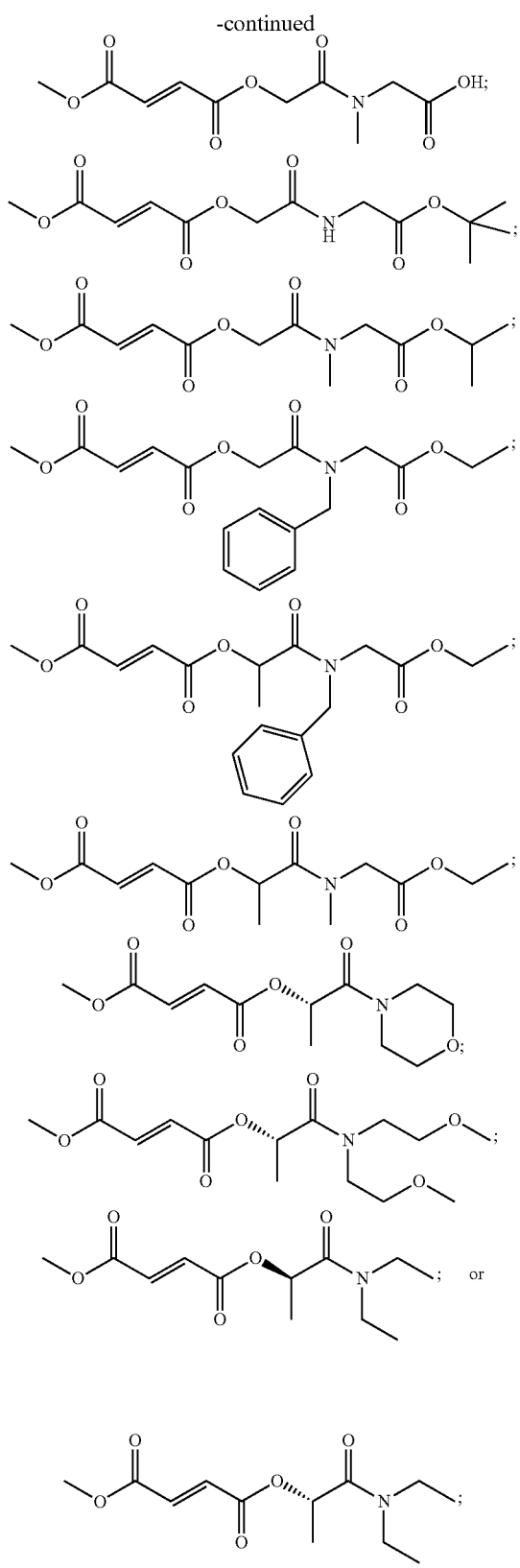

or a pharmaceutically acceptable salt, clathrate, solvate, tautomer, or stereoisomer thereof.

In certain embodiments of a compound of Formula (III), the compound is:

(N,N-diethylcarbamoyl)methyl methyl(2E)but-2-ene-1,4-dioate;
methyl[N-benzylcarbamoyl]methyl(2E)but-2-ene-1,4-dioate; methyl 2-morpholin-4-yl-2-oxoethyl(2E)but-2-ene-1,4-dioate;
(N-butylcarbamoyl)methyl methyl(2E)but-2-ene-1,4-dioate;
[N-(2-methoxyethyl)carbamoyl]methyl methyl(2E)but-2-ene-1,4-dioate;
2-{2-[(2E)-3-(methoxycarbonyl)prop-2-enoyloxy]acetylamino}acetic acid;
{2-[(2E)-3-(methoxycarbonyl)prop-2-enoyloxy]acetylamino}butanoic acid;
methyl(N-(1,3,4-thiadiazol-2-yl)carbamoyl)methyl(2E)but-2ene-1,4-dioate;
(N,N-dimethylcarbamoyl)methyl methyl(2E)but-2-ene-1,4-dioate;
(N-methoxy-N-methylcarbamoyl)methyl methyl(2E)but-2-ene-1,4-dioate;
bis-(2-methoxyethylamino)carbamoyl]methyl methyl(2E)but-2-ene-1,4-dioate;
[N-(methoxycarbonyl)carbamoyl]methyl methyl(2E)but-2ene-1,4-dioate;
methyl 2-oxo-2-piperazinylethyl(2E)but-2-ene-1,4-dioate;
methyl 2-oxo-2-(2-oxo(1,3-oxazolidin-3-yl)ethyl(2E)but-2ene-1,4-dioate;
{N-[2-(dimethylamino)ethyl]carbamoyl}methyl methyl(2E)but-2ene-1,4-dioate;
(N-[(methoxycarbonyl)ethyl]carbamoyl)methyl methyl(2E)but-2-ene-1,4-dioate; or
2-{2-[(2E)-3-(methoxycarbonyl)prop-2-enoyloxy]acetylamino}propanoic acid; or a
pharmaceutically acceptable salt, clathrate, solvate, tautomer, or stereoisomer thereof.

In certain embodiments of a compound of Formula (III), the compound is:

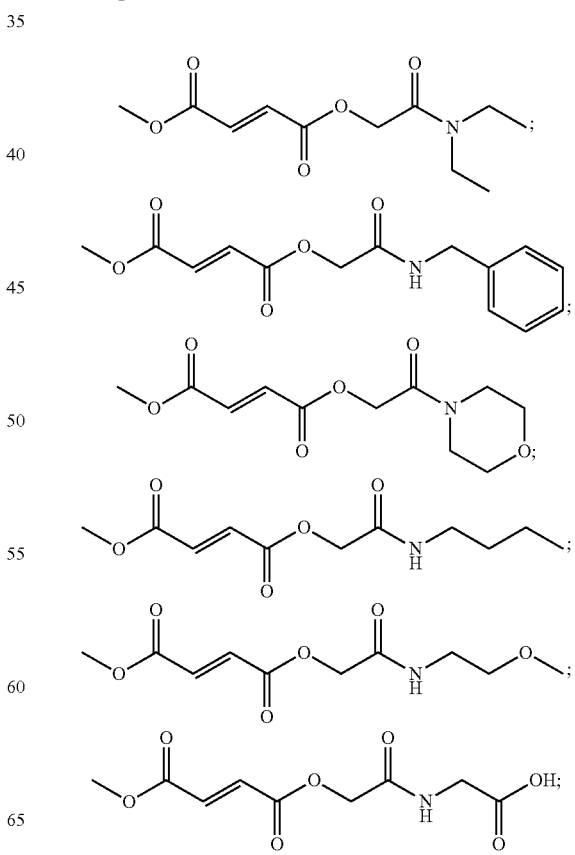

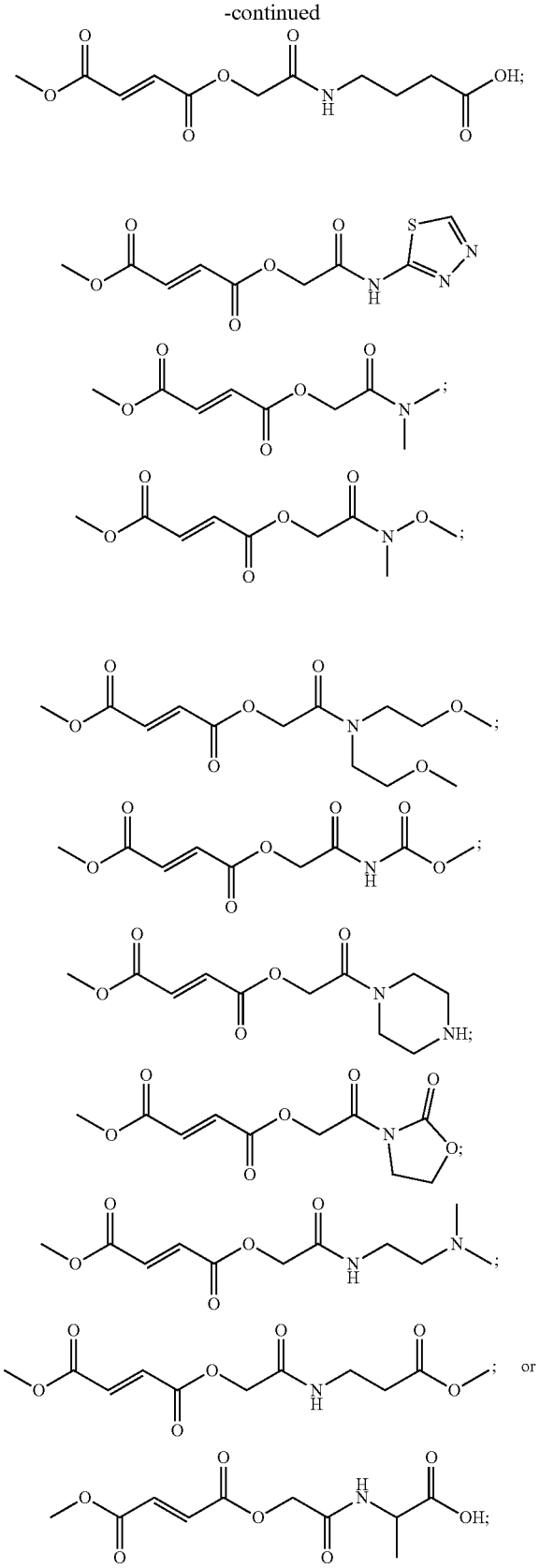

or a pharmaceutically acceptable salt, clathrate, solvate, tautomer, or stereoisomer thereof.

In certain embodiments of a compound of Formula (III), the compound is:

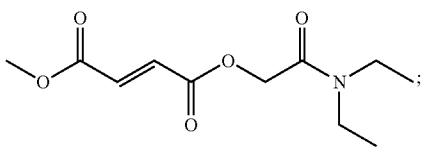 [SMILES: CCN(CC)C(=O)COC(=O)/C=C/C(=O)OC]

or a clathrate or solvate thereof. In a particular embodiment,

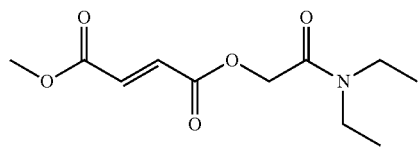 [SMILES: CCN(CC)C(=O)COC(=O)/C=C/C(=O)OC]

may be administered as a cocrystal in the methods provided herein. In certain embodiments, the cocrystals are cocrystals with urea, fumaric acid, succinic acid, maleic acid, malic acid, or citric acid or those disclosed in US patent application publication number US 2014-0179778 A1.

In certain embodiments of a compound of Formula (III), the compound is:

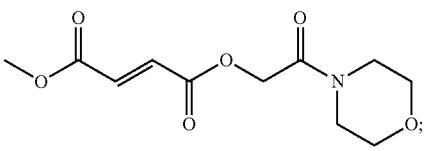 [SMILES: COC(=O)/C=C/C(=O)OCC(=O)N1CCOCC1]

or a clathrate or solvate thereof.

In certain embodiments of a compound of Formula (III), the compound is:

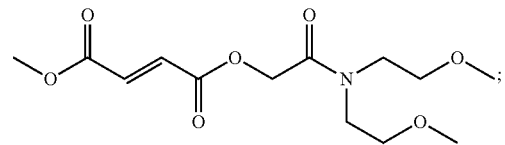

or a clathrate or solvate thereof.

In certain embodiments of a compound of Formula (II), the compound is:

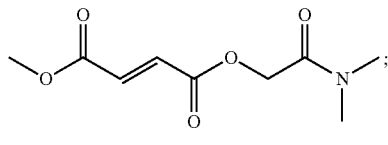

or a clathrate or solvate thereof.

The compounds recited above were named using Chemistry 4-D Draw Pro, Version 7.01c (ChemInnovation Software, Inc., San Diego, Calif.).

In one embodiment, the compounds of Formula (III) may be prepared using methods known to those skilled in the art, for example, as disclosed in U.S. Pat. No. 8,148,414 B2.

In one embodiment, the prodrugs of monoalkyl fumarates are the prodrugs disclosed in WO2013/119677, such as the compounds of Formula (IV):

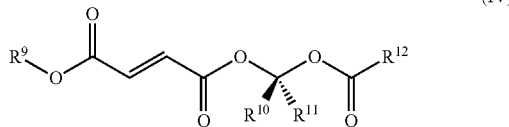
(IV)

or a pharmaceutically acceptable salt, clathrate, solvate, tautomer, or stereoisomer thereof, wherein $R^9$ is $C_{1-6}$ alkyl;

$R^{10}$ and $R^{11}$ are each independently hydrogen, $C_{1-6}$ alkyl, or substituted $C_{1-6}$ alkyl; and $R^{12}$ is $C_{1-6}$ alkyl, substituted $C_{1-6}$ alkyl, $C_{1-6}$ alkenyl, substituted $C_{1-6}$ alkenyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, or —$OR^{13}$ wherein $R^1$ is $C_{1-6}$ alkyl, substituted $C_{1-6}$ alkyl, $C_{3-10}$ cycloalkyl, substituted $C_{3-10}$ cycloalkyl, $C_{6-10}$ aryl, or substituted $C_{6-10}$ aryl;

wherein each substituent is independently halogen, —OH, —CN, —$CF_3$, =O, —$NO_2$, benzyl, —C(O)$NR^{14}_2$, —$R^4$, —$OR"$, —C(O)$R^{14}$, —$COOR^{14}$, or —$NR^{14}_2$ wherein each $R^4$ is independently hydrogen or $C_{1-4}$ alkyl.

In certain embodiments of a compound of Formula (IV), each substituent is independently halogen, —OH, —CN, —$CF_3$, —$R^{14}$, —$OR^4$, or —$NR^{14}_2$ wherein each $R^{14}$ is independently hydrogen or $C_{1-4}$ alkyl.

In certain embodiments of a compound of Formula (IV), each substituent is independently =O, $C_{1-4}$ alkyl, and —$COOR^{14}$ wherein $R^{14}$ is hydrogen or $C_4$ alkyl.

In certain embodiments of a compound of Formula (IV), $R^9$ is $C_{1-6}$ alkyl; in certain embodiments, $R^9$ is $C_{1-3}$ alkyl; and in certain embodiments, $R^9$ is methyl or ethyl.

In certain embodiments of a compound of Formula (IV), $R^9$ is methyl.

In certain embodiments of a compound of Formula (IV), $R^9$ is ethyl, n-propyl, isopropyl, n-butyl, sec-butyl, isobutyl, or tert-butyl.

In certain embodiments of a compound of Formula (IV), $R^9$ is methyl, ethyl, n-propyl, isopropyl, n-butyl, isobutyl, or tert-butyl.

In certain embodiments of a compound of Formula (IV), one of $R^{10}$ and $R^{11}$ is hydrogen and the other of $R^{10}$ and $R^{11}$ is $C_{1-6}$ alkyl. In certain embodiments of a compound of Formula (IV), one of $R^{10}$ and $R^{11}$ is hydrogen and the other of $R^{10}$ and $R^{11}$ is $C_{1-4}$ alkyl.

In certain embodiments of a compound of Formula (IV), one of $R^{10}$ and $R^{11}$ is hydrogen and the other of $R^{10}$ and $R^{11}$ is methyl, ethyl, n-propyl, or isopropyl. In certain embodiments of a compound of Formula (IV), each of $R^{10}$ and $R^{11}$ is hydrogen.

In certain embodiments of a compound of Formula (IV), $R^{12}$ is $C_{1-6}$ alkyl; one of $R^{10}$ and $R^{11}$ is hydrogen and the other of $R^{10}$ and $R^{11}$ is $C_{1-6}$ alkyl; and $R^9$ is $C_{1-6}$ alkyl.

In certain embodiments of a compound of Formula (IV), $R^{12}$ is —$OR^{13}$.

In certain embodiments of a compound of Formula (IV), $R^{13}$ is $C_{1-4}$ alkyl, cyclohexyl, or phenyl.

In certain embodiments of a compound of Formula (IV), $R^{12}$ is methyl, ethyl, n-propyl, or isopropyl; one of $R^{10}$ and $R^{11}$ is hydrogen and the other of $R^{10}$ and $R^{11}$ is methyl, ethyl, n-propyl, or isopropyl.

In certain embodiments of a compound of Formula (IV), $R^{12}$ is substituted $C_{1-2}$ alkyl, wherein each substituent is independently —COOH, —NHC(O)$CH_2NH_2$, or —$NH_2$.

In certain embodiments of a compound of Formula (IV), $R^{12}$ is ethoxy, methylethoxy, isopropyl, phenyl, cyclohexyl, cyclohexyloxy, —CH($NH_2$)$CH_2$COOH, —$CH_2$CH($NH_2$)COOH,
—CH(NHC(O)$CH_2NH_2$)—$CH_2$COOH, or —$CH_2$CH(NHC(O)$CH_2NH_2$)—COOH.

In certain embodiments of a compound of Formula (IV), $R^9$ is methyl or ethyl; one of $R^{10}$ and $R^{11}$ is hydrogen and the other of $R^{10}$ and $R^{11}$ is hydrogen, methyl, ethyl, n-propyl, or isopropyl; and $R^1$ is $C_{1-3}$ alkyl, substituted $C_{1-2}$ alkyl wherein each substituent group is —COOH, —NHC(O)$CH_2NH_2$, —$NH_2$, or —$OR^{13}$ wherein $R^{13}$ is $C_{1-3}$ alkyl, cyclohexyl, phenyl, or cyclohexyl.

In certain embodiments of a compound of Formula (IV), the compound is: ethoxycarbonyloxyethyl methyl(2E)but-2-ene-1,4-dioate; methyl(methylethoxycarbonyloxy)ethyl (2E)but-2-ene-1,4-dioate; or (cyclohexyloxycarbonyloxy) ethyl methyl(2E)but-2-ene-1,4-dioate; or a clathrate, solvate, or stereoisomer thereof.

In certain embodiments of a compound of Formula (IV), the compound is:

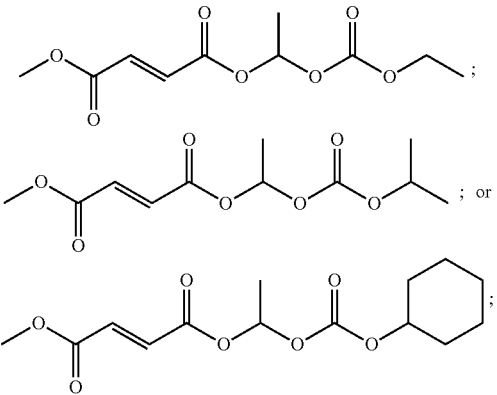

or a clathrate, solvate, or stereoisomer thereof.

In certain embodiments of a compound of Formula (IV), the compound is:

methyl(2-methylpropanoyloxy)ethyl(2E)but-2-ene-1,4-dioate;

methyl phenylcarbonyloxyethyl(2E)but-2-ene-1,4-dioate;

cyclohexylcarbonyloxybutyl methyl(2E)but-2-ene-1,4-dioate;

[(2E)-3-(methoxycarbonyl)prop-2-enoyloxy]ethyl methyl (2E)but-2-ene-1,4-dioate; or methyl 2-methyl-1-phenylcarbonyloxypropyl(2E)but-2-ene-1,4-dioate; or a clathrate, solvate, or stereoisomer thereof.

In certain embodiments of a compound of Formula (IV), the compound is:

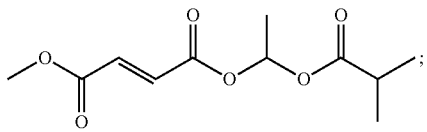

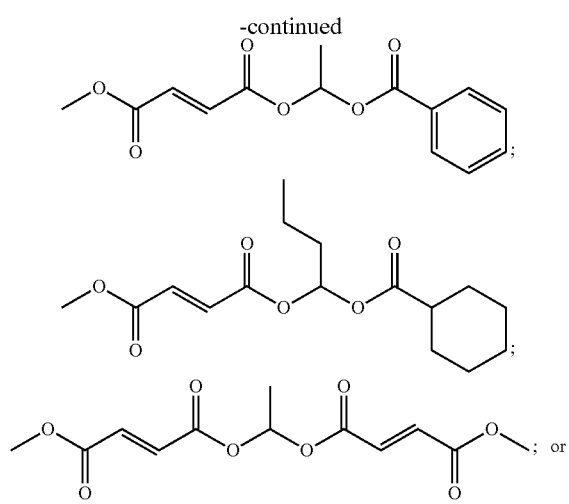

or a clathrate, solvate, or stereoisomer thereof.

In certain embodiments of a compound of Formula (IV), the compound is:
ethoxycarbonyloxyethyl methyl(2E)but-2-ene-1,4-dioate;
methyl(methylethoxycarbonyloxy)ethyl(2E)but-2-ene-1,4-dioate;
methyl(2-methylpropanoyloxy)ethyl(2E)but-2-ene-1,4-dioate;
methyl phenylcarbonyloxyethyl(2E)but-2-ene-1,4-dioate;
cyclohexylcarbonyloxybutyl methyl(2E)but-2-ene-1,4-dioate;
[(2E)-3-(methoxycarbonyl)prop-2-enoyloxy]ethyl methyl (2E)but-2-ene-1,4-dioate;
(cyclohexyloxycarbonyloxy)ethyl methyl(2E)but-2-ene-1,4-dioate;
methyl 2-methyl-1-phenylcarbonyloxypropyl(2E)but-2-ene-1,4-dioate; or a clathrate, solvate, or stereoisomer thereof.

In certain embodiments of a compound of Formula (IV), the compound is:
3-({[(2E)-3-(methoxycarbonyl)prop-2-enoyloxy] methyl}oxycarbonyl)(3S)-3-aminopropanoic acid, 2,2,2-trifluoroacetic acid;
3-({[(2E)-3-(methoxycarbonyl)prop-2-enoyloxy] methyl}oxycarbonyl)(2S)-2-aminopropanoic acid, 2,2,2-trifluoroacetic acid;
3-({[(2E)-3-(methoxycarbonyl)prop-2-enoyloxy] methyl}oxycarbonyl)(3S)-3-(2-aminoacetylamino)propanoic acid, 2,2,2-trifluoroacetic acid; or
3-{[(2E)-3-(methoxycarbonyl)prop-2enoyloxy]ethoxycarbonyloxy}(2S)-2-aminopropanoic acid, chloride; or a clathrate, solvate, or stereoisomer thereof.

In certain embodiments of a compound of Formula (IV), the compound is:

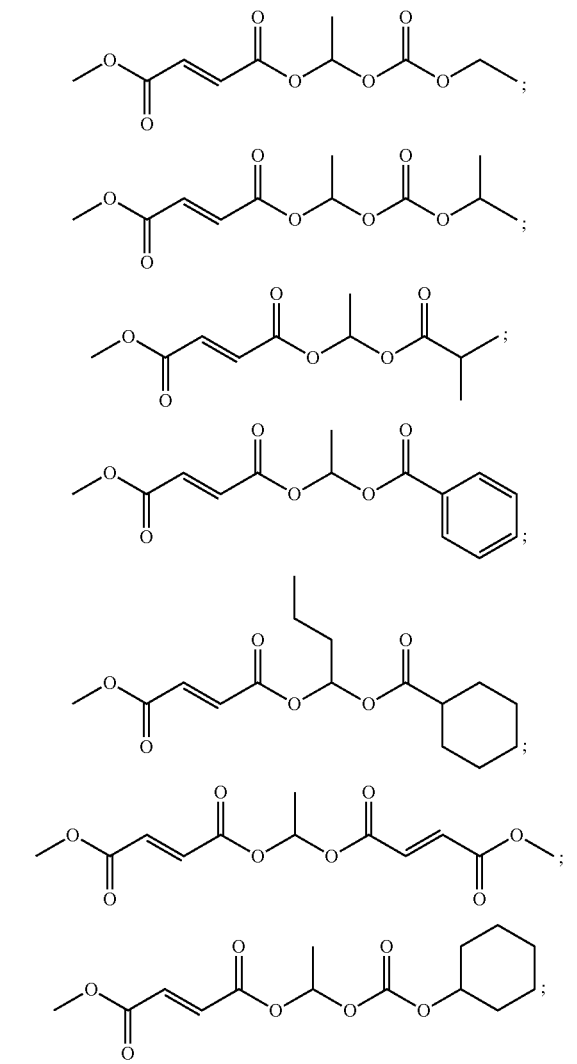

or a clathrate solvate, or stereoisomer thereof.

In certain embodiments of a compound of Formula (IV), the compound is:

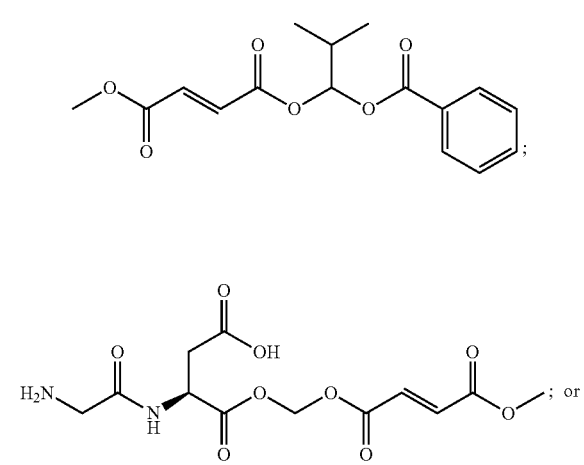

-continued

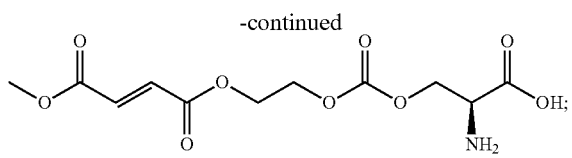

or a pharmaceutically acceptable salt, clathrate, solvate, or stereoisomer thereof.

In certain embodiments of a compound of Formula (IV), the compound is:

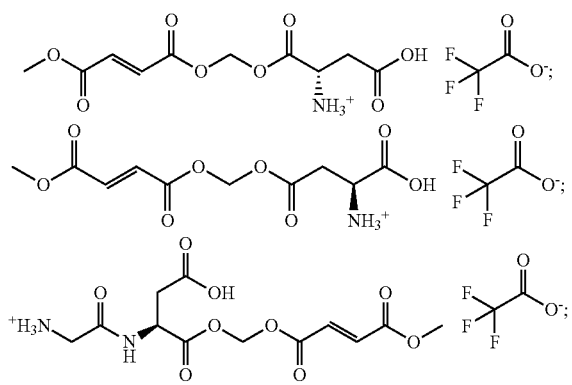

or

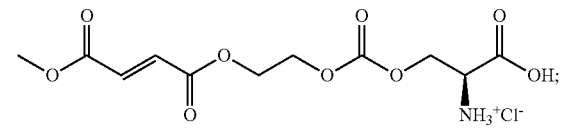

a clathrate, solvate, or stereoisomer thereof.

The compounds recited above were named using Chemistry 4-D Draw Pro, Version 7.01c (ChemInnovation Software, Inc., San Diego, Calif.).

In one embodiment, the compounds of Formula (IV) may be prepared using methods known to those skilled in the art, for example, as disclosed in U.S. Pat. No. 8,148,414 B2.

In one embodiment, the prodrugs of monoalkyl fumarates are the prodrugs disclosed in U.S. Patent Application Publication No. 2014/0057918, such as the compounds of Formula (V):

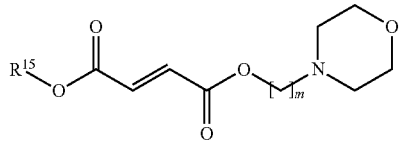

(V)

or a pharmaceutically acceptable salt, clathrate, or solvate thereof, wherein
$R^{15}$ is $C_{1-6}$ alkyl; and
m is an integer from 2 to 6.

In certain embodiments of a compound of Formula (V), $R^{15}$ is methyl.

In certain embodiments of a compound of Formula (V), $R^{15}$ is ethyl.

In certain embodiments of a compound of Formula (V), $R^{15}$ is $C_{3-6}$ alkyl.

In certain embodiments of a compound of Formula (V), $R^{15}$ is methyl, n-propyl, isopropyl, n-butyl, sec-butyl, isobutyl, or tert-butyl.

In certain embodiments of a compound of Formula (V), $R^{15}$ is methyl, ethyl, n-propyl, isopropyl, n-butyl, sec-butyl, isobutyl, or tert-butyl.

In certain embodiments of a compound of Formula (V), the compound is:
methyl (2-morpholinoethyl)fumarate;
methyl (3-morpholinopropyl)fumarate;
methyl (4-morpholinobutyl)fumarate;
methyl (5-morpholinopentyl)fumarate; or
methyl (6-morpholinohexyl)fumarate;
or a pharmaceutically acceptable salt, clathrate, or solvate thereof.

In certain embodiments of a compound of Formula (V), the compound is:

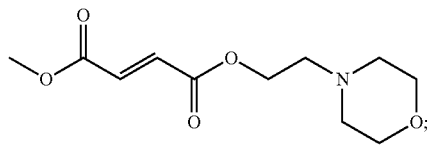

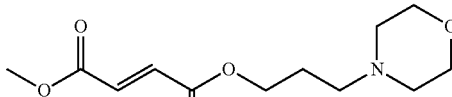

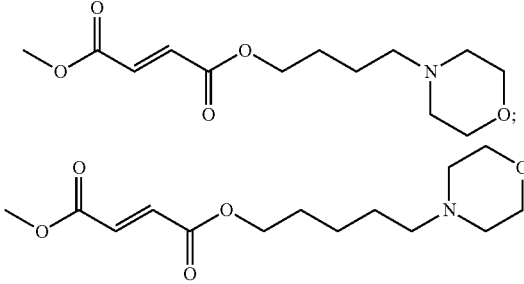

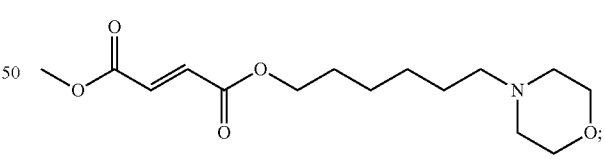

or a pharmaceutically acceptable salt, clathrate, or solvate thereof.

The compounds recited above were named using Chemistry 4-D Draw Pro, Version 7.01c (ChemInnovation Software, Inc., San Diego, Calif.).

In one embodiment, the compounds of Formula (V) may be prepared using methods known to those skilled in the art, for example, as disclosed in U.S. Patent Application Publication No. 2014/0057918.

In one embodiment, the prodrugs of monoalkyl fumarates are the prodrugs disclosed in WO2013/119677, such as the compounds of Formula (VI):

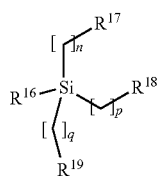
(VI)

or a pharmaceutically acceptable salt, clathrate, solvate, or stereoisomer thereof, wherein:

$R^{16}$ is $C_{1-10}$ alkyl, $C_{5-14}$ aryl, hydroxyl, —O—$C_{1-10}$ alkyl, or —O—$C_{5-14}$ aryl;

each of $R^{17}$, $R^{18}$, and $R^{19}$ independently is $C_{1-10}$ alkyl, $C_{5-14}$ aryl, hydroxyl, —O—$C_{1-10}$ alkyl, —O—$C_{5-14}$ aryl, or

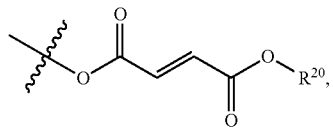

wherein $R^{20}$ is $C_{1-6}$ alkyl; each of which can be optionally substituted; and each of n, p, and q independently is 0-4;
provided that at least one of $R^{17}$, $R^{18}$, and $R^{19}$ is

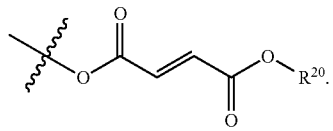

In certain embodiments of a compound of Formula (VI), $R^{20}$ is optionally substituted $C_{1-6}$ alkyl. In certain embodiments of a compound of Formula (VI), $R^{20}$ is optionally substituted methyl, ethyl, or isopropyl. In certain embodiments of a compound of Formula (VI), $R^{20}$ is methyl.

In certain embodiments of a compound of Formula (VI), $R^{16}$ is $C_{1-10}$ alkyl. In certain embodiments of a compound of Formula (VI), $R^{16}$ is optionally substituted $C_{1-6}$ alkyl. In certain embodiments of a compound of Formula (VI), $R^{16}$ is optionally substituted methyl, ethyl, or isopropyl. In certain embodiments of a compound of Formula (VI), $R^{16}$ is optionally substituted $C_{5-15}$ aryl. In certain embodiments of a compound of Formula (VI), $R^{16}$ is optionally substituted $C_5$-$C_{10}$ aryl.

In one embodiment, the prodrugs of monoalkyl fumarates are the prodrugs disclosed in WO2013/119677, such as the compounds of Formula (VI'):

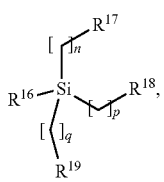
(VI)

or a pharmaceutically acceptable salt, clathrate, solvate, or stereoisomer thereof, wherein $R^{16}$ is $C_{1-10}$ alkyl, $C_{6-10}$ aryl, hydroxyl, —O—$C_{1-10}$ alkyl, or —O—$C_{6-10}$ aryl;

each of $R^{17}$, $R^{18}$, and $R^{19}$ independently is $C_{1-10}$ alkyl, $C_{6-10}$ aryl, hydroxyl, —O—$C_{1-10}$ alkyl, —O—$C_{6-10}$ aryl, or

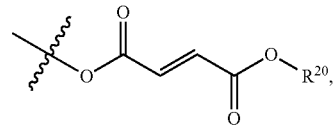

wherein $R^{20}$ is $C_{1-6}$ alkyl; each of which can be optionally substituted; and each of n, p, and q independently is 0-4;
provided that at least one of $R^{17}$, $R^{18}$, and $R^{19}$ is

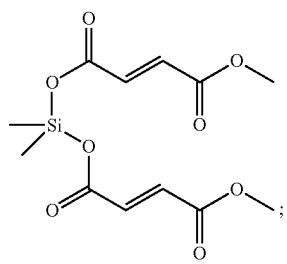

In certain embodiments of a compound of Formula (VI'), $R^{20}$ is methyl.

In certain embodiments of a compound of Formula (VI) or Formula (VI'), the compound is: (dimethylsilanediyl) dimethyl difumarate; methyl ((trimethoxysilyl)methyl) fumarate; methyl ((trihydroxysilyl)methyl) fumarate; or trimethyl (methylsilanetriyl) trifumarate; or a pharmaceutically acceptable salt thereof.

In certain embodiments of a compound of Formula (VI) or Formula (VI'), the compound is:

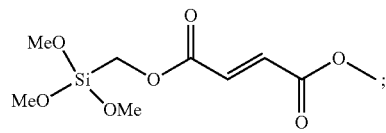

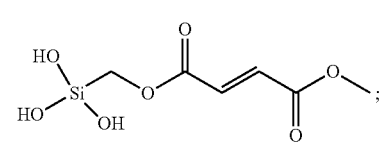

or

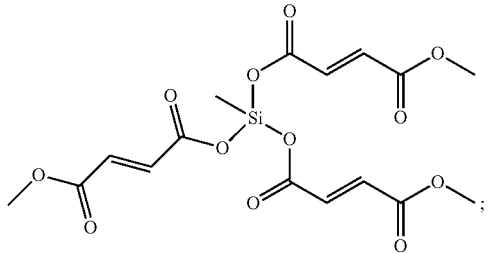

or a pharmaceutically acceptable salt thereof.

In one embodiment, the compounds of Formula (VI) and Formula (VI') may be prepared using methods known to those skilled in the art, for example, as disclosed in WO2013/119677.

In one embodiment, the prodrugs of monoalkyl fumarates are the prodrugs disclosed in WO2013/119677, such as the compounds of Formula (VII):

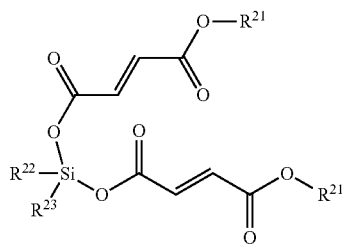

or a pharmaceutically acceptable salt, clathrate, solvate, or stereoisomer thereof, wherein:

wherein $R^{21}$ is $C_{1-6}$ alkyl; and each of $R^{22}$ and $R^{23}$ independently is $C_{1-10}$ alkyl or $C_{5-14}$ aryl;

each of which can be optionally substituted.

In certain embodiments of a compound of Formula (VII), $R^{21}$ is optionally substituted $C_{1-6}$ alkyl. In certain embodiments of a compound of Formula (VII), $R^{21}$ is optionally substituted methyl, ethyl, or isopropyl. In certain embodiments of a compound of Formula (VII), $R^{21}$ is methyl.

In certain embodiments of a compound of Formula (VII), each of $R^{22}$ and $R^{23}$ independently is optionally substituted $C_{1-10}$ alkyl. In certain embodiments of a compound of Formula (VII), each of $R^{22}$ and $R^{23}$ independently is optionally substituted $C_{1-6}$ alkyl. In certain embodiments of a compound of Formula (VII), each of $R^{22}$ and $R^{23}$ independently is optionally substituted methyl, ethyl, or isopropyl. In certain embodiments of a compound of Formula (VII), each of $R^{22}$ and $R^{23}$ independently is optionally substituted $C_{5-14}$ aryl. In certain embodiments of a compound of Formula (VII), each of $R^{22}$ and $R^{23}$ independently is optionally substituted $C_{5-10}$ aryl.

In one embodiment, the prodrugs of monoalkyl fumarates are the prodrugs disclosed in WO2013/119677, such as the compounds of Formula (VII'):

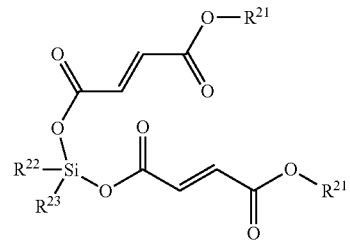

or a pharmaceutically acceptable salt, clathrate, solvate, or stereoisomer thereof, wherein $R^{21}$ is $C_{1-6}$ alkyl; and each of $R^{22}$ and $R^{23}$ independently is $C_{1-10}$ alkyl or $C_{6-10}$ aryl.

In one embodiment, the compounds of Formula (VII) and Formula (VII') may be prepared using methods known to those skilled in the art, for example, as disclosed in WO2013/119677.

In one embodiment, the prodrugs of monoalkyl fumarates are the prodrugs disclosed in WO2013/119677, such as the compounds of Formula (VIII):

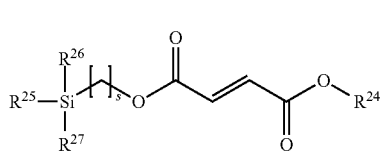

or a pharmaceutically acceptable salt, clathrate, solvate, or stereoisomer thereof, wherein:

$R^{24}$ is $C_{1-6}$ alkyl;

each of $R^{25}$, $R^{26}$, and $R^{27}$ independently is hydroxyl, $C_{1-10}$ alkyl, $C_{5-14}$ aryl, —O—$C_{1-10}$ alkyl, or —O—$C_{5-14}$ aryl;

each of which can be optionally substituted; and s is 1 or 2.

In certain embodiments of a compound of Formula (VIII), $R^{24}$ is optionally substituted $C_1$-$C_6$ alkyl. In certain embodiments of a compound of Formula (VIII), $R^{24}$ is optionally substituted methyl, ethyl, or isopropyl. In certain embodiments of a compound of Formula (VIII), $R^{24}$ is methyl.

In certain embodiments of a compound of Formula (VIII), each of $R^{25}$, $R^{26}$, and $R^{27}$ is hydroxyl. In certain embodiments of a compound of Formula (VIII), each of $R^{25}$, $R^{26}$, and $R^{27}$ independently is optionally substituted $C_{1-10}$ alkyl. In certain embodiments of a compound of Formula (VIII), each of $R^{25}$, $R^{26}$, and $R^{27}$ independently is optionally substituted $C_{1-6}$ alkyl. In certain embodiments of a compound of Formula (VIII), each of $R^{25}$, $R^{26}$, and $R^{27}$ independently is optionally substituted methyl, ethyl, or isopropyl. In certain embodiments of a compound of Formula (VIII), each of $R^{25}$, $R^{26}$, and $R^{27}$ independently is optionally substituted $C_{5-14}$ aryl. In certain embodiments of a compound of Formula (VIII), each of $R^{25}$, $R^{26}$, and $R^{27}$ independently is optionally substituted $C_{5-10}$ aryl.

In one embodiment, the prodrugs of monoalkyl fumarates are the prodrugs disclosed in WO2013/119677, such as the compounds of Formula (VIII'):

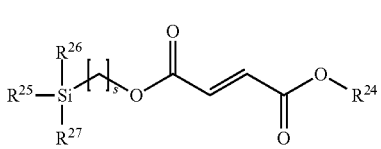

(VIII')

or a pharmaceutically acceptable salt, clathrate, solvate, or stereoisomer thereof, wherein:

$R^{24}$ is $C_{1-6}$ alkyl;

each of $R^2$, $R^{26}$, and $R^2$ independently is hydroxyl, $C_{1-10}$ alkyl, $C_{6-10}$ aryl, —O—$C_{1-10}$ alkyl, or —O—$C_{6-10}$ aryl; and s is 1 or 2.

In one embodiment, the compounds of Formula (VIII) and Formula (VIII') may be prepared using methods known to those skilled in the art, for example, as disclosed in WO2013/119677.

In one embodiment, the prodrugs of monoalkyl fumarates are the prodrugs disclosed in WO2013/119677, such as the compounds of Formula (IX):

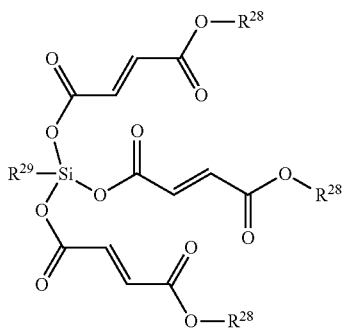

(IX)

or a pharmaceutically acceptable salt, clathrate, solvate, or stereoisomer thereof, wherein each of $R^{28}$ independently is $C_{1-6}$ alkyl; and $R^{29}$ is $C_{1-10}$ alkyl;

each of which can be optionally substituted.

In certain embodiments of a compound of Formula (IX), each of $R^{28}$ independently is optionally substituted $C_{1-6}$ alkyl. In certain embodiments of a compound of Formula (IX), each of $R^{28}$ independently is optionally substituted methyl, ethyl, or isopropyl. In certain embodiments of a compound of Formula (IX), each of $R^{28}$ is methyl.

In certain embodiments of a compound of Formula (IX), $R^{29}$ is optionally substituted $C_{1-6}$ alkyl. In certain embodiments of a compound of Formula (IX), $R^{29}$ is optionally substituted methyl, ethyl, or isopropyl.

In one embodiment, the prodrugs of monoalkyl fumarates are the prodrugs disclosed in WO2013/119677, such as the compounds of Formula (IX'):

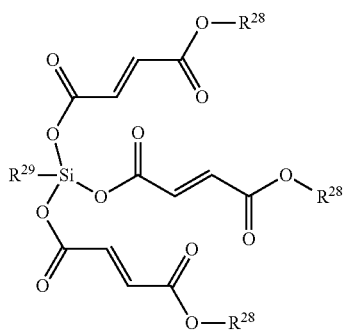

(IX')

or a pharmaceutically acceptable salt, clathrate, solvate, or stereoisomer thereof, wherein $R^{28}$ is $C_{1-6}$ alkyl; and $R^{29}$ is $C_{1-10}$ alkyl.

In one embodiment, the compounds of Formula (IX) and Formula (IX') may be prepared using methods known to those skilled in the art, for example, as disclosed in WO2013/119677.

In one embodiment, the prodrugs of monoalkyl fumarates are the prodrugs disclosed in U.S. Pat. No. 8,669,281 B1, such as the compounds of Formula (X):

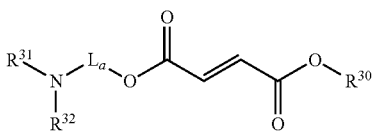

(X)

or a pharmaceutically acceptable salt, clathrate, solvate, tautomer, or stereoisomer thereof, wherein $R^{30}$ is unsubstituted $C_{1-6}$ alkyl;

$L_a$ is substituted or unsubstituted $C_{1-6}$ alkyl linker, substituted or unsubstituted $C_{3-10}$ carbocycle, substituted or unsubstituted $C_{6-10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; and $R^{31}$ and $R^{32}$ are each, independently, hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-10}$ aryl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

or alternatively, $R^{31}$ and $R^{32}$, together with the nitrogen atom to which they are attached, form a substituted or unsubstituted heteroaryl comprising one or two 5- or 6-member rings and 1-4 heteroatoms selected from N, O, and S or a substituted or unsubstituted heterocycle comprising one or two 5- or 6-member rings and 1-4 heteroatoms selected from N, O, and S.

In certain embodiments of a compound of Formula (X), $R^{30}$ is methyl. In certain embodiments of a compound of Formula (X), $R^{30}$ is ethyl.

In certain embodiments of a compound of Formula (X), La is substituted or unsubstituted $C_{1-6}$ alkyl linker. In certain embodiments of a compound of Formula (X), La is substituted or unsubstituted $C_{1-3}$ alkyl linker. In certain embodiments of a compound of Formula (X), La is substituted or unsubstituted $C_2$ alkyl linker. In certain embodiments of a compound of Formula (X), $L_a$ is a methyl substituted or unsubstituted $C_2$ alkyl linker. In certain embodiments of a compound of Formula (X), $L_a$ is a di-methyl substituted or unsubstituted $C_2$ alkyl linker. In certain embodiments of a compound of Formula (X), $L_a$ is a methyl or di-methyl substituted $C_2$ alkyl linker. In certain embodiments of a compound of Formula (X), $L_a$ is unsubstituted $C_2$ alkyl linker.

In certain embodiments of a compound of Formula (X), $R^{31}$ is substituted or unsubstituted $C_{1-6}$ alkyl. In certain embodiments of a compound of Formula (X), $R^{31}$ is unsubstituted $C_{1-6}$ alkyl. In certain embodiments of a compound of Formula (X), $R^{31}$ is unsubstituted $C_{1-3}$ alkyl. In certain embodiments of a compound of Formula (X), $R^{31}$ is unsubstituted $C_{1-2}$ alkyl.

In certain embodiments of a compound of Formula (X), $R^3$ is $C(O)OR_a$— substituted $C_{1-6}$ alkyl, wherein $R_a$ is hydrogen or unsubstituted $C_{1-6}$ alkyl. In certain embodiments of a compound of Formula (X), R is $S(O)(O)R_b$- substituted $C_{1-6}$ alkyl, wherein Rb is unsubstituted $C_{1-6}$ alkyl.

In certain embodiments of a compound of Formula (X), $R^{32}$ is hydrogen. In certain embodiments of a compound of Formula (X), $R^{32}$ is substituted or unsubstituted $C_{1-6}$ alkyl. In certain embodiments of a compound of Formula (X), $R^{32}$ is unsubstituted $C_{1-6}$ alkyl.

In certain embodiments of a compound of Formula (X), $R^{31}$ and $R^{32}$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S.

In certain embodiments of a compound of Formula (X), $R^{31}$ and $R^{32}$, together with the nitrogen atom to which they are attached, form a substituted or unsubstituted heterocycle comprising one or two 5- or 6-member rings and 1-4 heteroatoms selected from N, O, and S.

In certain embodiments of a compound of Formula (X), $R^{31}$ and $R^{32}$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

In certain embodiments of a compound of Formula (X), $R^{31}$ and $R^{32}$, together with the nitrogen atom to which they are attached, form a substituted or unsubstituted piperidinyl ring.

In certain embodiments of a compound of Formula (X), $R^{31}$ and $R^{32}$, together with the nitrogen atom to which they are attached, form an unsubstituted piperidinyl ring.

In certain embodiments of a compound of Formula (X), $R^{31}$ and $R^{32}$, together with the nitrogen atom to which they are attached, form a halogen substituted piperidinyl ring. In certain embodiments of a compound of Formula (X), $R^{31}$ and $R^{32}$, together with the nitrogen atom to which they are attached, form a 4-halogen substituted piperidinyl ring.

In certain embodiments of a compound of Formula (X), $R^{31}$ and $R^{32}$, together with the nitrogen atom to which they are attached, form an unsubstituted morpholinyl ring.

In certain embodiments of a compound of Formula (X), $R^{31}$ and $R^{32}$, together with the nitrogen atom to which they are attached, form an unsubstituted pyrrolidinyl ring.

In certain embodiments of a compound of Formula (X), $R^{31}$ and $R^{32}$, together with the nitrogen atom to which they are attached, form a substituted or unsubstituted heteroaryl comprising one or two 5 or 6-member rings and 1-4 heteroatoms selected from N, O, and S.

In certain embodiments of a compound of Formula (X), $R^{31}$ is substituted or unsubstituted $C_{6-10}$ aryl. In certain embodiments of a compound of Formula (X), $R^{31}$ is unsubstituted $C_6$-$C_{10}$ aryl. In certain embodiments of a compound of Formula (X), $R^{31}$ is unsubstituted phenyl. In certain embodiments of a compound of Formula (X), $R^{31}$ is unsubstituted benzyl.

In one embodiment, the compounds of Formula (X) may be prepared using methods known to those skilled in the art, for example, as disclosed in U.S. Pat. No. 8,669,281 B1.

In one embodiment, the prodrugs of monoalkyl fumarates are the prodrugs disclosed in U.S. Pat. No. 8,669,281 B1, such as the compounds of Formula (X'):

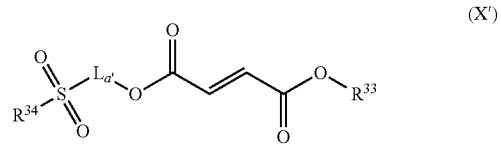

or a pharmaceutically acceptable salt, clathrate, solvate, tautomer, or stereoisomer thereof, wherein $R^{33}$ is unsubstituted $C_{1-6}$ alkyl;

$L_{a'}$ is substituted or unsubstituted $C_{1-6}$ alkyl linker, substituted or unsubstituted $C_{3-10}$ carbocycle, substituted or unsubstituted $C_{6-10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; and $R^{34}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-10}$ aryl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S.

In certain embodiments of a compound of Formula (X'), $R^{33}$ is methyl. In certain embodiments of a compound of Formula (X'), $R^{33}$ is ethyl.

In certain embodiments of a compound of Formula (X'), $L_{a'}$ is substituted or unsubstituted $C_{1-6}$ alkyl linker. In certain embodiments of a compound of Formula (X'), $L_{a'}$ is substituted or unsubstituted $C_{1-3}$ alkyl linker.

In certain embodiments of a compound of Formula (X'), $L_{a'}$ is substituted or unsubstituted $C_2$ alkyl linker. In certain embodiments of a compound of Formula (X'), $L_{a'}$ is methyl substituted or unsubstituted $C_2$ alkyl linker. In certain embodiments of a compound of Formula (X'), $L_{a'}$ is di-methyl substituted or unsubstituted $C_2$ alkyl linker. In certain embodiments of a compound of Formula (X'), $L_{a'}$ is methyl or di-methyl substituted $C_2$ alkyl linker. In certain embodiments of a compound of Formula (X'), $L_{a'}$ is unsubstituted $C_2$ alkyl linker.

In certain embodiments of a compound of Formula (X'), $R^{34}$ is substituted or unsubstituted $C_{1-6}$ alkyl. In certain embodiments of a compound of Formula (X'), $R^{34}$ is unsubstituted $C_{1-6}$ alkyl. In certain embodiments of a compound of Formula (X'), $R^{34}$ is methyl.

In certain embodiments of a compound of Formula (X'), $R^{34}$ is unsubstituted $C_{1-3}$ alkyl. In certain embodiments of a compound of Formula (X'), $R^{34}$ is unsubstituted $C_{1-2}$ alkyl.

In certain embodiments of a compound of Formula (X'), $R^{34}$ is C(O)O$R_{a'}$-substituted $C_{1-6}$ alkyl, wherein $R_{a'}$ is H or unsubstituted $C_{1-6}$ alkyl. In certain embodiments of a compound of Formula (X'), $R^{34}$ is S(O)(O)$R_{b'}$-substituted $C_{1-6}$ alkyl, wherein Rb is unsubstituted $C_{1-6}$ alkyl.

In one embodiment, the compounds of Formula (X') may be prepared using methods known to those skilled in the art, for example, as disclosed in U.S. Pat. No. 8,669,281 B1.

In one embodiment, the prodrugs of monoalkyl fumarates are the prodrugs disclosed in U.S. Pat. No. 8,669,281 B1, such as the compounds of Formula (X"):

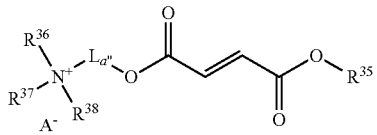

or a clathrate, solvate, tautomer, or stereoisomer thereof, wherein $A^-$ is a pharmaceutically acceptable anion;

$R^{35}$ is unsubstituted $C_{1-6}$ alkyl;

$L_{a''}$ is substituted or unsubstituted $C_{1-6}$ alkyl linker, substituted or unsubstituted $C_{3-10}$ carbocycle, substituted or unsubstituted $C_{6-10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

$R^{36}$ and $R^{37}$ are each, independently, hydrogen, substituted or unsubstituted $C_{1-6}$ alkyl, substituted or unsubstituted $C_{2-6}$ alkenyl, substituted or unsubstituted $C_2$-$C_6$ alkynyl, substituted or unsubstituted $C_{6-10}$ aryl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

or alternatively, $R^{36}$ and $R^{37}$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S; and $R^{38}$ is substituted or unsubstituted $C_{1-6}$ alkyl.

In certain embodiments of a compound of Formula (X"), $R^{35}$ is methyl. In certain embodiments of a compound of Formula (X"), $R^{35}$ is ethyl.

In certain embodiments of a compound of Formula (X"), $L_{a''}$ is substituted or unsubstituted $C_{1-6}$ alkyl linker. In certain embodiments of a compound of Formula (X"), $L_{a''}$ is substituted or unsubstituted $C_{1-3}$ alkyl linker.

In certain embodiments of a compound of Formula (X"), $L_{a''}$ is substituted or unsubstituted $C_2$ alkyl linker. In certain embodiments of a compound of Formula (X"), $L_{a''}$ is methyl substituted or unsubstituted $C_2$ alkyl linker. In certain embodiments of a compound of Formula (X"), $L_{a''}$ is di-methyl substituted or unsubstituted $C_2$ alkyl linker. In certain embodiments of a compound of Formula (X"), $L_{a''}$ is methyl or di-methyl substituted $C_2$ alkyl linker. In certain embodiments of a compound of Formula (X"), $L_{a''}$ is unsubstituted $C_2$ alkyl linker.

In certain embodiments of a compound of Formula (X"), $R^{36}$ is substituted or unsubstituted $C_{1-6}$ alkyl. In certain embodiments of a compound of Formula (X"), $R^{36}$ is unsubstituted $C_{1-6}$ alkyl. In certain embodiments of a compound of Formula (X"), $R^{36}$ is unsubstituted $C_{1-3}$ alkyl. In certain embodiments of a compound of Formula (X"), $R^{36}$ is unsubstituted $C_{1-2}$ alkyl.

In certain embodiments of a compound of Formula (X"), $R^{36}$ is C(O)O$R_{a''}$-substituted $C_{1-6}$ alkyl, wherein $R_{a''}$ is hydrogen or unsubstituted $C_{1-6}$ alkyl. In certain embodiments of a compound of Formula (X"), $R^{36}$ is S(O)(O)$R_{b''}$-substituted $C_{1-6}$ alkyl, wherein $R_{b''}$ is unsubstituted $C_{1-6}$ alkyl.

In certain embodiments of a compound of Formula (X"), $R^{36}$ and $R^{37}$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S.

In certain embodiments of a compound of Formula (X"), $R^{36}$ and $R^{37}$, together with the nitrogen atom to which they are attached, form a substituted or unsubstituted heterocycle comprising one or two 5- or 6-member rings and 1-4 heteroatoms selected from N, O, and S.

In certain embodiments of a compound of Formula (X"), $R^{36}$ and $R^{37}$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

In certain embodiments of a compound of Formula (X"), $R^{36}$ and $R^{37}$, together with the nitrogen atom to which they are attached, form a substituted or unsubstituted piperidinyl ring. In certain embodiments of a compound of Formula (X"), $R^{36}$ and $R^{37}$, together with the nitrogen atom to which they are attached, form an unsubstituted piperidinyl ring. In certain embodiments of a compound of Formula (X"), $R^{36}$ and $R^{37}$, together with the nitrogen atom to which they are attached, form a halogen substituted piperidinyl ring. In certain embodiments of a compound of Formula (X"), $R^{36}$ and $R^{37}$, together with the nitrogen atom to which they are attached, form a 4-halogen substituted piperidinyl ring.

In certain embodiments of a compound of Formula (X"), $R^{36}$ and $R^{37}$, together with the nitrogen atom to which they are attached, form an unsubstituted morpholinyl ring.

In certain embodiments of a compound of Formula (X"), $R^{36}$ and $R^{37}$, together with the nitrogen atom to which they are attached, form an unsubstituted pyrrolidinyl ring.

In certain embodiments of a compound of Formula (X"), $R^{36}$ and $R^{37}$, together with the nitrogen atom to which they are attached, form a substituted or unsubstituted heteroaryl comprising one or two 5- or 6-member rings and 1-4 heteroatoms selected from N, O, and S.

In certain embodiments of a compound of Formula (X"), $R^{36}$ is substituted or unsubstituted $C_{6-10}$ aryl. In certain embodiments of a compound of Formula (X"), $R^{36}$ is unsubstituted $C_{6-10}$ aryl. In certain embodiments of a compound of Formula (X"), $R^{36}$ is unsubstituted phenyl. In certain embodiments of a compound of Formula (X"), $R^{36}$ is unsubstituted benzyl.

In certain embodiments of a compound of Formula (X"), $R^{37}$ is hydrogen.

In certain embodiments of a compound of Formula (X"), $R^{37}$ is substituted or unsubstituted $C_{1-6}$ alkyl. In certain embodiments of a compound of Formula (X"), $R^{37}$ is unsubstituted $C_{1-6}$ alkyl.

In certain embodiments of a compound of Formula (X"), $R^{38}$ is unsubstituted $C_{1-6}$ alkyl. In certain embodiments of a compound of Formula (X"), $R^{38}$ is unsubstituted $C_{1-3}$ alkyl. In certain embodiments of a compound of Formula (X"), $R^{38}$ is methyl.

In one embodiment, the compounds of Formula (X") may be prepared using methods known to those skilled in the art, for example, as disclosed in U.S. Pat. No. 8,669,281 B1.

In one embodiment, the prodrugs of monoalkyl fumarates are the prodrugs disclosed in U.S. Pat. No. 8,669,281 B1, such as the compounds of Formula (XI):

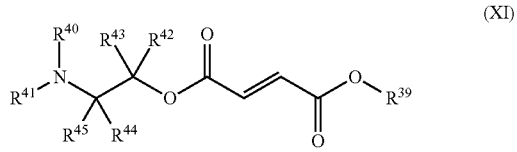

(XI)

or a pharmaceutically acceptable salt, clathrate, solvate, tautomer, or stereoisomer thereof, wherein $R^{39}$ is unsubstituted $C_{1-6}$ alkyl;

$R^{40}$ and $R^{41}$ are each, independently, hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-10}$ aryl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

$R^{42}$, $R^{43}$, $R^{44}$, and $R^{45}$ are each, independently, hydrogen, substituted or unsubstituted $C_{1-6}$ alkyl, substituted or unsubstituted $C_{2-6}$ alkenyl, substituted or unsubstituted $C_{2-6}$ alkynyl or $C(O)OR_b$; and $R_b$ is H or substituted or unsubstituted $C_1$-$C_6$ alkyl.

In certain embodiments of a compound of Formula (XI), $R^{39}$ is methyl. In certain embodiments of a compound of Formula (XI), $R^{39}$ is ethyl.

In certain embodiments of a compound of Formula (XI), $R^{40}$ is substituted or unsubstituted $C_{1-6}$ alkyl. In certain embodiments of a compound of Formula (XI), $R^{40}$ is unsubstituted $C_{1-6}$ alkyl. In certain embodiments of a compound of Formula (XI), $R^{40}$ is unsubstituted $C_{1-3}$ alkyl. In certain embodiments of a compound of Formula (XI), $R^{40}$ is unsubstituted $C_{1-2}$ alkyl.

In certain embodiments of a compound of Formula (XI), $R^{40}$ is $C(O)OR_b$— substituted $C_{1-6}$ alkyl, wherein $R_b$ is hydrogen or unsubstituted $C_{1-6}$ alkyl. In certain embodiments of a compound of Formula (XI), $R^{40}$ is $S(O)(O)R_b$-substituted $C_{1-6}$ alkyl, wherein $R_b$ is unsubstituted $C_{1-6}$ alkyl.

In certain embodiments of a compound of Formula (XI), $R^{40}$ is substituted or unsubstituted $C_{6-10}$ aryl. In certain embodiments of a compound of Formula (XI), $R^{40}$ is unsubstituted $C_{6-10}$ aryl. In certain embodiments of a compound of Formula (XI), $R^{40}$ is unsubstituted phenyl. In certain embodiments of a compound of Formula (XI), $R^{40}$ is unsubstituted benzyl.

In certain embodiments of a compound of Formula (XI), $R^{41}$ is hydrogen.

In certain embodiments of a compound of Formula (XI), $R^{41}$ is substituted or unsubstituted $C_{1-6}$ alkyl. In certain embodiments of a compound of Formula (XI), $R^{41}$ is unsubstituted $C_{1-6}$ alkyl.

In certain embodiments of a compound of Formula (XI), $R^{42}$, $R^{43}$, $R^{44}$, and $R^4$ are each hydrogen.

In certain embodiments of a compound of Formula (XI), $R^{42}$ is substituted or unsubstituted $C_{1-6}$ alkyl and $R^4$, $R^4$, and $R^{45}$ are each hydrogen. In certain embodiments of a compound of Formula (XI), $R^{42}$ is unsubstituted $C_{1-6}$ alkyl and $R^{43}$, $R^{44}$, and $R^{45}$ are each hydrogen.

In certain embodiments of a compound of Formula (XI), $R^{44}$ is substituted or unsubstituted $C_{1-6}$ alkyl and $R^{42}$, $R^{43}$, and $R^{45}$ are each hydrogen. In certain embodiments of a compound of Formula (XI), $R^{44}$ is unsubstituted $C_{1-6}$ alkyl and $R^{42}$, $R^{43}$, and $R^{45}$ are each hydrogen.

In certain embodiments of a compound of Formula (XI), $R^{42}$ and $R^{44}$ are each, independently, substituted or unsubstituted $C_{1-6}$ alkyl and $R^{43}$ and $R^{45}$ are each hydrogen. In certain embodiments of a compound of Formula (XI), $R^{42}$ and $R^{44}$ are each, independently, unsubstituted $C_{1-6}$ alkyl and $R^{43}$ and $R^{45}$ are each hydrogen.

In certain embodiments of a compound of Formula (XI), $R^{42}$ and $R^{43}$ are each, independently, substituted or unsubstituted $C_{1-6}$ alkyl and $R^{44}$ and $R^{45}$ are each hydrogen. In certain embodiments of a compound of Formula (XI), $R^{42}$ and $R^{43}$ are each, independently, unsubstituted $C_{1-6}$ alkyl and $R^{44}$ and $R^{45}$ are each hydrogen.

In certain embodiments of a compound of Formula (XI), $R^{44}$ and $R^{45}$ are each, independently, substituted or unsubstituted $C_{1-6}$ alkyl and $R^{42}$ and $R^{43}$ are each hydrogen. In certain embodiments of a compound of Formula (XI), $R^{44}$ and $R^{45}$ are each, independently, unsubstituted $C_{1-6}$ alkyl and $R^{42}$ and $R^{43}$ are each hydrogen.

In one embodiment, the compounds of Formula (XI) may be prepared using methods known to those skilled in the art, for example, as disclosed in U.S. Pat. No. 8,669,281 B1.

In one embodiment, the prodrugs of monoalkyl fumarates are the prodrugs disclosed in U.S. Pat. No. 8,669,281 B1, such as the compounds of Formula (XII):

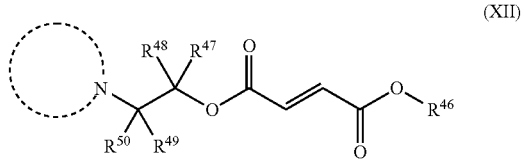

(XII)

or a pharmaceutically acceptable salt, clathrate, solvate, tautomer, or stereoisomer thereof, wherein $R^{46}$ is unsubstituted $C_{1-6}$ alkyl;

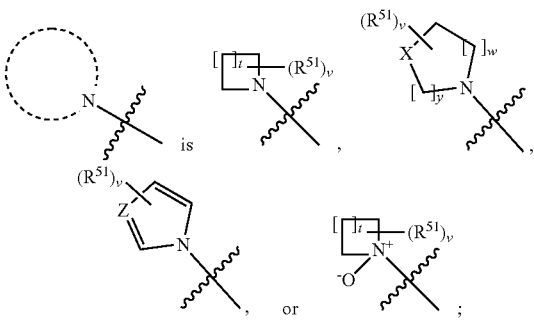

X is N, O, S, or $SO_2$;
Z is C or N;
t is 0, 1, 2, or 3;
y is 1 or 2;
w is 0, 1, 2, or 3;
v is 0, 1, 2, 3, 4, 5, 6, 7, 8, 9, or 10;
$R^{47}$, $R^{48}$, $R^{49}$, and $R^{50}$ are each, independently, hydrogen, substituted or unsubstituted $C_{1-6}$ alkyl, substituted or unsubstituted $C_{2-6}$ alkenyl, substituted or unsubstituted $C_{2-6}$ alkynyl or $C(O)OR^{52}$; and
$R^{52}$ is hydrogen or substituted or unsubstituted $C_{1-6}$ alkyl; and each $R^5$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;
or, alternatively, two $R^{51}$'s attached to the same carbon atom, together with the carbon atom to which they are attached, form a carbonyl, substituted or unsubstituted $C_{3-10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;
or, alternatively, two $R^{51}$'s attached to different atoms, together with the atoms to which they are attached, form a substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S.

In certain embodiments of a compound of Formula (XII), $R^{46}$ is methyl. In certain embodiments of a compound of Formula (XII), $R^{46}$ is ethyl.

In certain embodiments of a compound of Formula (XII),

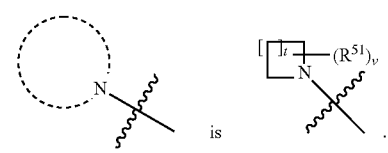

In certain embodiments of a compound of Formula (XII),

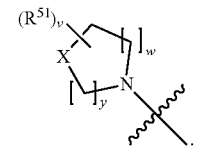

In certain embodiments of a compound of Formula (XII),

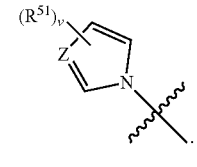

In certain embodiments of a compound of Formula (XII),

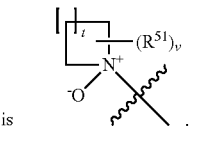

In certain embodiments of a compound of Formula (XII), $R^{47}$ is substituted or unsubstituted $C_{1-6}$ alkyl and $R^{48}$, $R^{49}$, and $R^{50}$ are each hydrogen. In certain embodiments of a compound of Formula (XII), $R^{47}$ is unsubstituted $C_{1-6}$ alkyl and $R^{48}$, $R^{49}$, and $R^{50}$ are each hydrogen.

In certain embodiments of a compound of Formula (XII), $R^{49}$ is substituted or unsubstituted $C_{1-6}$ alkyl and $R^{47}$, $R^{48}$, and $R^{50}$ are each hydrogen. In certain embodiments of a compound of Formula (XII), $R^{49}$ is unsubstituted $C_{1-6}$ alkyl and $R^{47}$, $R^{48}$, and $R^{50}$ are each hydrogen.

In certain embodiments of a compound of Formula (XII), $R^{47}$ and $R^{49}$ are each, independently, substituted or unsubstituted $C_{1-6}$ alkyl and $R^{48}$ and $R^{49}$ are each hydrogen. In certain embodiments of a compound of Formula (XII), $R^{47}$ and $R^{49}$ are each, independently, unsubstituted $C_{1-6}$ alkyl and $R^{48}$ and $R^{50}$ are each hydrogen.

In certain embodiments of a compound of Formula (XII), $R^{47}$ and $R^{48}$ are each, independently, substituted or unsubstituted $C_{1-6}$ alkyl and $R^{49}$ and $R^{50}$ are each hydrogen. In certain embodiments of a compound of Formula (XII), $R^{47}$ and $R^{48}$ are each, independently, unsubstituted $C_{1-6}$ alkyl and $R^{49}$ and $R^{50}$ are each hydrogen.

In certain embodiments of a compound of Formula (XII), $R^{49}$ and $R^{50}$ are each, independently, substituted or unsubstituted $C_{1-6}$alkyl and $R^{47}$ and $R^{48}$ are each hydrogen. In certain embodiments of a compound of Formula (XII), $R^{49}$ and $R^{50}$ are each, independently, unsubstituted $C_{1-6}$ alkyl and $R^{47}$ and $R^{48}$ are each hydrogen.

In one embodiment, the compounds of Formula (XII) may be prepared using methods known to those skilled in the art, for example, as disclosed in U.S. Pat. No. 8,669,281 B1.

In certain embodiments of a compound of Formula (X), (X'), (X"), (XI), or (XII), the compound is:

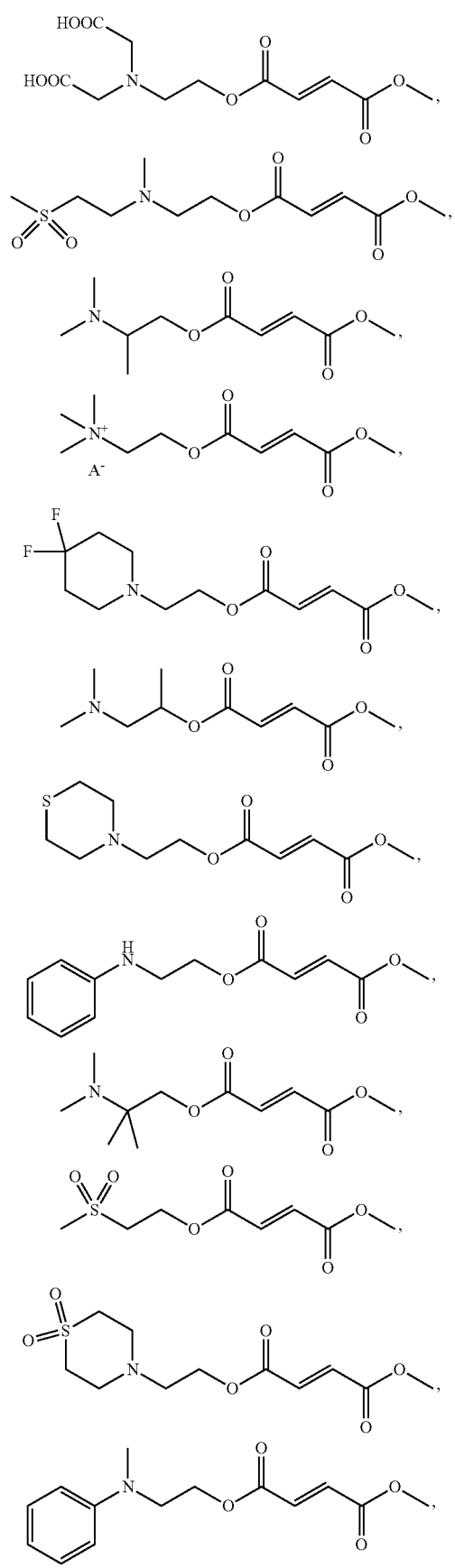
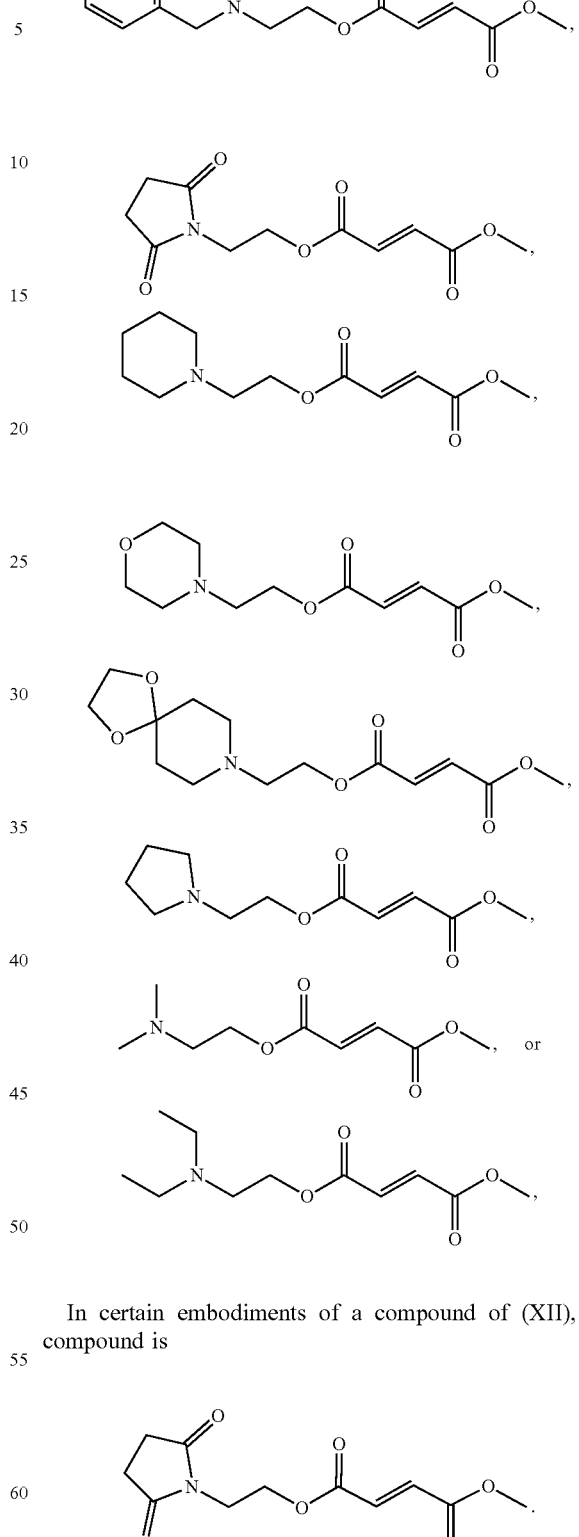
In certain embodiments of a compound of (XII), the compound is
In one embodiment, the prodrugs of monoalkyl fumarates are the prodrugs disclosed in WO2014/096425, such as the compounds of Formula (XII):

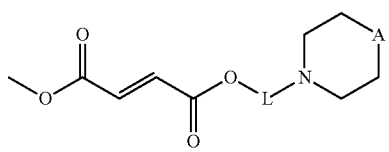
(XIII)

or a pharmaceutically acceptable salt, clathrate, solvate, or stereoisomer thereof, wherein L is is an alkanediyl group with 1 to 6 carbon atoms;

A is SO, $SO_2$, or $NR^{53}$, and $R^{53}$ is $C_{1-6}$ alkyl or $C_{3-6}$ cycloalkyl.

In certain embodiments of a compound of Formula (XIII), L is an alkanediyl group with 2, 3 or 4 carbon atoms, or with 2 or 4 carbon atoms, or with 2 carbons atoms. In certain embodiments of a compound of Formula (XIII), L is —$CH_2CH_2$—. In certain embodiments of a compound of Formula (XIII), A is SO or $SO_2$. In certain embodiments of a compound of Formula (XIII), $R^{53}$ is methyl, ethyl, propyl, isopropyl, butyl, isobutyl, tert-butyl, pentyl, sec-pentyl, or hexyl. In certain embodiments of a compound of Formula (XIII), $R^{53}$ is cyclopropyl, cyclobutyl, cyclopentyl and cyclohexyl. In certain embodiments of a compound of Formula (XIII), $R^{53}$ is $C_{1-4}$ alkyl, $C_3$ or $C_4$ or $C_5$ cycloalkyl. In certain embodiments of a compound of Formula (XIII), $R^{53}$ is methyl or isopropyl.

In one embodiment, the compounds of Formula (XIII) may be prepared using methods known to those skilled in the art, for example, as disclosed in WO2014/096425.

In one embodiment, the prodrugs of monoalkyl fumarates are the prodrugs disclosed in WO2014/096425, such as the compounds of Formula (XIV):

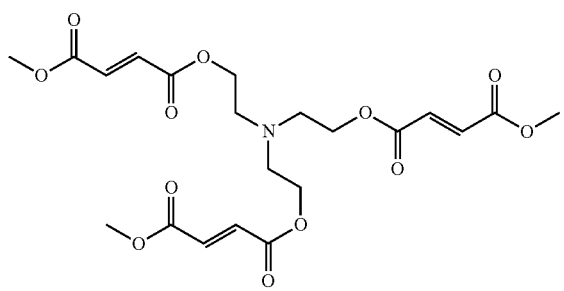
(XIV)

or a clathrate, or solvate thereof.

In one embodiment, the compounds of Formula (XIV) may be prepared using methods known to those skilled in the art, for example, as disclosed in WO2014/096425.

In one embodiment, the prodrugs of monoalkyl fumarates are the prodrugs disclosed in WO2014/096425, such as the compounds of Formula (XV):

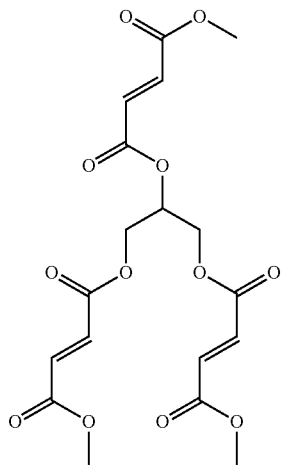
(XV)

or a clathrate, or solvate thereof.

In one embodiment, the compounds of Formula (XV) may be prepared using methods known to those skilled in the art, for example, as disclosed in WO2014/096425.

In one embodiment, the prodrugs of monoalkyl fumarates are the prodrugs disclosed in WO2014/096425, such as the compounds of Formula (XVI):

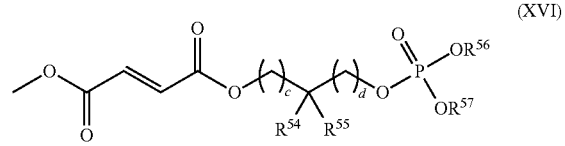
(XVI)

or a clathrate, solvate, or stereoisomer thereof, wherein $R^{54}$ and $R^{55}$ are each, independently, hydrogen, $C_{1-6}$ alkyl, or $C_{3-6}$ cycloalkyl;

$R^{56}$ and $R^{57}$ are each, independently, hydrogen or $C_{1-6}$ alkyl; and c and d are each, independently, an integer from 0 to 3.

In certain embodiments of a compound of Formula (XVI), $R^{54}$ and $R^{55}$ are each, independently, hydrogen, methyl, or ethyl. In certain embodiments of a compound of Formula (XVI), $R^{54}$ and $R^{55}$ are each, independently, hydrogen or methyl. In certain embodiments of a compound of Formula (XVI), $R^{54}$ and $R^{55}$ are both hydrogen; or $R^{54}$ is hydrogen and $R^{55}$ is methyl. In certain embodiments of a compound of Formula (XVI), c and d each are, independently, 0 or 1. In certain embodiments of a compound of Formula (XVI), c and d are both 0. In certain embodiments of a compound of Formula (XVI), $R^{56}$ and $R^{57}$ are each, independently, $C_{1-5}$ alkyl or $C_{1-4}$ alkyl. In certain embodiments of a compound of Formula (XVI), $R^{56}$ and $R^{57}$ are tert-butyl. In certain embodiments of a compound of Formula (XVI), $R^{56}$ and $R^5$ are identical.

In one embodiment, the compounds of Formula (XVI) may be prepared using methods known to those skilled in the art, for example, as disclosed in WO2014/096425.

In one embodiment, the prodrugs of monoalkyl fumarates are the prodrugs disclosed in WO2014/096425, such as the compounds of Formula (XVII):

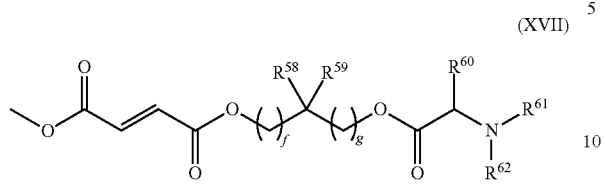

(XVII)

or a pharmaceutically acceptable salt, clathrate, solvate, tautomer, or stereoisomer thereof, wherein $R^{58}$, $R^9$, $R^{61}$, and $R^{62}$ are each, independently, hydrogen, $C_{1-6}$ alkyl, or $C_{3-6}$ cycloalkyl;

$R^{60}$ is hydrogen, $C_{3-6}$ cycloalkyl or $C_{1-6}$ alkyl, wherein the $C_{1-6}$ alkyl is optionally substituted with or or more of amino, NH—C(NH)NH$_2$, carboxamide, carboxylic acid, hydroxy, imidazole, indole, mercapto, methylthio, phenyl, hydroxyphenyl, and wherein one of $R^{61}$ and $R^{62}$ together with $R^{60}$ optionally belong to a 5 or 6-membered heteroaliphatic ring; and f and g are each, independently, an integer from 0 to 3, with the proviso that both f and g are not 0.

In certain embodiments of a compound of Formula (XVII), $R^{61}$ and $R^{62}$ are each, independently, hydrogen or $C_{1-2}$ alkyl. In certain embodiments of a compound of Formula (XVII), $R^6$ and $R^{62}$ are hydrogen. In certain embodiments of a compound of Formula (XVII), $R^6$ is hydrogen and $R^{62}$ is methyl. In certain embodiments of a compound of Formula (XVII), at least one of f and g is 0. In certain embodiments of a compound of Formula (XVII), g is 0.

In certain embodiments of a compound of Formula (XVII), $R^{60}$ is a substituted $C_{1-6}$ alkyl, wherein the substituent is one or more of the following: halogen, nitro, nitrile, urea, phenyl, aldehyde, sulfate, amino, NH—C(NH)NH$_2$, carboxamide, carboxylic acid, hydroxy, imidazole, indole, mercapto, methylthio, phenyl, and hydroxyphenyl. In particular embodiments the substituents are one or more of the following: amino, NH—C(NH)NH$_2$, carboxamide, carboxylic acid, hydroxy, imidazole, indole, mercapto, methylthio, phenyl, and hydroxyphenyl. In certain embodiments of a compound of Formula (XVII), $R^{60}$ is —CH$_2$—C$_6$H$_5$. In certain embodiments of a compound of Formula (XVII), the compound is a compound of Formula XVII':

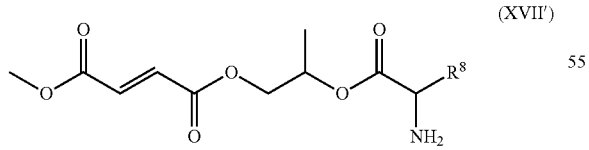

(XVII')

In one embodiment, the compounds of Formula (XVII) or (XVII') may be prepared using methods known to those skilled in the art, for example, as disclosed in WO2014/096425.

In one embodiment, the prodrugs of monoalkyl fumarates are the prodrugs disclosed in WO2014/096425, such as the compounds of Formula (XVIII):

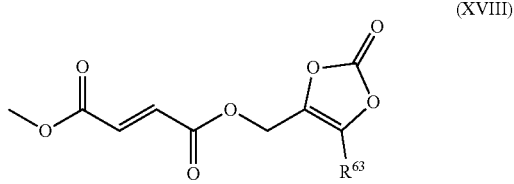

(XVIII)

or a pharmaceutically acceptable salt, clathrate, solvate, or stereoisomer thereof, wherein $R^{63}$ is hydrogen, $C_{1-6}$ alkyl, $C_{3-6}$ cycloalkyl, $C_{2-6}$ alkenyl, halogen, cyano, hydroxy, amino, carboxy, mercapto, 5 or 6-membered aryl or hetero aryl optionally substituted with one of or more of methyl, tert-butyl, hydroxy, methoxy, halogen, nitro, nitrile, amine, and carboxamide.

In certain embodiments of a compound of Formula (XVIII), $R^{63}$ is hydrogen, $C_{1-2}$ alkyl, halogen, cyano, amino, or hydroxy. In certain embodiments of a compound of Formula (XVIII), $R^{63}$ is hydrogen, hydroxyl, or methyl. In certain embodiments of a compound of Formula (XVIII), $R^{63}$ is methyl.

In one embodiment, the compounds of Formula (XVIII) may be prepared using methods known to those skilled in the art, for example, as disclosed in WO2014/096425.

In certain embodiments of a compound of Formula (XIII), (XVI), (XVII), or (XVIII), the compound is:

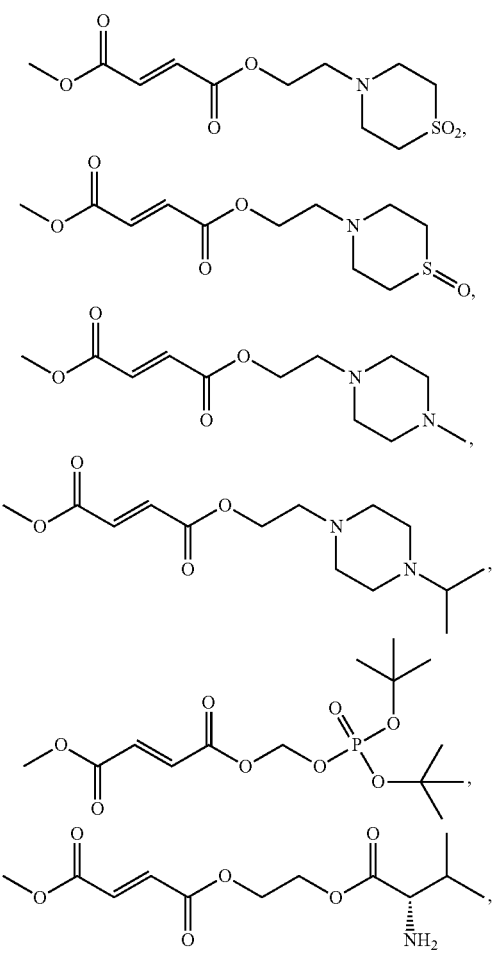

-continued

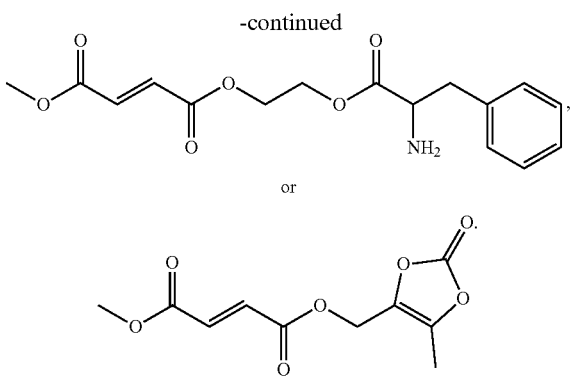

5.1.3 Deuterated Fumarates

In one embodiment, the fumarates are isotopically enriched with deuterium (2H).

In a particular embodiment, a deuterated fumarate is a compound disclosed in U.S. patent application publication number US 2014-0179779 A1, such as a compound of Formula (XIX):

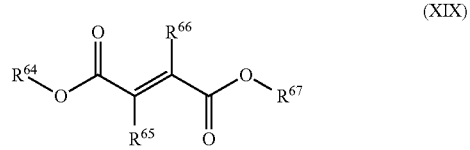
(XIX)

or a pharmaceutically acceptable salt, clathrate, solvate, tautomer, or stereoisomer thereof, wherein $R^{64}$ and $R^{67}$ are each independently hydrogen, deuterium, deuterated methyl, deuterated ethyl, $C_{1-6}$ alkyl, phenyl, 3-7 membered saturated or partially unsaturated monocyclic carbocyclic ring, 3-7 membered saturated or partially unsaturated monocyclic heterocyclic ring having 1-3 heteroatoms independently selected from nitrogen, oxygen, and sulfur, or a 5-6 membered heteroaryl ring having 1-3 heteroatoms independently selected from nitrogen, oxygen, and sulfur; and $R^{65}$ and $R^{66}$ are each independently hydrogen or deuterium, provided that the compound of Formula (XIX) contains at least one deuterium atom and that $R^{64}$ and $R^{67}$ are not hydrogen or deuterium at the same time.

In particular, fumarate Isotopologues are the compounds disclosed in US patent application publication number US 2014-0179779 A1, such as the compounds of Formula (XIX'):

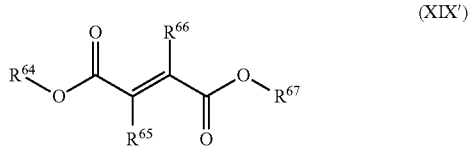
(XIX')

or a pharmaceutically acceptable salt, clathrate, solvate, or stereoisomer thereof, wherein $R^{64}$ and $R^{67}$ are each independently hydrogen, deuterium, deuterated methyl, deuterated ethyl, or $C_{1-6}$ aliphatic, and $R^{65}$ and $R^{66}$ are each independently hydrogen or deuterium, provided that the compound of formula (XIX') contains at least one deuterium atom and that $R^{64}$ and $R^{67}$ are not hydrogen or deuterium at the same time.

In certain embodiments of a compound of Formula (XIX) or Formula (XIX'), $R^{64}$ is hydrogen or —$CH_3$. In certain embodiments of a compound of Formula (XIX) or Formula (XIX'), $R^{64}$ is —$CD_3$. In certain embodiments of a compound of Formula (XIX) or Formula (XIX'), $R^{64}$ is —$CD_2CD_3$.

In certain embodiments of a compound of Formula (XIX) or Formula (XIX'), $R^{67}$ is —$CH_2D$, —$CHD_2$, or —$CD_3$. In certain embodiments of a compound of Formula (XIX) or Formula (XIX'), $R^{67}$ is H, —$CH_3$, —$CH_2D$, —$CHD_2$, or —$CD_3$.

In certain embodiments of a compound of Formula (XIX) or Formula (XIX'), $R^{64}$ is hydrogen or —$CH_3$ and $R^{67}$ is —$CH_2D$, —$CHD_2$, or —$CD_3$.

In certain embodiments of a compound of Formula (XIX) or Formula (XIX'), $R^{64}$ is —$CD_3$ and $R^{67}$ is —$CH_2D$, —$CHD_2$, or —$CD_3$.

In certain embodiments of a compound of Formula (XIX) or Formula (XIX'), at least one of $R^{65}$ and $R^{66}$ is deuterium. In certain embodiments of a compound of Formula (XIX) or Formula (XIX'), both of $R^{65}$ and $R^{66}$ are deuterium.

In certain embodiments of a compound of Formula (XIX) or Formula (XIX'), at least one of $R^{65}$ and $R^{66}$ is deuterium and $R^{67}$ is hydrogen, —$CH_3$, —$CH_2D$, —$CHD_2$, or —$CD_3$. In certain embodiments of a compound of Formula (XIX) or Formula (XIX'), both of $R^{65}$ and $R^{66}$ are deuterium and $R^{67}$ is hydrogen, —$CH_3$, —$CH_2D$, —$CHD_2$, or —$CD_3$.

In certain embodiments of a compound of Formula (XIX) or Formula (XIX'), $R^{64}$ is —$CD_2CD_3$ and $R^{67}$ is H, —$CH_3$, —$CH_2D$, —$CHD_2$, or —$CD_3$ In certain embodiments of a compound of Formula (XIX) or Formula (XIX'), the compound is ($^2H_6$)dimethyl fumaric acid ester, ($^2H_3$)methyl fumaric acid ester, ($^2H_3$)dimethyl fumaric acid ester, dimethyl fumaric(2,3-$^2H_2$) acid ester, methyl fumaric(2,3-$^2H_2$) acid ester, ethyl fumaric(2,3-$^2H_2$) acid ester, ($^2H_3$)methyl fumaric(2,3-$^2H_2$) acid ester, ($^2H_6$) dimethyl fumaric(2,3-$^2H_2$) acid ester, methyl (2-morpholino-2-oxoethyl) fumaric(2,3-$^2H_2$) acid ester, methyl (4-morpholino-1-butyl) fumaric(2,3-$^2H_2$) acid ester, 2-(benzoyloxy)ethyl methyl fumaric(2,3-$^2H_2$) acid ester, 2-(benzoyloxy)ethyl ($^2H_3$)methyl fumaric acid ester, (S)-2-((2-amino-3-phenylpropanoyl)oxy)ethyl methyl fumaric(2,3-$^2H_2$) acid ester, or (S)-2-((2-amino-3-phenylpropanoyl)oxy) ethyl ($^2H_3$)methyl fumaric acid ester; or a pharmaceutically acceptable salt, clathrate, solvate, or stereoisomer thereof.

In certain embodiments of a compound of Formula (XIX) or Formula (XIX'), the compound is:

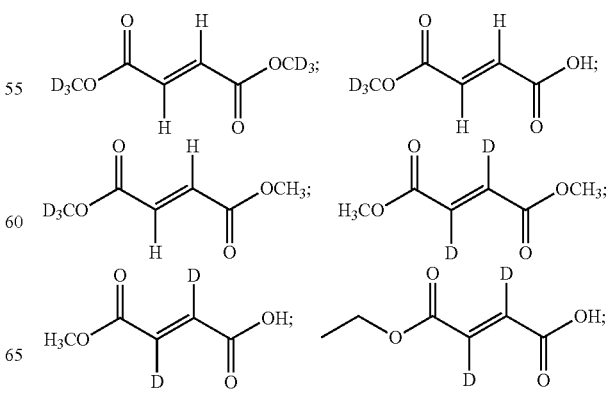

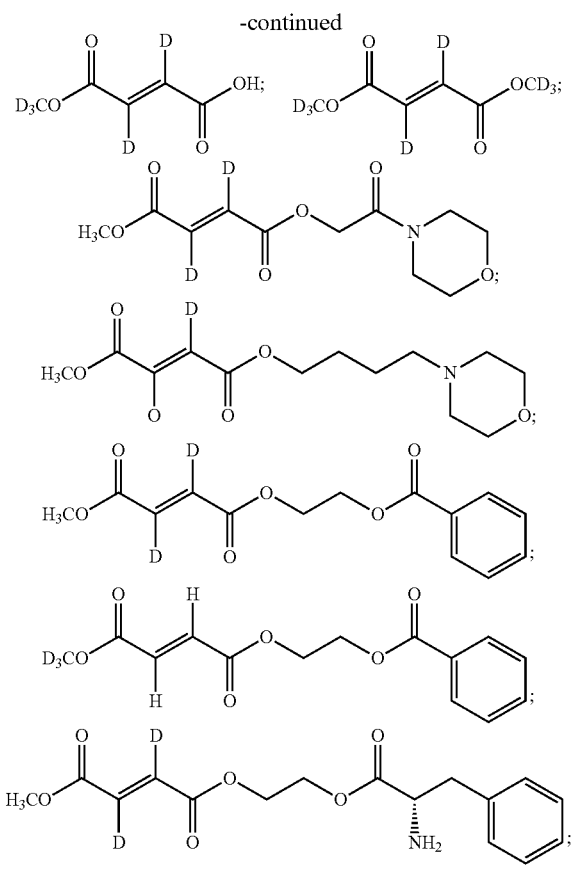

or

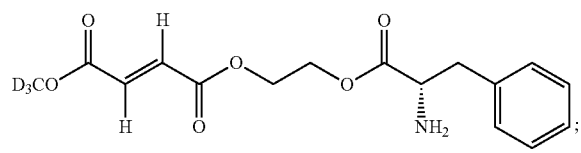

or a pharmaceutically acceptable salt, clathrate, solvate, or stereoisomer thereof.

In one embodiment, the compounds of Formula (XIX) and (XIX') may be prepared using methods known to those skilled in the art, for example, as disclosed in US patent application publication number US 2014-0179779 A1.

Deuterated fumarates are useful as active agents for the methods provided herein, e.g., treating multiple sclerosis.

In one embodiment, when a particular position in a fumarate is designated as having deuterium, it is understood that the abundance of deuterium at that position is substantially greater than the natural abundance of deuterium, which is 0.015%. A position designated as having deuterium typically has a minimum deuterium enrichment factor of at least 3340 (50.1% deuterium incorporation) at each atom designated as deuterium in said compound.

In other embodiments, a fumarate provided herein has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

5.1.4 Salts

In particular aspects, included within the scope of the fumarates described herein are the non-toxic pharmaceutically acceptable salts of the fumarates described hereinabove (wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing). Acid addition salts are formed by mixing a solution of a fumarate with a solution of a pharmaceutically acceptable non-toxic acid such as hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, gluconate, glucaronate, saccharate, formate, benzoate, glutamate, methanesulfonate, ethanesulfonate, benzenesulfonate, p-toluenesulfonate, and pamoate. Acceptable base salts include aluminum, calcium, lithium, magnesium, potassium, sodium, zinc, and diethanolamine salts.

5.2 Pharmaceutical Compositions

In one embodiment, the fumarate for use in the methods of the invention is contained in a pharmaceutical composition comprising a therapeutically effective amount of the fumarate and a pharmaceutically acceptable carrier, i.e., a pharmaceutically acceptable excipient.

In a specific embodiment, the pharmaceutical composition comprises a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a clathrate, solvate, tautomer, or stereoisomer of any of the foregoing, or a combination of any of the foregoing; with the proviso that a fumarate salt is not present in the pharmaceutical composition.

In a specific embodiment, the pharmaceutical composition comprises a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that an ethyl hydrogen fumarate salt is not present in the pharmaceutical composition.

In a specific embodiment, the pharmaceutical composition comprises a fumarate; wherein the fumarate is a dialkyl fumarate, a monoalkyl fumarate, a combination of a dialkyl fumarate and a monoalkyl fumarate, a prodrug of monoalkyl fumarate, a deuterated form of any of the foregoing, or a pharmaceutically acceptable salt, clathrate, solvate, tautomer, or stereoisomer of any of the foregoing, or a combination of any of the foregoing; with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition.

In a specific embodiment, the pharmaceutical composition consists essentially of DMF and/or monomethyl fumarate.

In a specific embodiment, the pharmaceutical composition comprises DMF. In a specific embodiment, the pharmaceutical composition consists essentially of DMF. In a specific embodiment, the pharmaceutical composition comprises DMF, with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition. In a specific embodiment, the pharmaceutical composition comprises DMF and/or monomethyl fumarate, with the proviso that ethyl hydrogen fumarate calcium salt, ethyl hydrogen fumarate magnesium salt, ethyl hydrogen fumarate zinc salt, and ethyl hydrogen fumarate copper salt are not present in the pharmaceutical composition. In a specific embodiment, the pharmaceutical composition comprises DMF, with the proviso that no additional fumarate other than DMF or monomethyl fumarate is present.

In a specific embodiment, the pharmaceutical composition can be an oral dosage form, e.g., a solid oral dosage form. In a specific embodiment, the pharmaceutical composition is a tablet, capsule, or capsule containing microtablets. Optionally, the tablet or microtablets are enterically coated. In a specific embodiment, the pharmaceutical composition is in the form of enterically coated tablets or microtablets (optionally contained in a capsule), which, once the enteric coating is dissolved in the gastro-intestinal tract, act as immediate release dosage forms.

In another specific embodiment, the pharmaceutical composition is a controlled, or sustained, release composition, optionally enterically coated.

The pharmaceutical preparations described herein are manufactured in a manner which is itself known, for example, by means of conventional mixing, granulating, dragee-making, dissolving, or lyophilizing processes. Thus, pharmaceutical preparations for oral use may be obtained by combining the fumarates with solid excipients, optionally grinding the resulting mixture and processing the mixture of granules, after adding suitable auxiliaries, if desired or necessary, to obtain tablets or dragee cores.

In general, when the drug load (or weight percent of an active ingredient) of a solid oral dosage form (e.g., a tablet or a microtablet) is significantly increased, the weight percent of the excipient(s) must decrease (especially if the size of the solid oral dosage form remains the same). The solid oral dosage form often becomes unstable due to the decrease in the amount of excipient(s), e.g., binders, that function to hold all the components together in a cohesive mix. It is unexpected that increasing the amount of DMF (e.g., from 120 mg to 240 mg) and decreasing the amount of binder, while keeping the size of the solid oral dosage form (e.g., capsule size) to be the same, the strength or integrity of solid dosage form does not suffer.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethycellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethylcellulose phthalate, are used. Dye stuffs or pigments may be added to the tablets or dragee coatings, for example, for identification or in order to characterize combinations of active compound doses.

In one embodiment, the pharmaceutical preparations described herein comprise a capsule containing the agent or pharmaceutical composition described herein in the form of an enteric-coated microtablet. The coating of the microtablet may be composed of different layers.

The first layer may be a methyacrylic acid-methyl methacrylate copolymer/isopropyl solution which isolates the tablet cores from potential hydrolysis from the next applied water suspensions.

The enteric coating of the tablet may then be conferred by an aqueous methacrylic acid-ethyl acrylate copolymer suspension.

In another embodiment, is provided a composition comprising a fumarate, such as dimethyl fumarate, and one or more excipients, wherein a total amount of the fumarate in the composition ranges, for example, from about 43% w/w to about 95% w/w, based on the total weight of the composition, excluding the weight of any coating.

The total amount of the fumarate, such as dimethyl fumarate, in the composition described herein can range, for example, from about 43% w/w to about 95% w/w, from about 50% w/w to about 95% w/w, from about 50% w/w to about 85% w/w, from about 55% w/w to about 80% w/w, from about 60% w/w to about 75% w/w, from about 60% w/w to about 70% w/w, or from about 65% w/w to about 70% w/w, based on the total weight of the composition, excluding the weight of any coating.

The composition described herein can comprise the fumarate, such as dimethyl fumarate, for example, in about 43% w/w, about 45% w/w, about 50% w/w, about 55% w/w, about 60% w/w, about 65% w/w, about 70% w/w, about 75% w/w, about 80% w/w, about 90% w/w, or about 95% w/w, based on the weight of the composition, excluding the weight of any coating. For example, the composition can contain about 65% to about 95% w/w (e.g., 65% w/w) of DMF.

Some or all of the fumarate, such as dimethyl fumarate, in the composition can have a particle size of 250 microns or less. For example, and without being limiting, at least 80%, at least 90%, at least 95%, at least 97%, or at least 99% of the fumarate, such as dimethyl fumarate, in the composition can have a particle size of 250 microns or less. Particle size can be measured, for example, by sieve analysis, air elutriation analysis, photoanalysis, electrical counting methods, electroresistance counting methods, sedimentation techniques, laser diffraction methods, acoustic spectroscopy, or ultrasound attenuation spectroscopy. In one embodiment, the particle size is measured using laser diffraction methods.

The composition described herein can comprise a total amount of excipient(s), for example, in an amount of about 5.0% w/w to about 57% w/w, based on the total weight of the composition, excluding the weight of any coating.

The composition described herein can comprise a total amount of excipient(s) in an amount ranging, for example, from about 5% w/w to about 57% w/w, from about 15% w/w to about 57% w/w, from about 20% w/w to about 57% w/w, from about 25% w/w to about 57% w/w, from about 30% w/w to about 57% w/w, from about 35% w/w to about 57% w/w, from about 40% to about 57% w/w, from about 45% w/w to about 57% w/w, from about 50% w/w to about 57% w/w, from about 55% w/w to about 57% w/w, from about 5% w/w to about 55% w/w, from about 5% w/w to about 50% w/w, from about 5% w/w to about 45% w/w, from about 5% w/w to about 40% w/w, from about 5% w/w to about 35% w/w, from about 5% w/w to about 30% w/w, from about 5% w/w to about 25% w/w, from about 5% w/w to about 20% w/w, from about 5% w/w to about 15% w/w, from about 15% w/w to about 55% w/w, from about 20% w/w to about 50% w/w, from about 25% w/w to about 45% w/w, from about 30% w/w to about 40% w/w, from about 35% to about 40% w/w, based on the total weight of the composition, excluding the weight of any coating.

The excipient(s) can be, for example, one or more selected from the group consisting of a filler (or a binder), a glidant, a disintegrant, a lubricant, or any combination thereof.

The number of excipients that can be included in a composition is not limited.

Examples of fillers or binders include, but are not limited to, ammonium alginate, calcium carbonate, calcium phosphate, calcium sulfate, cellulose, cellulose acetate, compressible sugar, confectioner's sugar, dextrates, dextrin, dextrose, erythritol, ethylcellulose, fructose, glyceryl palmitostearate, hydrogenated vegetable oil type I, isomalt, kaolin, lactitol, lactose, mannitol, magnesium carbonate, magnesium oxide, maltodextrin, maltose, mannitol, medium chain triglycerides, microcrystalline cellulose, polydextrose, polymethacrylates, simethicone, sodium alginate, sodium chloride, sorbitol, starch, sucrose, sugar spheres, sulfobutylether beta-cyclodextrin, talc, tragacanth, trehalsoe, polysorbate 80, and xylitol. In one embodiment, the filler is microcrystalline cellulose. The microcrystalline cellulose can be, for example, PROSOLV SMCC® 50, PROSOLV SMCC® 90, PROSOLV SMCC® HD90, PROSOLV SMCC® 90 LM, and any combination thereof.

Examples of disintegrants include, but are not limited to, hydroxypropyl starch, alginic acid, calcium alginate, carboxymethylcellulose calcium, carboxymethylcellulose sodium, powdered cellulose, chitosan, colloidal silicon dioxide, croscarmellose sodium, crospovidone, docusate sodium, guar gum, hydroxypropyl cellulose, low substituted hydroxypropyl cellulose, magnesium aluminum silicate, methylcellulose, microcrystalline cellulose, polacrilin potassium, povidone, sodium alginate, sodium starch glycolate, starch, and pregelatinized starch. In one embodiment, the disintegrant is croscarmellose sodium.

Examples of glidants include, but are not limited to, calcium phosphate, calcium silicate, powdered cellulose, magnesium silicate, magnesium trisilicate, silicon dioxide, talcum and colloidal silica, and colloidal silica anhydrous. In one embodiment, the glidant is colloidal silica anhydrous, talc, or a combination thereof.

Examples of lubricants include, but are not limited to, canola oil, hydroxyethyl cellulose, lauric acid, leucine, mineral oil, poloxamers, polyvinyl alcohol, talc, oxyldodecanol, sodium hyaluronate, sterilizable maize starch, triethanolamine, calcium stearate, magnesium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, potassium benzoate, sodium benzoate, sodium chloride, sodium lauryl sulfate, stearic acid, talc, and zinc stearate. In one embodiment, the lubricant is magnesium stearate.

The composition described herein can comprise a total amount of filler(s) in an amount ranging from about 3.5% w/w to about 55% w/w of the composition, based on the total weight of the composition, excluding the weight of any coating.

The filler(s) can be comprised in the composition described herein, for example, in a total amount, for example, ranging from about 5% w/w to about 55% w/w, from about 10% w/w to about 55% w/w, from about 15% w/w to about 55% w/w, from about 20% w/w to about 55% w/w, from about 25% w/w to about 55% w/w, from about 30% w/w to about 55% w/w, from about 35% w/w to about 55% w/w, from about 40% w/w to about 55% w/w, from about 3.5% w/w to about 55% w/w, from about 3.5% to about 50%, from about 3.5% w/w to about 40% w/w, from about 3.5% w/w to about 30% w/w, from about 3.5% w/w to about 25% w/w, from about 3.5% w/w to about 20% w/w, from about 3.5% w/w to about 15% w/w, from about 15% w/w to about 40% w/w, from about 20% w/w to about 35% w/w, or from about 25% w/w to about 30% w/w, based on the total weight of the composition, excluding the weight of any coating.

The filler(s) can be comprised in the composition, for example, in a total amount of about 5% w/w, about 7% w/w, about 10% w/w, about 12% w/w, about 14% w/w, about 16% w/w, about 18% w/w, about 20% w/w, about 22% w/w, about 24% w/w, about 26% w/w, about 28% w/w, about 30% w/w, about 32% w/w, about 34% w/w, about 36% w/w, about 38% w/w, about 40% w/w, about 42% w/w, about 44% w/w, about 46% w/w, about 48% w/w, about 50% w/w, about 52% w/w, about 54% w/w, or about 55% w/w, based on the total weight of the composition, excluding the weight of any coating.

The composition described herein can comprise a total amount of disintegrant(s), for example, in an amount ranging from about 0.2% w/w to about 20% w/w, based on the total weight of the composition, excluding the weight of any coating.

The disintegrant(s) can be contained in the composition, for example, in a total amount ranging from about 0.2% w/w to about 19% w/w, about 0.2% w/w to about 15% w/w, about 0.2% w/w to about 12% w/w, about 0.2% w/w to about 6% w/w, about 0.2% w/w to about 5% w/w, about 0.2% w/w to about 4% w/w, about 0.2% w/w to about 3% w/w, about 0.2% w/w to about 2% w/w, about 0.2% w/w to about 20% w/w, about 3% w/w to about 20% w/w, about 4% w/w to about 20% w/w, about 5% w/w to about 20% w/w, about 6% w/w to about 20% w/w, about 7% w/w to about 20% w/w, about 8% w/w to about 20% w/w, about 9% w/w to about 20% w/w, about 2% w/w to about 20% w/w, or about 3% w/w to about 20% w/w, based on the weight of the composition, excluding the weight of any coating.

The disintegrant(s) can be contained in the composition, for example, in a total amount of about 1% w/w, about 2% w/w, about 3% w/w, about 4% w/w, about 5% w/w, about 6% w/w, about 7% w/w, about 8% w/w, about 9% w/w, about 10% w/w, about 12% w/w, about 14% w/w, about 16% w/w, about 18% w/w, or about 19% w/w, based on the total weight of the composition, excluding the weight of any coating.

The glidant(s) can be contained in the composition, for example, in a total amount ranging from about 0.1% w/w to about 9.0% w/w, based on the total weight of the composition, excluding the weight of any coating.

The glidant(s) can be contained in the composition, for example, in a total amount ranging from about 0.1% w/w to about 9.0% w/w, from about 0.1% w/w to about 8% w/w, from about 0.1% w/w to about 6% w/w, from about 0.1% w/w to about 4% w/w, from about 0.1% w/w to about 2.8% w/w, from about 0.1% w/w to about 2.6% w/w, from about 0.1% w/w to about 2.4% w/w, from about 0.1% w/w to about 2.2% w/w, from about 0.1% w/w to about 2.0% w/w, from about 0.1% w/w to about 1.8% w/w, from about 0.1% w/w to about 1.6% w/w, from about 0.1% to about 1.4% w/w, from about 0.1% w/w to about 1.2% w/w, from about 0.1% w/w to about 1.0% w/w, from about 0.1% w/w to about 0.8% w/w, from about 0.1% w/w to about 0.4% w/w, from about 0.2% w/w to about 3.0% w/w, from about 0.4% w/w to about 3.0% w/w, from about 0.6% w/w to about 3.0% w/w, from about 0.8% w/w to about 3.0% w/w, from about 1.0% w/w to about 3.0% w/w, from about 1.2% w/w to about 9.0% w/w, from about 1.4% w/w to about 9.0% w/w, from about 1.6% w/w to about 9.0%, from about 1.8% w/w to about 9.0% w/w, from about 2.0% w/w to about 9.0% w/w, from about 2.2% w/w to about 9.0% w/w, from about 2.4% w/w to about 9.0% w/w, from about 2.6% w/w to about 9.0% w/w, from about 2.8% w/w to about 9.0% w/w, from about 3.0% w/w to about 9.0% w/w, from about 4.0% w/w to about 9.0% w/w, from about 5.0% w/w to about 9.0% w/w, from about 6.0% w/w to about 9.0% w/w, from about 7.0% w/w to about 9.0% w/w, from about 8.0% w/w to about 9.0% w/w, from about 0.5% w/w to about 2.5% w/w, or from about 1.0% w/w to about 2.0% w/w, based on the total weight of the composition, excluding the weight of any coating.

The glidant(s) can be contained in the composition, for example, in a total amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.2% w/w, about 1.4% w/w, about 1.6% w/w, about 1.8% w/w, about 2.0% w/w, about 2.2% w/w, about 2.4% w/w, about 2.6% w/w, about 2.8% w/w, about 3% w/w, about 4% w/w, about 5% w/w, about 6% w/w, about 7% w/w, about 8% w/w, or about 9% w/w, based on the total weight of the composition, excluding the weight of any coating.

The lubricant(s) can be contained in the composition, for example, in a total amount ranging from about 0.1% w/w to about 3.0% w/w, based on the total weight of the composition, excluding the weight of any coating.

The lubricant(s) can be contained in the composition, for example, in a total amount ranging from about 0.1% w/w to about 2% w/w, about 0.1% w/w to about 1% w/w, from about 0.1% w/w to about 0.7% w/w, from about 0.1% w/w to about 0.6% w/w, from about 0.1% w/w to about 0.5% w/w, from about 0.1% w/w to about 0.4% w/w, from about 0.1% w/w to about 0.3% w/w, from about 0.1% w/w to about 0.2% w/w, from about 0.2% w/w to about 3.0% w/w, from about 0.3% w/w to about 3.0% w/w, from about 0.4% w/w to about 3.0% w/w, from about 0.5% w/w to about 3.0% w/w, from about 0.6% w/w to about 3.0% w/w, from about 0.7% w/w to about 3.0% w/w, from about 0.8% w/w to about 3.0% w/w, from about 0.9% w/w to about 3.0% w/w, from about 1% w/w to about 3.0% w/w, from about 2% w/w to about 3% w/w, from about 0.2% w/w to about 0.7% w/w, from about 0.3% w/w to about 0.6% w/w, or from about 0.4% w/w to about 0.5% w/w, based on the total weight of the composition, excluding the weight of any coating.

The lubricant(s) can be contained in the composition, for example, in a total amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 2.0% w/w, or about 3.0% w/w, based on the total weight of composition, excluding the weight of any coating.

In some embodiments, for example, the composition described herein comprises one or more fillers in a total amount ranging from about 3.5% w/w to about 55% w/w, one or more disintegrants in a total amount ranging from about 0.2% w/w to about 20% w/w, one or more glidants in a total amount ranging from about 0.1% w/w to about 9.0% w/w, and one or more lubricants in a total amount ranging from about 0.1% w/w to about 3.0% w/w.

In some embodiments, for example, the composition described herein comprises a filler, a disintegrant, a glidant, and a lubricant. In some embodiments, the filler is microcrystalline cellulose, the disintegrant is croscarmellose sodium, the glidant is colloidal silica anhydrous, and the lubricant is magnesium stearate. In other embodiments, the filler is microcrystalline cellulose, the disintegrant is croscarmellose sodium, the glidant is a combination of colloidal silica anhydrous and talc, and the lubricant is magnesium stearate.

The ingredients in the composition described herein can be, for example, homogeneous or heterogeneously mixed. The composition ingredients can be, for example, mixed by any known method including shaking, stirring, mixing with forced air, mixing in a spinning container, and the like. The composition ingredients can be, for example, mixed all at once, or with progressive addition of one or more ingredients. The composition ingredients can be mixed in any order, for example, individually, in groups, or as a blend of all of the ingredients.

For example, the glidant(s) can be mixed with the DMF and/or disintegrant(s) prior to mixing with any or all of the filler(s) and/or lubricants. The blend can also be prepared by mixing DMF, disintegrant(s) (e.g., croscarmellose sodium) and a portion of binder (e.g., microcrystalline cellulose) before then passing through a screen or sieve. The remaining binder can be mixed with lubricant(s) (e.g., magnesium stearate) before passing through a screen or sieve. These two mixtures can then be combined and mixed before adding glidant(s) (e.g., silica colloidal anhydrous). The glidant(s) can also be added to one or both of the aforementioned mixtures before they are combined and mixed to produce the final blend.

The composition described herein can have a flowability index, for example, ranging from about 8 mm to about 24 mm. For example, the flowability index can range from about 12 mm to about 22 mm, from about 12 mm to about 20 mm, from about 12 mm to about 18 mm, from about 12 mm to about 16 mm, from about 12 mm to about 14 mm, from about 14 mm to about 24 mm, from about 16 mm to about 24 mm, from about 18 mm to about 24 mm, from about 20 mm to about 24 mm, from about 22 mm to about 24 mm, from about 14 mm to about 22 mm, or from about 16 mm to about 20 mm.

The flowability index can be, for example, less than 18 mm (e.g., about 8 mm, about 12 mm, about 14 mm, about 16 mm) with an amount of glidant(s) ranging from about 0.1% w/w to about 2.0% w/w (e.g., 1.0% w/w).

The flowability index can be measured, for example, on a FLODEX device (manufactured by Hanson Research). The following protocol, for example, can be employed: A powder sample (e.g., 50 g) is loaded into the cylinder on the FLODEX device such that the powder is within about 1 cm from the top of the cylinder. A minimum of 30 seconds is allowed to pass before testing commences. Starting with a 16 mm flow disk, the release lever is slowly turned until the closure drops open without vibration. The test is positive when the open hole at the bottom is visible when looking down from the top. If a positive result is obtained, the test is repeated with smaller and smaller disk holes until the test is negative. For negative results, the size of the flow disk hole is increased until the test is positive. The flowability index is the diameter of the smallest hole through which the sample will pass for three successive tests.

The composition can have, for example, a compressibility index ranging from about 15% to about 28%. The compressibility index can range, for example, from 17% to about 28%, from about 19% to about 28%, from about 21% to about 28%, from about 23% to about 28%, from about 25% to about 28%, from about 15% to about 26%, from about 15% to about 24%, from about 15% to about 22%, from about 15% to about 20%, from about 15% to about 18%, from about 17% to about 26%, from about 19% to about 24%, or from about 20% to about 22%.

The composition can have a compressibility index, for example, of about 16%, about 17%, about 18%, about 19%, about 20%, about 21%, about 22%, about 23%, about 24%, about 25%, about 26%, or about 27%.

The compressibility index can be defined, for example, by the formula: $(((V_o-V_f)/V_o)\times 100\%)$ where $V_o$ is unsettled apparent volume of the particle and $V_f$ is the final tapped volume of the powder. The compressibility index can be determined, for example, as follows: powder is placed in a container and the powder's unsettled apparent volume ($V_o$) is noted. Next, the powder is tapped until no further volume changes occur. At this point, the final tapped volume of the powder is measured ($V_f$). The compressibility index is then calculated by using the formula above.

In some embodiments, the composition can be in the form of a powder (not compressed) or a compact (compressed). The shape of the compact is not limited and can be, for example, cubic, spherical, or cylindrical (e.g., disc-shaped).

The compact can be, for example, in the form of tablets, caplets, or microtablets. The compact can be prepared by any means known in the art. For example, if the compact is in the form of microtablets, the microtablets can be made by compressing the composition described above using any known method, such as using a rotary tablet press equipped with a multi-tip tooling and having concave tips.

Multi-tip tableting tools, for example, can be used. For example, a multi-tip tool having from about 16 tips to about 40 tips using, for example, about 2 mm diameter tips. In this situation, applied compressing force can be expressed as an average kN/tip. For example, an applied compressing force of 2 kN used with a 16 multi-tip tool yields an applied compressing force of about 0.125 kN/tip. Similarly, an applied compressing force of about 15 kN used with a 16 multi-tip tool yields an applied compressing force of about 0.94 kN per tip.

The microtablets can have a mean diameter (excluding any coatings), for example, ranging from about 1 mm to about 3 mm. For example, the microtablets can have a mean diameter ranging from about 1 mm to about 2.5 mm. The microtablets can have a mean diameter of about 1.0 mm, about 2.0 mm, or about 3.0 mm.

Compact tensile strength can be determined by any means known in the art. For example, the following protocol could be employed. First, compact(s) are compressed to about 360 mg weight using an instrumented rotary tablet press equipped to measure compression force with round flat tooling of approximately 10 mm diameter. Next, measure the diametrial crushing strength using a suitable tablet hardness tester and then calculate tensile strength by the procedure reported by Newton (Newton, J. M., *Journal of Pharmacy and Pharmacology*, 26: 215-216 (1974)). See also Pandeya and Puri, *KONA Powder and Particle Journal*, 30: 211-220 (2013), Jarosz and Parrott, *J. Pharm. Sci.* 72(5):530-535 (1983), and Podczeck, *Intl. J. Pharm.* 436: 214-232(2012).

The composition described herein, in the form of a compact, can have a tensile strength equal to or greater than 1.5 MPa at an applied or compaction pressure of about 100 MPa. For example, the tensile strength can range from about 2.0 to about 5.0 MPa (e.g., from about 2.5 to about 4.5 MPa, from about 3.0 to about 4.5 MPa or from about 3.5 to about 4.5 MPa) at an applied or compaction pressure of about 100 MPa. For example, the tensile strength can be about 4.0 MPa at an applied or compaction pressure of about 100 MPa.

The compact in the form of one or more microtablets produced using 16 multi-tip tooling can have a hardness or breaking strength or crushing strength ranging from about 8 N to about 35 N when the microtablet is formed by a compression force ranging from 2 kN to about 15 kN and the microtablet has a 2 mm diameter, a thickness of 2 mm, and a 1.8 mm radius of the convex surface. In one embodiment, microtablets each having a 2 mm diameter, a thickness of 2 mm, and a 1.8 mm radius of the convex surface have a hardness ranging from about 17 N to about 24 N for a compression force of about 4 kN to about 7 kN. The hardness can be, for example, of from about 23 N to about 27 N (e.g., about 24 N, about 25 N, or about 26 N) for a compression force of about 10 kN to about 15 kN. Hardness or breaking strength or crushing strength can be determined for example, using an Erweka tester or a Schleuniger tester as described in Lachman, L. et al., *The Theory & Practice of Industrial Pharmacology* (3rd ed. 1986), p. 298.

In some embodiments, the composition can be optionally coated or partially coated by one or more coatings. The coating(s) can be pH independent or pH dependent. The coating(s) can be, for example, enteric coatings, seal coatings, or combinations of enteric coatings and seal coatings.

The seal coating can contain, for example, one or more plasticizers, one or more copolymers, one or more polymers, or combinations thereof.

The plasticizer can be, for example, one or more of acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil an lanolin alcohols, palmitic acid, polyethylene glycol, polyvinyl acetate phthalate, propylene glycol, 2-pyrrolidone, sorbitol, stearic acid, triacetin, tributyl citrate, triethanolamine, and triethyl citrate.

The copolymer can be, for example, a methacrylic acid-methacrylate copolymer or a methacrylic acid-ethylacrylate copolymer.

Additionally, the seal coating can contain one or more polymers, for example, cellulose derivatives such as hydroxyethyl cellulose, hydroxypropyl cellulose, hydroxypropyl and methylcellulose, polyvinylpyrrolidone, a polyvinylpyrrolidone/vinyl acetate copolymer, ethyl cellulose, and ethyl cellulose aqueous dispersions (AQUACOAT®, SURELEASE®), EUDRAGIT® RL 30 D, OPADRY®, EUDRAGIT® S, EUDRAGIT® L, and the like.

If present in the seal coating, the total amount of one or more copolymer(s) and/or one or more polymer(s) in the seal coating can range, for example, from a positive amount greater than 0% w/w to about 100% w/w, based on the weight of the seal coating. The amount of one or more copolymer(s) and/or one or more polymer(s) in the seal coating can range, for example, from about 10% w/w to about 100% w/w, from about 20% w/w to about 100% w/w, from about 30% w/w to about 100% w/w, from about 40% w/w to about 100% w/w, from about 50% w/w to about 100% w/w, from about 60% w/w to about 100% w/w, from about 70% w/w to about 100% w/w, from about 80% w/w to about 100% w/w, or from about 90% w/w to about 100% w/w, based on the weight of the seal coating.

The amount of one or more copolymer(s) and/or one or more polymer(s) in the seal coating can be, for example, about 10% w/w, about 20% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, or about 95% w/w, based on the weight of the seal coating.

If present in the seal coating, the mean amount of plasticizer in the seal coating can range, for example, from a positive amount greater than 0% w/w to about 70% w/w, based on the weight of the seal coating.

The enteric coating can contain, for example, one or more plasticizers, one or more fillers, one or more lubricants, one or more copolymers, one or more polymers, and any combinations thereof.

The plasticizer(s) in the enteric coat can be the same or different than any plasticizer(s) in a seal coat, if present, and can be one of more of the plasticizers listed above.

The filler(s) in the enteric coat can be the same or different than any filler(s) in the composition. Additionally, the filler(s) in the enteric coat can be the same or different than any filler(s) in a seal coat, if present, and can be one or more of the fillers listed above.

The lubricant(s) in the enteric coat can be the same or different than any lubricant(s) in the composition. Additionally, the lubricant(s) in the enteric coat can be the same or different than the copolymer(s) in a seal coat, if present, and can be one or more of the lubricants listed above. In one embodiment, the lubricant is talcum that is optionally micronized.

The copolymer(s) in the enteric coat can be the same or different than the copolymer(s) in a seal coat, if present, and can be one or more of the copolymer(s) listed above.

In one embodiment, the enteric coat contains one or more of a methyl acrylate-methyl methacrylate-methacrylic acid copolymer (EUDRAGIT® FS 30 D), a methacrylic acid-methyl methacrylate copolymer and a methacrylic acid-ethyl acetate copolymer.

The enteric polymers used in the composition described herein can be modified by mixing or layering with other known coating products that are not pH sensitive. Examples of such coating products include ethyl cellulose, hydroxylpropyl cellulose, neutral methacrylic acid esters with a small portion of trimethylammonioethyl methacrylate chloride, sold currently under the trade names EUDRAGIT® RS and EUDRAGIT® RL; a neutral ester dispersion without any functional groups, sold under the trade names EUDRAGIT® NE 30 D; and other pH independent coating products.

The total amount of the copolymer(s) and/or polymer(s) in the enteric coating can range, for example, from about 25% w/w to about 100% w/w, based on the weight of the enteric coating.

If present in an enteric coating, the total amount of lubricant(s) in the enteric coating can range, for example, from a positive amount greater than 0% w/w to about 58% w/w, based on the weight of the enteric coating.

If present in an enteric coating, the total amount of filler(s) in the enteric coating can range, for example, from a positive amount greater than 0% w/w to about 5.0% w/w, based on the weight of the enteric coating.

Solvents for applying the coating materials, can be, but are not limited to, water, acetone, hexane, ethanol, methanol, propanol, isopropanol, butanol, isobutanol, sec-butanol, tert-butanol, dichlormethane, trichloromethane, chloroform, and the like.

Coatings can be applied by any known means, including spraying. In some embodiments, the compositions are coated or partially coated with one or more seal coatings, for example one, two, three or more seal coatings. In some embodiments, the compositions are coated or partially coated with one or more enteric coatings, for example one, two, three or more enteric coatings. In some embodiments, the compositions are coated with one or more seal coatings and one or more enteric coatings. In some embodiments, the compositions are coated with one seal coating and one enteric coating.

In a specific embodiment, the pharmaceutical composition is a tablet, for example, the tablet set forth in Table 2 and further coated with a seal coating solution and an enteric coating solution according to Formula A as set forth in Table 3 (See Example 1, Section 6.1 infra).

In a specific embodiment, the pharmaceutical composition is a tablet, for example, the tablet set forth in Table 2 and further coated with a seal coating solution and an enteric coating solution according to Formula B as set forth in Table 3 (See Example 1, Section 6.1 infra).

In a specific embodiment, the pharmaceutical composition is the same as in TECFIDERA®. In another specific embodiment, the pharmaceutical composition is the same as in FUMADERM®. In another specific embodiment, the pharmaceutical composition contains different fumarates from those fumarates in FUMADERM®.

In one embodiment, the pharmaceutical composition is in the form of a tablet or a capsule. In one embodiment, the pharmaceutical composition is in the form of an enterically coated tablet. In one embodiment, the pharmaceutical composition is in the form of an enterically coated microtablets.

5.3 Dosing Regimens

This disclosure provides dosing regimens for administering the fumarates as described herein. The fumarates and pharmaceutical compositions described herein may be administered by any means that achieve their intended purpose. For example, administration may be by parenteral, subcutaneous, intramuscular, intraperitoneal, transdermal, buccal, intrathecal, intracranial, intranasal, or topical routes. In one embodiment, the administering is done orally. The dosage administered will be dependent upon the age, health, and weight of the recipient, kind of concurrent treatment, if any, frequency of treatment, and the nature of the effect desired.

The amount of fumarate that can be combined with the carrier materials to produce a single dosage form will vary depending upon the host treated, and the particular mode of administration. It should be understood, however, that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of fumarate can also depend upon the therapeutic or prophylactic agent, if any, with which the agent is co-administered.

A composition comprising a total amount of dimethyl fumarate (DMF) ranging from about 43% w/w to about 95% w/w (e.g., from about 50% w/w to about 80% w/w or from about 60% w/w to about 70% w/w) and one or more excipients formulated in such a manner that about 160 mg of DMF to about 500 mg of DMF (e.g., about 240 mg to about 480 mg DMF) can be included in a single dosage form that can be administered, for example, once per day (QD), twice per day (BID), or thrice per day (TID). For example, a capsule (e.g., size 0) can contain about 240 mg of DMF. As another example, a capsule can contain about 480 mg of DMF.

When the fumarate is administered to a human, the compound may quickly metabolize to MMF. The pharmacokinetics properties (e.g., $C_{max}$ and AUC) can be therefore measured based on the concentration of MMF in the plasma after administration. The pharmacokinetics properties can be determined after single dosing or at steady state. In some embodiments, subjects orally administered a dosage form described above containing a fumarate or a pharmaceutically acceptable salt, clathrate, solvate, tautomer, or stereoisomer thereof exhibit a time to maximum plasma MMF concentration ($T_{max}$) of, for example, from about 1.5 hours to about 3.5 hours, from about 1.75 hours to about 3.25 hours, or from about 2 hours to about 2.5 hours.

In some embodiments, subjects orally administered a dosage form described above containing a fumarate exhibit a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In one embodiment, subjects exhibit a mean $AUC_{0-12}$ of about 3.93 h·mg/L.

In some embodiments, subjects orally administered a dosage form described above containing a fumarate exhibit a mean MMF plasma area under the curve 0-infinity ($AUC_{0\text{-}infinity}$) of about 2.4 h·mg/L to about 5.6 h·mg/L, from about 2.75 h·mg/L to about 5.10 h·mg/L, or from about 3.14 h·mg/L to about 4.91 h·mg/L. In one embodiment, subjects exhibit a mean $AUC_{0\text{-}infinity}$ of about 3.93 h·mg/L.

In some embodiments, subjects orally administered a dosage form described above containing a fumarate twice daily exhibit a mean MMF plasma overall area under the curve of about 4.81 h·mg/mL to about 11.2 h·mg/mL, or from about 6.40 h·mg/L to about 10.1 h·mg/L. In one embodiment, subjects exhibit a mean $AUC_{overall}$ of about 8.02 h·mg/L when orally administered the dosage forms twice daily.

In some embodiments, subjects orally administered a dosage form described above containing a fumarate exhibit a mean MMF plasma concentration ($C_{max}$) of from about 1.45 mg/L to about 3.39 mg/L, from about 1.69 mg/L to about 3.15 mg/L, or from about 1.93 mg/L to about 3.03 mg/L. In one embodiment, subjects exhibit a mean $C_{max}$ of about 2.42 mg/L.

In one embodiment, subjects orally administered a dosage form described above containing a fumarate exhibit a mean $C_{max}$ of about 1.02 mg/L to about 2.41 mg/L, or about 1.37 mg/L to about 2.15 mg/L. In one embodiment, subjects exhibit a mean $C_{max}$ of about 1.72 mg/L when orally administered the dosage forms twice daily.

Additionally, subjects orally administered a dosage form described above containing a fumarate can exhibit one or more of the following pharmacokinetic parameters: (a) a mean plasma MMF $T_{max}$ of from about 1.5 hours to about 3.5 hours; (b) a mean plasma MMF $C_{max}$ ranging from about 1.03 mg/L to about 3.4 mg/L; (c) a mean plasma MMF $AUC_{overall}$ ranging from about 4.81 h·mg/L to about 11.2 h·mg/L; (d) a mean plasma MMF $AUC_{0-12}$ ranging from about 2.4 h·mg/L to about 5.5 h·mg/L; and (e) a mean $AUC_{0\text{-}infinity}$ ranging from about 2.4 h·mg/L to about 5.6 h·mg/L.

In some embodiments, the compounds and pharmaceutical compositions described herein can be administered in an amount ranging from about 1 mg/kg to about 50 mg/kg (e.g., from about 2.5 mg/kg to about 20 mg/kg or from about 2.5 mg/kg to about 15 mg/kg). The amount of the compounds and pharmaceutical compositions described herein administered will also vary, as recognized by those skilled in the art, dependent on route of administration, excipient usage, and the possibility of co-usage with other therapeutic treatments including use of other therapeutic agents.

For example, the compounds and pharmaceutical compositions described herein can be administered to a subject, for example orally, in an amount of from about 0.1 g to about 1 g per day, or for example, in an amount of from about 100 mg to about 800 mg per day.

The amount of compounds and pharmaceutical compositions described herein may be administered once a day or in separate administrations of 2, 3, 4, 5 or 6 equal doses per day.

In addition to administering the agent as a raw chemical, the agents described herein may be administered as part of a pharmaceutical preparation containing suitable pharmaceutically acceptable carriers comprising excipients and auxiliaries which facilitate processing of the agents into preparations which may be used pharmaceutically. For example, the preparations, particularly those preparations which may be administered orally, such as tablets, dragees, and capsules, and also preparations which may be administered rectally, such as suppositories, as well as suitable solutions for administration by injection or orally, contain from about 0.01 to 99 percent, preferably from about 0.25 to 75 percent of fumarate(s), together with the excipient.

In one embodiment, the composition is in the form of a dosage form, such that one composition provides the total DMF dose. In other embodiments, the dosage form contains multiple compositions to provide the total DMF dose. For example, a dosage form may contain multiple compacts, such as microtablets, to provide the desired total DMF dose.

If the dosage form contains multiple compacts, such as multiple microtablets, to provide the required total DMF dose, the compacts in the dosage form can differ from one another. For example, the dosage form can contain two or more different microtablet types (e.g., the capsule can contain one group of microtablets coated with only an enteric coating and a second group of microtablets coated with only a seal coating, or one group coated with an enteric coating with a lower pH release and the other coated with an enteric coating with a higher pH release).

In some embodiments, the composition is placed in a capsule. In other embodiments, the composition, in the form of microtablets, is placed in a capsule. The capsule can contain, for example, from about 30 microtablets to about 60 microtablets, from about 35 microtablets to about 55 microtablets, from about 30 to about 50 microtabletes or from about 40 microtablets to about 50 microtablets (e.g., about 44, about 45, about 46, about 47, or about 48 microtablets).

The dosage form can be administered, for example, once, twice, thrice, four time, five times, or six times per day. One or more dosage form can be administered, for example, for one, two, three, four, five, six, or seven days. One or more dosage forms can be administered, for example, for one, two, three, or four weeks. One or more dosage forms can be administered, for example, for one, two, three, four, five, six, seven, eight, nine, ten, eleven, twelve months or longer. One or more dosage forms can be administered until the subject in need thereof does not require treatment, prophylaxis, or amelioration of any disease or condition such as, for example, multiple sclerosis.

In some embodiments, a method described herein comprises orally administering a dosage form that provides a total amount of about 60 mg to about 1000 mg of dimethyl fumarate daily. The dosage form can, for example, contain a total amount of DMF effective for treatment, prophylaxis, or amelioration of multiple sclerosis in a subject. The daily effective amount can range, but is not limited to, a total amount of about 60 mg to about 800 mg DMF, about 60 mg to about 720 mg DMF, 60 mg to about 500 mg DMF, about 60 mg to about 480 mg DMF, about 60 mg to about 420 mg DMF, about 60 mg to about 360 mg DMF, about 60 mg to about 240 mg DMF, about 60 mg to about 220 mg DMF, about 60 mg to about 200 mg DMF, about 60 mg to about 180 mg DMF, about 60 mg to about 160 mg DMF, about 60 mg to about 140 mg DMF, about 60 mg to about 120 mg DMF, about 60 mg to about 100 mg DMF, about 60 mg to about 80 mg DMF, about 80 mg to about 480 mg DMF, about 100 mg to about 480 mg DMF, about 120 mg to about 480 mg DMF, about 140 mg to about 480 mg DMF, about 160 mg to about 480 mg DMF, about 180 mg to about 480 mg DMF, about 200 mg to about 480 mg DMF, about 220 mg to about 480 mg DMF, about 240 mg to about 480 mg DMF, about 300 mg to about 480 mg DMF, about 360 mg to about 480 mg DMF, about 400 mg to about 480 mg DMF, about 450 mg to about 500 mg DMF, about 480 mg to about 500 mg DMF, about 80 to about 400 mg DMF, about 100 to about 300 mg DMF, about 120 to about 180 mg DMF, or about 140 mg to about 160 mg DMF.

The dosage form can contain, but is not limited to, a total amount of DMF of about 60 mg DMF, about 80 mg DMF, about 100 mg DMF, about 120 mg DMF, about 140 mg DMF, about 160 mg DMF, about 180 mg DMF, about 200 mg DMF, about 220 mg DMF, about 240 mg DMF, about 260 mg DMF, about 280 mg DMF, about 300 mg DMF, about 320 mg DMF, about 340 mg DMF, about 360 mg DMF, about 380 mg DMF, about 400 mg DMF, about 420 mg DMF, about 450 mg DMF, about 480 mg DMF, about 500 mg DMF, about 520 mg DMF, about 540 mg DMF, about 560 mg DMF, about 580 mg DMF, about 600 mg DMF, about 620 mg DMF, about 640 mg DMF, about 660 mg DMF, about 680 mg DMF, about 700 mg DMF, about 720 mg DMF, about 740 mg DMF, about 760 mg DMF, about 780 mg DMF or about 800 mg DMF.

In some embodiments, DMF is the only active ingredient in the pharmaceutical composition. In one embodiment, the pharmaceutical composition consists essentially of DMF.

For the treatment of multiple sclerosis (e.g., relapsing forms of multiple sclerosis such as RR-MS), the dosage form administered to the subject can be a capsule with microtablets containing DMF as the only active ingredient or microtablets consisting essentially of DMF, wherein the effective amount is about 480 mg DMF per day, and the subjects can receive the effective amount, i.e., 240 mg DMF BID, in the form of two capsules a day, to be taken orally.

For the treatment of multiple sclerosis (e.g., relapsing forms of multiple sclerosis such as RR-MS), the dosage form administered to the subject can be a capsule with microtablets containing DMF as the only active ingredient or microtablets consisting essentially of DMF, wherein the effective amount is about 720 mg DMF per day, and the subjects can receive the effective amount, i.e., 240 mg DMF TID, in the form of three capsules a day, to be taken orally. In one embodiment, the therapeutically effective amount is 240 mg twice daily.

In a specific embodiment of the methods described herein, the fumarate is DMF and the dose of DMF is 120 mg DMF BID administered orally for the first 7 days. In certain embodiments, the dose is increased to the maintenance dose of 240 mg DMF BID (i.e., 480 mg DMF per day) administered orally. In another embodiment, the dose is increased to 240 mg DMF TID (i.e., 720 mg DMF per day) administered orally. In one embodiment, the administering is of 120 mg twice daily for 7 days, followed by 240 mg twice daily as a maintenance dose.

In a specific embodiment, the fumarate is DMF, and the dose of DMF is 120 mg DMF BID administered orally for at least 7 days, followed by a maintenance dose of 240 mg DMF BID administered orally.

In a specific embodiment, the fumarate is DMF, and the dose of DMF is 240 mg DMF BID administered orally.

DMF is known to cause flushing and gastrointestinal (GI) side effects in certain subjects. While the side effects generally subside soon after subjects start on the treatment, in a specific embodiment, the starting dose is 120 mg DMF BID orally for the first 7 days. The dose can be increased to 240 mg DMF BID (i.e., 480 mg DMF per day). In other embodiments, the dose can be increased to 240 mg DMF TID (i.e., 720 mg DMF per day). In certain embodiments, the fumarate is administered with food. In other embodiments, the fumarate is administered without food. For those subjects who experience GI or flushing side effects, administering a fumarate, for example, DMF, with food improves tolerability. In one embodiment, administering a fumarate, such as DMF, with food reduces the incidence of flushing.

In a specific embodiment, a NSAID (e.g., aspirin) is administered concurrently, before, and/or after administration of the fumarate (e.g., DMF). In a healthy volunteer study, administration of 325 mg non-enteric coated aspirin 30 minutes prior to DMF dosing is found to reduce the occurrence and severity of flushing in the participating subjects. Some subjects who experience flushing with gastrointestinal side effects may reduce the dose to 120 mg DMF BID temporarily. Within a month, the effective dose of 240 mg DMF BID or 240 mg DMF TID should be resumed.

In one embodiment, subjects administered a dosage form described above may take one or more non-steroidal anti-inflammatory drugs (e.g., aspirin) before (for example, 10 minutes to an hour, e.g., 30 minutes before) taking the dosage form described above. In one embodiment, the subject administered the dosage form takes the one or more non-steroidal anti-inflammatory drugs (e.g., aspirin) to reduce flushing. In another embodiment, the one or more non-steroidal anti-inflammatory drugs is selected from a group consisting of aspirin, ibuprofen, naproxen, ketoprofen, celecoxib, and combinations thereof. The one or more non-steroidal anti-inflammatory drugs can be administered in an amount of about 50 mg to about 500 mg before taking the dosage form described above. In one embodiment, a subject takes 325 mg aspirin before taking each dosage form described above.

In some embodiments, subjects orally administered one or more non-steroidal anti-inflammatory drugs (e.g., aspirin) before taking the dosage form described above exhibit the same pharmacokinetic properties (e.g., $C_{max}$ and AUC) as subjects orally administered the dosage form described above without administering one or more non-steroidal anti-inflammatory drugs (e.g., aspirin).

In one embodiment, subjects with multiple sclerosis are administered a capsule containing 240 mg DMF, twice daily for a total daily dose of 480 mg, wherein the capsule contains multiple microtablets comprising about 43% w/w to about 95% w/w (e.g., from about 50% to about 80% w/w) DMF, by weight of the microtablets without any coatings. In another embodiment, subjects having multiple sclerosis are administered a capsule containing 240 mg DMF, thrice daily for a total daily dose of 720 mg, wherein the capsule contains multiple microtablets comprising about 43% w/w to about 95% w/w (e.g., from about 50% to about 80% w/w) DMF, by weight of the microtablets without any coatings. In one embodiment, the microtablets are first coated with a seal coat and then coated with an enteric coat. In one embodiment, the subjects administered the capsular dosage form exhibit one or more of the pharmacokinetic parameters described above.

5.4 Progressive Multifocal Leukoencephalopathy (PML)

Progressive multifocal leukoencephalopathy (PML) is an opportunistic brain infection caused by the JC virus (JCV). PML occurs primarily in immunocompromised individuals and in patients receiving certain immunomodulatory therapies, including natalizumab.

PML is hypothesized to be the result of a complex interaction between host and viral factors, leading to reactivation and mutation of latent archetype JCV to a neurotrophic form which can infect oligodendrocytes in the central nervous system.

In a specific embodiment, the invention provides for monitoring patients and withholding treatment with a fumarate described herein, such as dimethyl fumarate (e.g., TECFIDERA®), at the first sign or symptom suggestive of PML, and optionally performing an appropriate diagnostic evaluation.

5.4.1 Monitoring a Sign or Symptom Suggestive of PML

In specific embodiments, the invention provides for monitoring a MS patient that is being treated with a fumarate for the first sign or symptom suggestive of PML. Typical symptoms associated with PML are diverse and progress over days to weeks. Sign or symptoms suggestive of PML include, but are not limited to the following typical symptoms: progressive weakness on one side of the body, clumsiness of limbs, disturbance of vision, and changes in thinking, memory, and orientation leading to confusion and personality changes. Mental function, speech, and movement may also be affected. Additional symptoms may include ataxia, loss of cognitive function, visual loss, changes in balance and coordination, and loss of sensation. The progression of deficits usually leads to death or severe disability over weeks or months.

Unlike multiple sclerosis, in PML involvement of the spinal cord or optic nerves rarely occurs. Instead, about one-third of patients have visual field loss or cortical blindness, while another third will show altered mentation or behavior changes (Dworkin et al., Curr. Clin. Top. Infect. Dis., 2002, 22:181-195). Also unlike multiple sclerosis, hemiparesis is a common symptom. These symptoms are typically sub-acute at onset, and slowly progress. Often, patients and their families are the first to notice the onset of PML through changes in the ability to perform routine activities of daily living, even before changes on neurological examination (see WO 2007/100770 at paragraph [094]).

In certain embodiments, a patient with multiple sclerosis who is being treated with a fumarate is monitored for a sign or symptom suggestive of PML in the patient.

In certain embodiments, the treatment with the fumarate is withheld from the patient at the first sign or symptom suggestive of PML in the patient.

In one embodiment, the methods provided herein further comprise performing a diagnostic evaluation for PML in the patient at the first sign or symptom suggestive of PML in the patient.

5.4.2 Performing Diagnostic Evaluation for PML

In specific embodiments, the invention provides performing a diagnostic evaluation for PML in the patient at the first sign or symptom suggestive of PML in the patient.

The diagnostic evaluation can be by any method known in the art, including but not limited to magnetic resonance imaging (MRI), detection of JC viral DNA in the cerebrospinal fluid (CSF), detection of consistent white matter lesions by MRI, assessing the progressive course of disease, or a combination of any of the foregoing.

In a specific embodiment, PML is diagnosed based on a combination of (1) detection of JC viral DNA in CSF; (2) consistent white matter lesions shown by MRI, and optionally (3) progressive course of the disease.

As described in WO 2007/100770, the pathology of PML is distinctive, involving foci of demyelination of varying size from pinpoint lesions to areas of several centimeters.

Lesions generally appear in the cerebral hemispheres, less often in the cerebellum and brain stem and rarely in the spinal cord, although they can appear elsewhere. The oligodendrocytes in the peripheral zone surrounding an area of demyelination appear grossly abnormal. The nuclei of these abnormal oligodendrocytes contain many JC virions.

Certain clinical features of PML help distinguish it from the demyelination associated with multiple sclerosis.

5.4.2.1. Magnetic Resonance Imaging (MRI)

Magnetic Resonance Imaging (MRI) can be used to diagnose PML. As shown in Table 1, there are features of PML lesions that help differentiate them from other etiologies (Post et al., Am. J. Neuroradiol., 1999, 20(10):1896-1906; Yousry et al., N. Engl. J. Med., 2006, 354(9):924-933; Berger et al., Ann. Neural., 1998, 44(3):341-349; Hoffmann et al., J. Neural. Neurosurg. Psychiatry, 2003, 74(8):1142-1144; Langer-Gould et al., N Engl. J. Med., 2005, 353(4):375-381).

In a specific embodiment, the diagnostic evaluation for PML in a patient involves detection of consistent white matter lesions by MRI.

Table 1. Differential Diagnosis of multiple sclerosis and PML (as taken from WO 2007/100770 at pp 29-30)

TABLE 1

Differential Diagnosis of multiple sclerosis and PML (as taken from WO 2007/100770 at pp 29-30)

|  | Multiple Sclerosis | PML |
|---|---|---|
| Location of new lesions | Mostly focal, may affect entire brain and spinal cord, in white and possibly gray matter; Posterior fossa lesions rarely seen | Diffuse, mainly sub-cortical, rarely periventricular, almost exclusively in white matter, although occasional extension to gray matter seen; Posterior fossa frequently involved (cerebellum) |

TABLE 1-continued

Differential Diagnosis of multiple sclerosis and PML (as taken from WO 2007/100770 at pp 29-30)

| | Multiple Sclerosis | PML |
|---|---|---|
| Borders | Sharp edges, shapes mostly round or finger-like (especially periventricular), confluent with other single lesions, U-fibers may be involved | Ill-defined edges, infiltrating, irregular in shape, confined to white matter, sparing gray matter, pushing against cortex, U-fibers destroyed |
| Mode of extension | Focal, enlarging of lesions within days/weeks, later decreasing in size within months | Diffuse, asymmetrical, extending homogeneously, no confluence with other lesions, defined to white matter tracks, sparing cortex, continuous progression |
| Mass effect | Acute lesions may show some mass effect | No mass effect even in large lesions (but process is slightly pushing against cortex) |
| T2-weighted sequence | Acute lesions: hyperintense center, isointense ring, discrete hyperintensity outside ring structure; Sub-acute/chronic lesions: hyperintense no ring structure | Diffuse hyperintense, slightly increased intensity of newly involved areas compared to old areas, little irregular signal intensity of lesions |
| T1-weighted sequence | Acute lesions: densely hypointense (large lesion) or isointense (small lesion), increasing signal intensity over time in 80% decreasing signal intensity (axonal loss) in about 20% | Slightly hypointense from the onset, signal intensity decreasing over time and along the affected area, no reversion of signal intensity |
| Flair sequence | Hyperintense, sharply delineated | Hyperintensity more obvious, true extension of abnormality more clearly visible than in T2-weighted images |
| Enhancement | Acute lesions: dense homogeneous enhancement, sharp edges Sub-acute lesions: ring-enhancement Chronic lesions: no enhancement | Usually no enhancement even in large lesions, in HIV+ patients some peripheral enhancement possible, especially under therapy |
| Atrophy | Focal atrophy possible due to focal white matter degeneration, no progression | No focal atrophy since extending pathological process is slightly pushing against cortex (extension of tissue) |

5.4.2.2. Histological and Virological Examination

In a specific embodiment, the diagnostic evaluation comprises a test for the presence of JC viral DNA in the CSF of the patient. PCR analysis of the cerebrospinal fluid (CSF) for JC viral DNA is a highly sensitive and specific test for the diagnosis of PML. The specificity of this test approaches 100%, with a sensitivity ranging from 60% to 90% (Henson et al., Neurology, 1991, 41(12):1967-1971; Gibson et al., J. Med. Virol., 1993, 39(4):278-281; Weber et al., AIDS, 1994, 8(1):49-57; Weber et al., J. Infect. Dis., 1994, 169(5):1138-1141; Vago et al., J. Acquir. Imm. Defic. Syndr. Hum. Retrovirol., 1996, 12(2):139-146). In cases with a high clinical suspicion of PML and negative CSF results, repeat testing often leads to detection of JC viral DNA. Thus, PCR analysis of the CSF for JC viral DNA is a useful method for diagnosing PML.

In one embodiment, the diagnostic evaluation further comprises a test for the presence in the patient of antibodies to JCV. In one aspect, the diagnostic evaluation for PML in the patient involves evaluating the level of anti-JCV antibody in a biological sample from the patient. In general, antibodies to JCV in the blood of patients treated with a fumarate may be indicative of risk of future PML, but are not themselves diagnostic of PML.

In one aspect, the diagnostic evaluation for PML in the patient involves evaluating a patient's risk of developing PML by a method comprising a test for the presence in the patient of antibodies to JCV. In one aspect, the diagnostic evaluation for PML in the patient involves evaluating a patient's risk of developing PML by a method comprising a test evaluating the level of anti-JCV antibody in a biological sample from the patient.

A wide variety of serological tests are available to detect JCV, e.g., complementfixation (CFT), haemagglutination-inhibition (HAI), enzyme-linked immunoassay (EIA), radio-immunoassay (RIA), particle agglutination, immunofluorescence (IF), single radial hemolysis, and Western blot. The sensitivity and specificity varies greatly between different techniques. Most techniques will detect all classes of antibody, whereas some assays e.g., RIA, EIA, and IF can be designed to detect one specific class, for example, IgM, IgG, or IgA.

In certain embodiments, the patient is tested for JCV in the patient's urine, blood, and/or cerebrospinal fluid (CSF). In a specific embodiment, the testing comprises serially removing samples of the patient's blood, measuring the amount of IgG antibodies to JCV in the samples, and comparing the amount of the antibodies in the samples over time. In other specific embodiments, the testing includes measuring the amount of IgM antibodies to JCV in the samples, and comparing the amount of IgM and IgG antibodies in the samples.

In certain embodiments, the testing detects seroconversion and/or an increasing titer of JCV in the patient's urine and/or blood, and further includes removing a sample of the patient's cerebrospinal fluid when the comparison of the serial urine and/or blood samples detect seroconversion and/or an increasing titer of JCV; and testing the cerebrospinal fluid for the presence of JCV antibodies.

In one embodiment, the diagnostic evaluation comprises testing for clinical and/or radiologic symptoms of PML. In certain embodiments, the testing for clinical symptoms comprises testing for new or worsening neurological symptoms. In specific embodiments, the neurological symptoms comprise one or more of central blindness, mental confusion, personality change, and dyskinesia. In other embodiments, the testing for radiologic symptoms of PML comprises performing a Gd-enhanced magnetic resonance imaging scan.

In one embodiment, testing tests for JCV in the patient's urine, blood, and/or cerebrospinal fluid. In a specific embodiment, the monitoring comprises serially removing samples of the patient's blood, measuring the amount of IgG antibodies to JCV in the samples, and comparing the amount of the antibodies in the samples over time. In some embodiments, the testing further comprises measuring the amount of IgM antibodies to JCV in the samples, and comparing the amount of the IgM and IgG antibodies in the samples. In one embodiment, the monitoring detects seroconversion and/or an increasing titer of JCV in the patient's urine and/or blood by removing a sample of the patient's cerebrospinal fluid when the comparison of the serial urine and/or blood samples detect seroconversion and/or an increasing titer of JCV; and testing the cerebrospinal fluid for the presence of JCV.

In one aspect, the diagnostic evaluation for PML in the patient involves evaluating a patient's risk of developing PML by a method comprising determining a JCV antibody titer in a biological sample from the patient, wherein the patient has a negative prior immunosuppressant exposure classification; wherein if the titer is determined to be above a pre-determined level, e.g., above an index level of 0.7, 0.8, 0.9, 1.0, 1.1, 1.2, 1.3, 1.4, or 1.5, the patient is determined to be at a higher risk of developing PML, and wherein if the titer is determined to be at or below a pre-determined level, e.g., at or below an index level of 1.5, 1.4, 1.3, 1.2, 1.1, 1.0, 0.9, 0.8, or 0.7, the patient is determined to be at a lower risk of developing PML.

In one aspect, the diagnostic evaluation for PML in the patient involves evaluating a patient's risk of developing PML by a method comprising determining a JCV antibody titer in two or more biological samples obtained from the patient over a period of time (e.g., 2, 3, 4, 5, 6, 7, 8, 9, 10, 11, 12, 13, 14, 15, 16, 17, 18, 19, 20, 21, 22, 23, 24 or more months); wherein if the titer is determined to be above zero, but at or below a pre-determined level, e.g., at or below an index level of 1.5, 1.4, 1.3, 1.2, 1.1, 1.0, 0.9, 0.8, or 0.7, in the two or more samples, the patient is determined to be at a lower risk of developing PML, and wherein if the titer is determined to be above a pre-determined level, e.g., above an index level of 0.7, 0.8, 0.9, 1.0, 1.1, 1.2, 1.3, 1.4, or 1.5, in the two or more samples, the patient is determined to be at a higher risk of developing PML.

In one aspect, the diagnostic evaluation for PML in the patient involves determining a patient's risk of developing PML by a method comprising evaluating the level of anti-JCV antibody in a biological sample. The method comprises one or more or all of the following steps (see WO 2012/166971):

(a) forming a first reaction mixture comprising a first aliquot of sample and a substrate on which is disposed HPVLP (Highly Purified Virus-Like Particle consisting predominantly of the JCV major capsid protein VP1);

(b) detecting the level of anti-JCV antibody bound to said substrate on which is disposed HPVLP, e.g., by detecting a labeled detection reagent, e.g., an enzyme labeled anti-IgG antibody, bound to anti-JCV antibody bound to said substrate; thereby evaluating the level of anti-JCV antibody in a sample (the method can comprise classifying, or assigning, to the sample, a value indicative of the level of anti-JCV antibody, which can be used in embodiments, to determine whether to proceed to an additional step of the method, e.g., step (c) below); and (c) forming a second reaction mixture containing a second aliquot of sample and solution-phase HPVLP, and detecting the level of unbound anti-JCV antibody in said second reaction mixture, such as by detecting anti-JCV antibody capable of binding with a substrate on which is disposed HPVLP (the method can comprise classifying, or assigning, to the sample, a value indicative of the degree to which incubation with the soluble-phase HPVLP reduces the level of unbound anti-JCV antibody in the second reaction mixture, which value can be referred to as inhibition, % inhibition, or the like), thereby evaluating the level of anti-JCV antibody in the sample.

In an embodiment, the method further comprises (see WO 2012/166971): (d) forming a third reaction mixture containing a third aliquot under conditions where anti-JCV antibodies in the sample are not bound by HPVLP or other antigen, and detecting the level of anti-JCV antibody in the third reaction mixture, such as by detecting anti-JCV antibody capable of binding with a substrate on which is disposed HPVLP. The inhibition or % inhibition can be calculated as a function of the degree that incubation with soluble-phase HPVLP (step (c)) reduces the amount of unbound anti-JCV antibody, as compared to the result in step (d).

In one aspect, the diagnostic evaluation for PML in the patient involves a method of evaluating a patient's risk of developing PML, the method comprising:

determining a JC Virus (JCV) antibody titer expressed as nOD, index or other unit, or other characteristics such as affinity or avidity expressed as percent inhibition in the anti-JCV antibody confirmation assay in a biological sample from the patient, and comparing the titer or/and percent inhibition, or function of both values, to a pre-determined level.

In one embodiment, a method of evaluating a patient's risk of developing PML further includes testing the serum or plasma of the sample for both IgG and IgM antibodies to JCV and initiating treatment with a fumarate if the serum or plasma is negative for both IgG and IgM antibodies to JCV.

5.4.3 Treating PML

The cellular receptor for JCV has been reported to be the serotonin 5-HT$_{2A}$ receptor (Elphick et al., Science, 2004, 306(5700):1380-1383). It has also been suggested that the 5HT2 antagonist mirtazapine may be useful in the prophylaxis or treatment of PML (Verma et al., J Infect Dis., 2007, 196(5):709-711).

Hexadecyloxypropyl-Cidofovir (CMX001) has also been studied as a treatment option for JCV (Gosert et al., Antimicrob. Agents Chemother., 2011, 55(5):2129-2136) because of its ability to suppress JVC by inhibiting viral DNA replication.

Mefloquine has been reported to block JCV replication without significant toxicity, and at concentrations achievable in the central nervous system. Although cases of successful PML treatment with mefloquine in HIV and non-HIV infected patients have been reported (e.g., Young et al., Ann. Acad. Med. Singap., 2012, 41(12):620-624), unsuccessful cases of mefloquine use for treatment of PML have also been reported (Clifford et al., J. Neurovirol., 2013, 19:351-358; Tyler et al., J. Neurovirol., 2013, 19(4):311-313).

In accordance with the methods provided herein, when the diagnostic evaluation for PML indicates PML in the patient or an elevated risk of the patient for developing PML, a method of the invention can further comprise administering a therapeutic to the patient for the treatment or prevention of PML. Such therapeutic can be any therapeutic known in the art. Currently, there is no established drug treatment for PML. However, various medications have been tested, including acyclovir, idoxuridine, vidarabine, amantadine, adenine arabinoside, cytosine arabinoside (cytarabine, also known as ARA-C), cidofovir, interferon a, interleukin-2 (IL-2), zidovudine, camptothecin, topotecan, mefloquine, and mirtazapine (Koralnik, Curr. Opt. Neurol., 2004, 17(3):365-370; Dworkin et al., Curr. Clin. Top. Infect. Dis., 2002, 22:181-195; Seth et al., J. Neurovirol., 2003, 9(2):236-246; Collazos, CNS Drugs, 2003, 17(12):869-887; Mamidi et al., J. Neurovirol., 2002, 8(3):158-167; Przepiorka et al., Bone Marrow Transplant, 1997, 20(11):983-987; Redington et al., Arch. Neural., 2002, 59(5):712-718; Padgett et al., Prog. Clin. Biol. Res., 1983, 105:107-117). Thus, in a specific embodiment, such a therapeutic can be HAART, acyclovir, idoxuridine, vidarabine, amantadine, adenine arabinoside, cytosine arabinoside (cytarabine, also known as ARA-C), cidofovir, interferon a, interleukin-2 (IL-2), zidovudine, camptothecin, topotecan, chlorpromazine, clozapine. zisprasidone, risperidone, olanzapine, hexadecyloxypropyl-Cidofovir (CMX001), mefloquine, or mirtazapine.

In one embodiment, the methods provided herein include, when a diagnostic evaluation indicates the presence of PML, providing at least one treatment of PML selected from intravenous immunoglobulin therapy, plasmapheresis, and antiviral therapy. In certain embodiments, the antiviral therapy comprises the administration of at least one therapeutically effective dose of an antiviral agent selected from cytosine arabinoside (cytarabine), cidofovir, and a serotonin antagonist.

Provided herein is a method of using a fumarate described herein to treat a patient with multiple sclerosis by removing a sample of blood from the patient; testing the serum or plasma of the sample for the presence of IgG antibodies to JCV; initiating treatment of the patient with the fumarate in the event the sample is negative for IgG antibodies to JCV; monitoring the patient for signs or symptoms of progressive multifocal leukoencephalopathy; and discontinuing the administration of the fumarate in the presence of signs or symptoms of PML.

In one aspect, an entity, e.g., a healthcare provider, acquires information resulting from an anti-JCV antibody assay described herein, and responsive to the information, administers a treatment described herein to the patient.

In another aspect, a JCV assay described herein is performed on a patient, and then the patient is treated based on the results of the assay. Thus, for example, if the assay is negative for JCV, treatment with a fumarate continues or is initiated, or re-initiated (if fumarate has been withheld at the first sign or symptom of PML)

5.5 Complete Blood Count

In specific embodiments, the invention provides for obtaining a complete blood count (CBC) including lymphocyte count after 6 months of repeated administering of a pharmaceutical composition described herein (e.g., TECFIDERA®) to a MS patient, and every 6 to 12 months thereafter. In one embodiment, the administering of the pharmaceutical composition (e.g., TECFIDERA®) is interrupted when the patient has a lymphocyte count less than $0.5 \times 10^9$/L persisting for more than six months. In a specific embodiment, the invention provides for measuring of lymphocyte count in the patient until lymphopenia is resolved in the patient.

A CBC, also known as a complete blood cell count, full blood count (FBC), or full blood exam (FBE), is a blood test. A CBC provides information about the three general types of cells circulating in the bloodstream: white blood cells (leukocytes), red blood cells (erythrocytes), and platelets (thrombocytes). A CBC measures red blood cells, white blood cells, hemoglobin, hematocrit, and platelets. Evaluation of white blood cells in a CBC panel may include a white blood cell count, which is the total number of white blood cells in a person's sample of blood, and may also include white blood cell differential, which identifies and counts the various types of white blood cells such as lymphocytes, monocytes, neutrophils, eosinophils, and basophils. Evaluation of red blood cells in a CBC panel may include a total red blood cell count, hemoglobin, hematocrit, mean corpuscular volume (MCV), mean corpuscular hemoglobin (MCH), mean corpuscular hemoglobin concentration (MCHC), red blood cell distribution width (RDW), and reticulocyte count. Platelet evaluation in a CBC test may include platelet count, mean platelet volume (MPV), and platelet distribution width (PDW). Abnormally high or low counts of a particular type of cell in the bloodstream may indicate the presence of an underlying medical condition.

A CBC can be conducted by using methods well known in the art, which may comprise collecting the blood sample through venipuncture, drawing the blood into a test tube containing an anticoagulant, and counting the blood cells using manual techniques or an automated analyzer (see, e.g., Buttarello and Plebani, Am. J. Clin. Pathol., 2008, 130(1): 104-116).

In controlled and uncontrolled clinical trials of TECFIDERA®, 2% of patients experienced lymphocyte counts less than $0.5 \times 10^9$/L for at least six months. In these patients, the majority of lymphocyte counts remained less than $0.5 \times 10^9$/L with continued therapy. 5.6 Patient Populations As used herein, the terms "patient" and "subject" can be used interchangeably. The fumarate as described herein is administered to a subject in need thereof, a subject having MS. In a specific embodiment, said subject has been diagnosed as having MS by a medical practitioner.

In some embodiments, the form of the multiple sclerosis is relapsing remitting, secondary progressive, primary progressive, or chronic progressive multiple sclerosis. In one embodiment, the patient with multiple sclerosis is a patient with a relapsing form of MS. In a specific embodiment, the patient has relapse-remitting MS (RR-MS). In another specific embodiment, the patient has secondary-progressive MS (SP-MS). In yet another specific embodiment, the patient has progressive-relapsing MS (PR-MS).

In one embodiment, the patient is not pregnant. In another embodiment, the patient is not a nursing mother.

In one embodiment, the patient has no hypersensitivity to a fumarate, such as dimethyl fumarate, administered in the methods described herein. In a further embodiment, the patient has no hypersensitivity to the fumarate, such as dimethyl fumarate, or does not know about his hypersensitivity to the fumarate.

In one embodiment, the patient is not treated simultaneously with both one or more fumarates (e.g., dimethyl fumarate) and any immunosuppressive or antineoplastic medication. In certain embodiments, the patient is not treated simultaneously with a fumarate (e.g., dimethyl fumarate) and any immunosuppressive or immunomodulatory medications or natalizumab. In certain embodiments, the patient is not treated simultaneously with a fumarate described herein (e.g., dimethyl fumarate) and any medications carrying a known risk of causing progressive multifocal leukoencephalopathy (PML).

In one embodiment, the patient has never been treated with a fumarate, e.g., dimethyl fumarate, prior to commencement of therapy in accordance with the methods disclosed herein. In another embodiment, the patient has not been treated with a fumarate, e.g., dimethyl fumarate, 1, 2, 3, 4, 6, 8, 10, or 12 months or 1, 2, 3, 5, 10, 20, 30, 40, or 50 years, prior to commencement of therapy in accordance with the methods disclosed herein.

In one embodiment, the patient has never been treated with any immunosuppressive or antineoplastic medication prior to commencement of therapy in accordance with the methods disclosed herein. In a further embodiment, the patient has not been treated with any immunosuppressive or antineoplastic medication 1, 2, 3, 4, 6, 8, 10, or 12 months or 1, 2, 3, 5, 10, 20, 30, 40, 50 years, prior to commencement of therapy in accordance with the methods disclosed herein. In another embodiment, the patient has never been treated with any immunosuppressive or immunomodulatory medications or natalizumab prior to commencement of therapy in accordance with the methods disclosed herein. In yet another embodiment, the patient has not been treated with any immunosuppressive or immunomodulatory medications or natalizumab 1, 2, 3, 4, 6, 8, 10, or 12 months or 1, 2, 3, 5, 10, 20, 30, 40, or 50 years, prior to commencement of therapy in accordance with the methods disclosed herein. In another embodiment, the patient has never been treated with any medications carrying a known risk of causing PML prior to commencement of therapy in accordance with the methods disclosed herein. In yet another embodiment, the patient has not been treated with any medications carrying a know risk of causing PML 1, 2, 3, 4, 6, 8, 10, or 12 months or 1, 2, 3, 5, 10, 20, 30, 40, or 50 years, prior to commencement of therapy in accordance with the methods disclosed herein.

In one embodiment, the immunosuppressive or antineoplastic medication is selected from one or more of: chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, flurorodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, edroxyprogesterone, megestrol, raloxifene, letrozole, anastrzole, flutamide, bicalutamide, retinoic acids, arsenic trioxide, rituximab, CAMP ATH-1, mylotarg, mycophenolic acid, tacrolimus, glucocorticoids, sulfasalazine, glatiramer, fumarate, laquinimod, FTY-720, interferon tau, daclizumab, infliximab, ILIO, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

In one embodiment, the immunosuppressive or immunomodulatory medication is selected from one or more of: calcinerurin inhibitors, corticosteroids, cytostatics, nitrosoureas, protein synthesis inhibitors, dactinomycin, anthracyclines, mithramycin, polyclonal ntibodies such as atgum and thymoglobulin, monoclonal antibodies such as muromonab-CD3, and basiliximab, ciclosporin, sirolimus, rapamycin, γ-interferon, opioids, TNF binding proteins, TNF-α binding proteins, etanercept, mycophenolate, fingolimode, and myriocin.

In one embodiment, the patient being treated in accordance with the methods described herein has no identified systemic medical condition resulting in a compromised immune system function.

In one embodiment, the patient has been free of an immunosuppressant or immunomodulatory therapy for the patient's lifetime, or since diagnosis with MS, for example a relapsing form of MS.

6. EXAMPLES

6.1 Example 1: Compositions of Dimethyl Fumarate

A pharmaceutical composition comprising dimethyl fumarate was prepared as 2 millimeter enteric coated microtablets in a size 0 hard gelatin capsule. Each capsule contained either 120 mg dimethyl fumarate or 240 mg dimethyl fumarate.

6.1.1 Uncoated Core Microtablet Formulations

Dimethyl fumarate (DMF), croscarmellose sodium, talc, and colloidal silica anhydrous were mixed together to form a blend according to the amounts as described in Table 2. The blend was then passed through a screen (e.g., screen with 800 micron aperture) and microcrystalline cellulose (PROSOLV SMCC® HD90) was added to the blend and mixed. Magnesium stearate was added to the blend and the blend was remixed. The resulting blend was then compressed on a suitable rotary tablet press equipped with 16 multi-tip tooling having 2 mm round concave tips.

Table 2 below provides the weight percentages of ingredients present in two types of microtablets, 120 mg DMF and 240 mg DMF, respectively, made using the method described above. Microtablets were coated as described in Section 6.1.2 and then loaded into capsules. A size 0 capsule containing microtablets made with blend A contains about 120 mg of DMF, whereas the same size capsule containing microtablets made with blend B contains about 240 mg of DMF.

TABLE 2

| Ingredients | Blend A | | Blend B, % w/w | |
|---|---|---|---|---|
| | Composition, % w/w | Per microtablet content (mg) | Composition, % w/w | Per microtablet content (mg) |
| DMF | 42 | 3.1 | 65 | 5.2 |
| Croscarmellose sodium | 5 | 0.37 | 5 | 0.4 |
| Prosolv SMCC® HD90 | — | — | 29 | 2.3 |
| Avicel PH200 | 44 | 3.2 | — | — |
| Magnesium Stearate | 1.7 | 0.12 | 0.5 | 0.04 |
| Talc | 6.6 | 0.49 | — | — |
| Silica colloidal anhydrous | 0.86 | 0.067 | 0.6 | 0.048 |
| Total | 100 | 7.4 | 100 | 8 |

6.1.2 Microtablet Coating Formulations

The microtablets were coated with two coatings; a seal coating, followed by an enteric coating, using the seal coating formulation and enteric coating formulation of Formula A and Formula B as described in Table 3. The seal coating formulation was a solvent-based formulation which used isopropyl alcohol as a solvent, and the enteric coating formulation was based on methyl acrylic acid copolymer dispersion and provided effective enteric protection. The enteric coating formulation contained methacrylic acid copolymer dispersion and talc in addition to an antifoaming agent (simethicone). The coated microtablets were then loaded into size 0 hard gelatin capsules.

TABLE 3

| Ingredients | Coating Formula A, % w/w | Coating Formula B, % w/w |
|---|---|---|
| Seal Coating Formulation | | |
| Methacrylic acid copolymer, Type A[2] | 44.0 | 51.7 |
| Triethyl citrate | 1.1 | 1.3 |
| Isopropyl alcohol[1] | 54.9 | 47.1 |
| Enteric Coating Formulation | | |
| Methacrylic acid copolymer dispersion[2] | 36.9 | 44.3 |
| Triethyl citrate | 2.2 | 2.6 |
| Talc, micronized | 4.6 | 5.5 |
| Simethicone (30% emulsion) | 0.2 | 0.2 |
| Purified water[1] | 59.0 | 47.3 |

[1]Ingredients are removed during the process
[2]Methacrylic acid copolymer Type A and methacrylic acid copolymer dispersion are anionic copolymers comprising methacrylic acid and methacrylate and are the primary substances in various EUDRAGIT ® formulations, which mediate pH-dependent release of compounds.

6.2 Example 2: Formation of Capsules Containing Microtablets

Dimethyl fumarate, croscarmellose sodium, talcum and colloidal silicon anhydrous are mixed together to form a blend according to the amounts described in Table 4 below. The blend is passed through a screen. A suitable grade of microcrystalline cellulose, for example, PROSOLV SMCC® 90 or PROSOLV SMCC® HD90 is added to the blend and mixed. Magnesium stearate is added to the blend and the blend is remixed.

The blend is then compressed on a suitable rotary tablet press equipped with multi-tip tooling (e.g., a 16 multi-tip tooling) having 2 mm round concave tips. The resulting 2 mm sized microtablets are coated with a solution of methacrylic acid-methyl methacrylate copolymer and triethyl citrate in isopropanol (see amounts in Table 4 below). The coated microtablets are then coated with a second layer of coating consisting of methacrylic acid-ethylacrylate copolymer, polysorbate 80, sodium lauryl sulfate, triethyl citrate, simethicone, and talcum micronized suspended in water (see amounts in Table 4 below).

The desired amount of coated microtablets are encapsulated in a two piece hard gelatin capsule using a capsule machine. For example, coated microtablets are encapsulated in a capsule such that the amount of dimethyl fumarate is about 240 mg per capsule.

In Table 4 below, % w/w is based on the total weight of the coated microtablet (e.g., in this table, % w/w includes the weight contributions of the coatings).

TABLE 4

| | Net capsule content, % w/w of the capsule components Example No. | | | | | | | | | |
|---|---|---|---|---|---|---|---|---|---|---|
| Ingredients | 1 | 2 | 3 | 4 | 5 | 6 | 7 | 8 | 9 | 10 |
| Dimethyl fumarate | 43.01 | 72.30 | 58.40 | 54.08 | 83.60 | 73.90 | 39.50 | 65.00 | 33.90 | 42.00 |
| Croscarmellose sodium | 1.26 | 0.33 | 3.72 | 4.17 | 0.46 | 0.89 | 4.43 | 4.00 | 4.24 | 3.00 |
| Microcrystalline Cellulose | 41.82 | 15.91 | 17.31 | 23.57 | 7.00 | 9.42 | 31.31 | 13.66 | 37.18 | 35.79 |
| Magnesium Stearate | 1.05 | 0.25 | 0.69 | 0.41 | 0.26 | 0.63 | 1.32 | 0.40 | 1.41 | 0.48 |
| Silica colloidal anhydrous | 1.21 | 0.22 | 0.78 | 0.97 | 0.43 | 0.29 | 0.69 | 0.40 | 0.73 | 0.68 |
| Methacrylic acid methyl acrylate copolymer | 1.01 | 1.27 | 0.98 | 1.51 | 0.11 | 1.66 | 1.87 | 1.21 | 1.55 | 1.32 |
| Methacrylic acid ethyl acrylate copolymer | 6.23 | 4.98 | 11.12 | 8.97 | 4.34 | 8.21 | 9.93 | 7.72 | 9.04 | 9.98 |
| Triethyl citrate | 1.61 | 1.74 | 2.33 | 2.12 | 0.97 | 1.67 | 2.31 | 2.09 | 2.15 | 2.32 |
| Talc | 2.56 | 2.81 | 4.32 | 3.90 | 2.65 | 3.06 | 8.32 | 5.30 | 9.46 | 4.12 |
| Simethicone | 0.03 | 0.02 | 0.03 | 0.05 | 0.02 | 0.03 | 0.02 | 0.02 | 0.06 | 0.02 |
| polysorbate 80 | 0.15 | 0.11 | 0.24 | 0.20 | 0.11 | 0.18 | 0.22 | 0.14 | 0.21 | 0.21 |
| Sodium Lauryl sulfate | 0.06 | 0.06 | 0.08 | 0.07 | 0.05 | 0.06 | 0.08 | 0.06 | 0.06 | 0.08 |

6.3 Example 3: Formation of Microtablets

Dimethyl fumarate, croscarmellose sodium, talcum and colloidal silicon anhydrous were mixed together to form blends 1, 2, 4, 5, and 6 according to the amounts described in Table 5 below. Each blend was passed through a screen. Microcrystalline cellulose (PROSOLV SMCC® HD90) was added to the blends according to the amounts in Table 5 and mixed. Magnesium stearate was then added to each blend and the blend was remixed. Each blend was then compressed on a suitable rotary tablet press equipped with 16 multi-tip tooling having 2 mm round concave tips.

Blends 3, 7, 8, and 9 can be made using the same method as described above.

TABLE 5

Percent w/w Composition of the Core Microtablet

| Ingredient | Blend 1 | Blend 2 | Blend 3 | Blend 4 | Blend 5 | Blend 6 | Blend 7 | Blend 8 | Blend 9 |
|---|---|---|---|---|---|---|---|---|---|
| Dimethyl fumarate | 42.0 | 42.0 | 50.0 | 60.0 | 65.0 | 70.0 | 75.0 | 85.0 | 95.0 |
| Croscarmellose sodium | 5.0 | 5.0 | 3.0 | 5.0 | 5.0 | 5.0 | 1.0 | 1.0 | 0.4 |
| Microcrystalline Cellulose | 44.0 | 50.0 | 43.0 | 32.0 | 28.3 | 23.0 | 22.0 | 13.0 | 4.0 |
| Magnesium Stearate | 1.7 | 1.7 | 0.5 | 1.7 | 0.5 | 1.3 | 0.4 | 0.4 | 0.4 |
| Silica colloidal anhydrous | 0.9 | 1.2 | 1.5 | 1.0 | 1.2 | 0.9 | 0.6 | 0.5 | 0.5 |
| Talc | 6.6 | — | 2.0 | — | — | — | 1.0 | — | — |
| total | 100 | 100 | 100 | 100 | 100 | 100 | 100 | 100 | 100 |

6.4 Example 4: Compacts Containing 42% w/w, 60% w/w, and 70% w/w Dimethyl Fumarate and Control Compacts Dimethyl fumarate, croscarmellose sodium, and silica colloidal anhydrous were blended together to form a blend. The blend was passed through a screen. A suitable grade of microcrystalline cellulose was added to the screened blend and the blend was mixed. A suitable grade of microcrystalline cellulose, is, for example PROSOLV SMCC® 90, having an average particle size by laser diffraction of about 60 μm and a bulk density ranging from about 0.38 to about 0.50 g/cm$^3$. Magnesium stearate was added to the mixed blend and remixing was effected.

The respective blended materials were compressed on a suitable rotary press (e.g., a rotary tablet press) to form compacts (10 mm cylindrical compacts).

Table 6 provides percentages for representative compacts made by this process.

TABLE 6

| Ingredients | 42% | 60% | 70% |
|---|---|---|---|
| Dimethyl fumarate | 42 | 60 | 70 |
| Croscarmellose sodium | 5.0 | 5.0 | 5.0 |
| Microcrystalline Cellulose | 50 | 32 | 23 |
| Magnesium Stearate | 1.7 | 1.7 | 1.7 |
| Silica colloidal anhydrous | 1.2 | 1.0 | 0.9 |

6.5 Example 5: Compositions Containing 65% w/w, 95% w/w. and 99.5% w/w Dimethyl Fumarate Four DMF-containing blends were prepared according to the method as described in Example 4 above with the amounts as described in Table 7 below.

TABLE 7

| | Composition, % by weight | | | |
|---|---|---|---|---|
| Ingredients | Blend 93 | Blend 97 | Blend 104 | Blend 108 |
| Dimethyl fumarate | 65 | 95 | 99.5 | 95 |
| Prosolv SMCC 90 | 28.9 | 2 | — | 2 |
| Croscarmellose Sodium | 5 | 2 | — | 2 |
| Silica colloidal, anhydrous | 0.6 | 0.6 | — | 0.6 |

TABLE 7-continued

| | Composition, % by weight | | | |
|---|---|---|---|---|
| Ingredients | Blend 93 | Blend 97 | Blend 104 | Blend 108 |
| Magnesium stearate | 0.5 | 0.4 | 0.5 | 0.4 |
| Particle size of dimethyl fumarate | 14% <250μ | 14% <250μ | 15% <250μ | 84% <250μ |
| Flodex (mm) | 4 | 4 | 4 | 6 |
| Bulk density (g/ml) | 0.66 | 0.66 | 0.74 | 0.69 |
| Tapped density(g/ml) | 0.79 | 0.78 | 0.83 | 0.83 |
| Compressibility, % | 17 | 16 | 17 | 17 |

6.6 Example 6: Instructing the Patient

By way of example, but not limitation, instructions in a TECFIDERA® label can be as follows:

Warnings and Precautions

Progressive Multifocal Leukoencephalopathy

Monitor patients and withhold TECFIDERA® at the first sign or symptom suggestive of PML and perform an appropriate diagnostic evaluation. Typical symptoms associated with PML are diverse, progress over days to weeks, and include progressive weakness on one side of the body or clumsiness of limbs, disturbance of vision, and changes in thinking, memory, and orientation leading to confusion and personality changes. The progression of deficits usually leads to death or severe disability over weeks or months.

Patient Counselling Information

Progressive Multifocal Leukoencephalopathy

Inform patients that progressive multifocal leukoencephalopathy (PML) has occurred in a patient who received TECFIDERA©. Instruct the patient of the importance of contacting their doctor if they develop any symptoms suggestive of PML. Instruct the patient that typical symptoms associated with PML are diverse, progress over days to weeks, and include progressive weakness on one side of the body or clumsiness of limbs, disturbance of vision, and changes in thinking, memory, and orientation leading to confusion and personality changes.

Instruct the patient that the progression of deficits usually leads to death or severe disability over weeks or months.

Instruct patients to continue to look for new signs and symptoms suggestive of PML for approximately 6 months following discontinuation of TECFIDERA® [see WARNINGS AND PRECAUTIONS].

6.7 Example 7: Instructing the Patient—Lymphopenia and Lymphocyte Counts

By way of example, but not limitation, instructions in a TECFIDERA® label can be as follows:

Warnings and Precautions

Lymphopenia

Before initiating treatment with TECFIDERA®, a CBC including lymphocyte count should be obtained. A CBC including lymphocyte count should also be obtained after 6 months of treatment, every 6 to 12 months thereafter, and as clinically indicated. Consider interruption of TECFIDERA® in patients with lymphocyte counts less than 0.5× $10^9$/L persisting for more than six months. Given the potential for delay in lymphocyte recovery after discontinuation of TECFIDERA®, consider following lymphocyte counts until lymphopenia is resolved. Withholding treatment should be considered in patients with serious infections until the infection(s) is resolved. Decisions about whether or not to restart TECFIDERA® should be individualized based on clinical circumstances.

Patient Counselling Information Lymphocyte Counts

Inform patients that TECFIDERA© may decrease lymphocyte counts. A blood test should be obtained before they start therapy. Blood tests are also recommended after 6 months of treatment, every 6 to 12 months thereafter, and as clinically indicated.

6.8 Example 8: Characterization of Absolute Lymphocyte Count Profiles in MS Patients Treated with Delayed-Release Dimethyl Fumarate: Considerations for Patient Management Delayed-release dimethyl fumarate (DMF; also known as gastro-resistant DMF, and as TECFIDERA®) demonstrated robust efficacy on clinical and neuroradiological measures and an acceptable safety profile in relapsing-remitting multiple sclerosis (RRMS) in clinical trials including a Phase 2b study, the Phase 3 DEFINE and CONFIRM studies, and the ENDORSE extension study.[1-6]

In clinical trials, DMF was associated with flushing and gastrointestinal events as well as decreased white blood cell (WBC) and absolute lymphocyte counts (ALCs).[7]

ALC profiles were characterized in DMF-treated MS patients in this study. Patients at greater risk for developing severe prolonged lymphopenia were identified. The study also evaluated DMF efficacy in patients with and without lymphopenia.

Objective

The objective of the analysis was to provide practical considerations for management of DMF (as TECFIDERA®)-treated MS patients by characterizing ALC profiles and examining efficacy in patients with and without lymphopenia enrolled in clinical trials (Phase 2b, DEFINE, CONFIRM, and ENDORSE).

Methods

Study Design

The Phase 2b study, DEFINE, and CONFIRM were multicenter, randomized, double-blind, placebo-controlled, parallel-group clinical trials of DMF as monotherapy for RRMS.

The Phase 2b study was 12 months in duration, including a 6-month placebo-controlled part (Part 1) and a 6-month uncontrolled safety extension part (Part 2). During Part 1, patients were randomized equally to DMF 120 mg once daily (QD), 120 mg three times daily (TID), 240 mg TID, or placebo.

DEFINE and CONFIRM were 2 years in duration. Patients were randomized equally to DMF 240 mg twice daily (BID), 240 mg TID, or matching placebo.

CONFIRM also included glatiramer acetate (GA) as a reference comparator arm.

ENDORSE is a multicenter, parallel-group, dose-blinded extension of DEFINE/CONFIRM with up to 8 additional years of follow-up.

Patients who received 240 mg DMF BID or TID for up to 2 years in the parent studies remained on the same DMF dosage in ENDORSE.

Patients who received placebo (DEFINE and CONFIRM) or GA (CONFIRM) in the parent studies were randomized equally to 240 mg DMF BID or TID.

Key Inclusion and Exclusion Criteria

Key inclusion and exclusion criteria for the Phase 2b study, DEFINE, and CONFIRM are summarized in Table 8.

TABLE 8

Key inclusion and exclusion criteria

Key inclusion criteria

Age 18-55 years
Diagnosis of RRMS per McDonald criteria[8]
EDSS score of 0-5.0

Key exclusion criteria

Progressive forms of MS or other significant illness
Relapse within 50 days prior to randomization
Corticosteroids within 30 days (Phase 2b) or 50 days (DEFINE, CONFIRM) prior to randomization
Pre-specified abnormal laboratory parameters including
WBC <3.5 × $10^9$/L or eosinophils >0.7 × $10^3$/μL or >0.7 GI/L
Prior treatment with potent immunosuppressant agents or procedures
Prior treatment with MS therapies within predefined washout periods, including interferon beta, within 3 months prior to randomization; GA, within 3 months prior to randomization (Phase 2b, DEFINE) or at any time (CONFIRM); or natalizumab, within 6 months prior to randomization Abbreviations:
EDSS, Expanded Disability Status Scale;
GA, glatiramer acetate;
WBC, white blood cell.

Hematology

In the Phase 2b study, blood was collected every 4 weeks.

In DEFINE and CONFIRM, blood was collected every 4 weeks for the first 3 months and every 12 weeks thereafter, and within 1 month after study withdrawal or study completion if not continuing in the extension study.

In ENDORSE, blood was collected at baseline and every 12 weeks thereafter

Hematology included hemoglobin, hematocrit, red blood cell count, WBC count (with differential), and platelet count.

ALCs were graded per Common Terminology Criteria for Adverse Events (CTCAE; Table 9).[9]

TABLE 9

CTCAE v4.0 grading for ALCs

| CTC grade 0 | CTC grade 1 | CTC grade 2 | CTC grade 3 | CTC grade 4 |
|---|---|---|---|---|
| >LLN[a] | <LLN-≥0.8 × $10^9$/L | <0.8-≥0.5 × $10^9$/L | <0.5-≥0.2 × $10^9$/L | <0.2 × $10^9$/L |

ALC = absolute lymphocyte count;
CTCAE = Common Terminology Criteria for Adverse Events
[a]Lower limit of normal (LLN) = 0.91 × $10^9$/L Statistical Analysis Data from DEFINE and CONFIRM after subjects switched to alternative MS treatment were excluded.

Data from the 6-month uncontrolled safety extension of the Phase 2b study were included.

A data cut-off date was used.

Results

Patients

The safety population comprised 2513 MS patients, including 1136 treated with DMF 240 mg BID, 1249 treated with DMF 240 mg TID, and 128 treated with lower doses of DMF (Table 10). Mean (SD) time on study treatment amounted to 3.1 (2.2) years (Table 10).

A total of 2470 patients had any post-baseline ALC.

TABLE 10

Time on study treatment

|  | Total DMF[a,b] (n = 2513) |
|---|---|
| Time on study treatment, mean (SD) years[c] | 3.1 (2.2) |
| Total number of cumulative patient-years of exposure to study treatment | 7249.96 |
| Patients on study treatment for at least, n (%) |  |
| 3 months | 2218 (88) |
| 6 months | 2099 (84) |
| 1 year | 1869 (74) |
| 2 years | 1602 (64) |
| 3 years | 1377 (55) |
| 4 years | 1001 (40) |
| 5 years | 740 (29) |
| 6 years | 270 (11) |
| 7 years | 34 (1) |

SD = standard deviation
[a]DMF, delayed-release DMF (also known as gastro-resistant DMF, and as TECFIDERA ®)
[b]Includes DMF 240 mg BID, DMF 240 mg TID, and lower doses of DMF (120 mg QD or TID)
[c]Each year comprised 48 weeks.

Mean WBC and ALCs Over Time with Continuing DMF Treatment

Mean baseline ALCs were similar across the groups treated with DMF 240 mg BID, DMF 240 mg TID, or lower doses of DMF (FIG. 1).

Mean ALCs decreased by approximately 30% during the first year of treatment, then plateaued, remaining above the lower limit of normal (LLN; 910/mm$^3$) throughout the observation period (FIG. 1).

Incidence of CTC grade 0-4 lymphopenia

For the majority of patients, ALCs were within normal limits at all time points (CTC grade 0).

The incidence of worst post-baseline CTC grades 0, 1, 2, and 3 or 4 is shown in Table 11.

TABLE 11

Incidence of CTC grades for worst post-baseline ALCs

| n (%) | Total DMF[a,b] (n = 2513) |
|---|---|
| CTC grade 0 | 1533 (61) |
| CTC grade 1 | 236 (9) |
| CTC grade 2 | 528 (21) |
| CTC grade 3 or 4[c] | 173 (7) |
| No post-baseline ALC | 43 (2) |

CTC = Common Terminology Criteria
[a]DMF, delayed-release DMF (also known as gastro-resistant DMF, and as TECFIDERA ®)
[b]Includes DMF 240 mg BID, DMF 240 mg TID, and lower doses of DMF (120 mg QD or TID)
[c]2 patients (<1%) had CTC grade 4

ALC Profiles

ALCs remained greater than or equal to LLN in 84% of patients during the first 6 months and in 76% of patients during the first year; of these patients, 0.1% and 0%, respectively, developed ALCs less than 500/mm$^3$ persisting for greater than or equal to 6 months at any time (Table 12).

Among patients treated for greater than or equal to 6 months (N=2,099), 2.2% (n=47) experienced ALCs less than 500/mm$^3$ persisting for greater than or equal to 6 months, ALCs generally remained less than 500/mm$^3$ with continued therapy.

TABLE 12

Proportion of patients who subsequently developed ALCs <500/mm$^3$ persisting ≥6 months at any time (up to 7 years after initiating treatment) according to ALCs within the first 6 months or first 1 year of DMF treatment

| | n/N (%) | |
|---|---|---|
| All ALCs ≥LLN[b] | 3/2083 (0.1) | 0/1876 (0) |
| All ALCs ≥800/mm$^3$ | 9/2219 (0.4) | 0/2050 (0) |
| All ALCs ≥500/mm$^3$ | 37/2446 (1.5) | 16/2409 (0.7) |
| At least 1 ALC <500/mm$^3$ | 38/251 (10) | 47/420 (17) |
| At least 1 ALC <500/mm$^3$ | 10/24 (42) | 31/61 (51) |

ALC = absolute lymphocyte count
[b]Lower limit of normal (LLN) = 0.91 × $10^9$/L Time Course of Mean ALC Changes in Patients with ALCs <500/mm$^3$ Persisting ≥6 Months Mean ALCs in the subgroup of patients with ALCs less than 500/mm$^3$ persisting for greater than or equal to 6 months showed a faster decline compared with mean counts in the subgroup of patients without less than 500/mm$^3$ persisting for greater than or equal to 6 months (FIG. 2A and FIG. 2B).

Recovery of ALCs Post-Discontinuation of DMF Treatment

Among the 47 patients with ALCs less than 500 cells/µL for at least 6 months, 9 patients discontinued or completed the study. Of the 9 patients, 8 had ALCs measured at least 1 month after their final dose. All 9 patients showed increases in ALCs following their final dose of DMF (FIG. 3). The remaining 38 patients remained on treatment at the time of this analysis; however, a protocol amendment for ENDORSE went into effect six months later and stipulated that study treatment must be temporarily withheld if ALC is less than 500/mm$^3$ for more than 6 months. While dosing is withheld, patients will be followed every 4 weeks until the ALC is greater than or equal to LLN or for 24 weeks after the last dose (whichever is sooner). If ALC remains to be less than 500/mm$^3$ for 24 weeks after the last dose, then study treatment must be permanently discontinued.

Efficacy in Patients with Lymphopenia (<LLN) Versus Patients without Lymphopenia Reduction in annualized relapse rate (ARR) at 2 years in patients treated with DMF 240 mg BID versus placebo was not substantially different in patients with lymphopenia (at least 1 ALC less than LLN) versus patients without lymphopenia (all ALCs greater than LLN) in DEFINE and CONFIRM (FIGS. 4A-4B). In DEFINE (FIG. 4A), the rate ratio (95% CI) for adjusted ARR for DMF versus placebo was 0.424 (0.294, 0.611) and 0.509 (0.381, 0.681) in patients with and without treatment-associated lymphopenia, respectively. In CONFIRM (FIG. 4B), the rate ratio (95% CI) for adjusted ARR for DMF versus placebo was 0.525 (0.365, 0.756) and 0.599 (0.429, 0.835) in patients with and without treatment-associated lymphopenia, respectively.

Baseline characteristics including EDSS score, age, region, and number of relapses in the 1 year prior to study entry were similar across the placebo and DMF groups in patients with or without lymphopenia.

General Safety

As identified in this interim analysis of the Phase 2b, DEFINE, CONFIRM, and ENDORSE clinical studies, lymphopenia in DMF-treated patients was not associated with an overall increased risk of infections or serious infections, including opportunistic infections (Table 13). Subsequent to the data cut-off for this interim report, a case of PML in a patient treated with DMF 240 mg TID was reported in the setting of severe, prolonged lymphopenia (approximately less than $0.5 \times 10^9$/L of 3.5 years duration).

TABLE 13

Incidence of serious infections by worst post-baseline CTC grade

| Serious infections,[c] n (%) | Total DMF[a,b] (n = 2513) |
|---|---|
| CTC grade 0 | 43 (3) |
| CTC grade 1 | 13 (5.5) |
| CTC grade 2 | 22 (4) |
| CTC grade 3 or 4 | 5 (3) |

ALC, absolute lymphocyte count;
CTC, Common Terminology Criteria.
[a]DMF, delayed-release DMF (also known as gastro-resistant DMF, and as TECFIDERA®)
[b]Includes DMF 240 mg BID, DMF 240 mg TID, and lower doses of DMF (120 mg QD or TID)
[c]For each CTC grade, numbers in parentheses are percentages based on the number with an infection out of the number with worst post-baseline count in that grade as shown in Table 11.

CONCLUSIONS

ALC profiles are well characterized and stable over time. Mean ALCs decreased by approximately 30% in DMF-treated patients during the first year of treatment, then plateaued, remaining above LLN throughout the observation period.

ALCs remained greater than or equal to LLN in 84% of patients during the first 6 months and in 76% of patients during the first year; of these patients, 0.1% and 0%, respectively, developed ALCs less than 500/mm³ persisting for greater than or equal to 6 months at any time.

Among patients treated for at least 6 months, a small proportion (2.2%) experienced ALCs less than 500/mm³ persisting for greater than or equal to 6 months and this finding was an early predictor for those patients at greater risk for subsequently developing severe, prolonged lymphopenia.

Aside from a single case of PML in the setting of severe, prolonged lymphopenia, there is no overall increased risk for serious infections, including other opportunistic infections.

Before initiating treatment with DMF, a recent CBC including lymphocytes (i.e., within 6 months) should be available. A CBC including lymphocytes is also recommended after 6 months of treatment, every 6 to 12 months thereafter, and as clinically indicated.[7] As indicated in the product labelling, consider interruption of DMF in patients with ALCs less than $0.5 \times 10^9$/L persisting for more than 6 months. Following interruption of DMF, ALCs should be followed until lymphopenia is resolved.[7]

Although the data are limited, there is evidence of ALC improvement following discontinuation of DMF treatment.

Therapeutic efficacy of DMF both in patients with lymphopenia and in patients without lymphopenia suggests that lymphopenia is not a primary mechanism of action of DMF. Efficacy in patients with and without lymphopenia suggests that lymphopenia is not a primary mechanism of action of DMF.

The overall benefit-risk of DMF remains favorable. Together with clinical and neuroradiologic efficacy, these data continue to support DMF as a valuable long-term treatment option for patients with RRMS.

REFERENCES FOR EXAMPLE 8

1. Kappos L, Gold R, Miller D H, et al. *Lancet* 2008; 372:1463-1472.
2. Gold R, Kappos L, Arnold D L, et al. *N Engl J Med* 2012; 367:1098-1107.
3. Fox R J, Miller D H, Phillips J T, et al. *N Engl J Med* 2012; 367:1087-1097.
4. Gold R, Phillips J T, Bar-Or A, et al. Five-year follow-up of delayed-release dimethyl fumarate in RRMS: integrated clinical efficacy data from the DEFINE, CONFIRM, and ENDORSE studies. Poster presented at: Joint ECTRIMS-ACTRIMS Meeting; Sep. 10-13, 2014; Boston Mass. P110.
5. Arnold D L, Fox R J, Havrdova E, et al. Five-year follow-up of delayed-release dimethyl fumarate in relapsing-remitting multiple sclerosis: MRI outcomes from DEFINE, CONFIRM, and ENDORSE. Poster presented at: Joint ECTRIMS-ACTRIMS Meeting; Sep. 10-13, 2014; Boston Mass. P059.
6. Pozzilli C, Phillips J T, Fox R J, et al. Long-term follow-up of the safety of delayed-release dimethyl fumarate in RRMS: interim results from the ENDORSE extension study. Poster presented at: Joint ECTRIMS-ACTRIMS Meeting; Sep. 10-13, 2014; Boston Mass. P066.
7. TECFIDERA™ (dimethyl fumarate) [prescribing information]. Biogen Idec. Cambridge, Mass. Rev 12/2014.
8. Polman C H, Reingold S C, Edan G, et al. *Ann Neurol* 2005; 58:840-846.
9. National Cancer Institute. Common Terminology Criteria for Adverse Events v4.0, NCI, NIH, DHHS. May 29, 2009. NIH publication #09-7473.

6.9 Example 9: Instructing the Patient—Summary of Product Characteristics

By way of example, but not limitation, instructions for TECFIDERA® use in a Summary of Product Characteristics can be as follows:

Special Warnings and Precautions for Use
Blood/Laboratory Tests

Changes in renal and hepatic laboratory tests have been seen in clinical trials in subjects treated with TECFIDERA®. The clinical implications of these changes are unknown. Assessments of renal function (e.g. creatinine, blood urea nitrogen and urinalysis) and hepatic function (e.g. ALT and AST) are recommended prior to treatment initiation, after 3 and 6 months of treatment, every 6 to 12 months thereafter and as clinically indicated.

TECFIDERA® may decrease lymphocyte counts. TECFIDERA® has not been studied in patients with pre-existing low lymphocyte counts and caution should be exercised when treating these patients. Prior to initiating treatment with TECFIDERA®, a current complete blood count, including lymphocytes, must be performed. If lymphocyte count is found to be below the normal range, alternative causes of lymphopenia should be considered and corrective measures taken as appropriate. After starting therapy, complete blood counts, including lymphocytes, must be performed every 3 months. Treatment should be discontinued if lymphocyte count <$0.7\times10^9$/L is confirmed on repeat testing (at 3 months). Lymphocyte counts should be followed until recovery.

Progressive Multifocal Leukoencephalopathy (PML)

PML cases have occurred with TECFIDERA© in the setting of severe and prolonged lymphopenia. PML is an opportunistic infection caused by John-Cunningham virus (JCV), which may be fatal or result in severe disability. PML is likely caused by a combination of factors. Risk factors include an altered or weakened immune system and potentially further genetic or environmental risk factors.

Patients with lymphocyte counts <$0.5\times10^9$/L were observed in <1% of patients treated with placebo and 6% of patients treated with TECFIDERA®. In clinical studies (both controlled and uncontrolled), 2% of patients experienced lymphocyte counts <$0.5\times10^9$/L for at least six months. In these patients, the majority of lymphocyte counts remained <$0.5\times10^9$/L with continued therapy.

If therapy is continued in presence of severe prolonged lymphopenia, the risk of an opportunistic infection, including PML cannot be ruled out. Therefore patients who experience lymphopenia should be monitored closely for signs and symptoms of appearance of new neurological dysfunction (e.g. motor dysfunction, cognitive or psychiatric symptoms). In case PML is suspected, treatment with TECFIDERA® should be withheld immediately and further evaluations performed.

Prior Treatment with Immunosuppressive or Immunomodulating Therapies

No controlled clinical studies have been performed evaluating the efficacy and safety of TECFIDERA® when switching patients from other disease modifying therapies to TECFIDERA®. The contribution of prior immunosuppressive therapy to the development of PML in TECFIDERA® treated patients is unknown. When switching patients from another disease modifying therapy to TECFIDERA®, the half-life and mode of action of the other therapy must be considered in order to avoid an additive immune effect whilst at the same time minimising the risk of disease reactivation. A complete blood count, including lymphocytes, must be performed prior to initiating TECFIDERA® and regularly during treatment (see blood/laboratory tests above).

TECFIDERA® can generally be started immediately after discontinuation of interferon or glatiramer acetate.

In accordance with good clinical practice an MRI should be considered when switching between disease modifying therapies.

Severe Renal and Hepatic Impairment

TECFIDERA® has not been studied in patients with severe renal or severe hepatic impairment and caution should, therefore, be used in these patients.

Severe Active Gastrointestinal Disease

TECFIDERA® has not been studied in patients with severe active gastrointestinal disease and caution should, therefore, be used in these patients.

Flushing

In clinical trials, 34% of TECFIDERA® treated patients experienced flushing. In the majority of patients who experienced flushing, it was mild or moderate in severity.

In clinical trials, 3 patients out of a total of 2,560 patients treated with TECFIDERA® experienced serious flushing symptoms that were probable hypersensitivity or anaphylactoid reactions. These events were not life-threatening, but led to hospitalisation.

Prescribers and patients should be alert to this possibility in the event of severe flushing reactions.

Infections

In phase III placebo-controlled studies, the incidence of infections (60% vs 58%) and serious infections (2% vs 2%) was similar in patients treated with TECFIDERA® or placebo, respectively. There was no increased incidence of serious infections observed in patients with lymphocyte counts <$0.8\times10^9$/L or <$0.5\times10^9$/L. During treatment with TECFIDERA® in the MS placebo controlled trials, mean lymphocyte counts decreased by approximately 30% from baseline at one year and then plateaued. Mean lymphocyte counts remained within normal limits. Patients with lymphocyte counts <$0.5\times10^9$/L were observed in <1% of patients treated with placebo and 6% of patients treated with TECFIDERA®. In clinical studies (both controlled and uncontrolled), 2% of patients experienced lymphocyte counts <$0.5\times10^9$/L for at least six months.

In these patients, the majority of lymphocyte counts remained <$0.5\times10^9$/L with continued therapy.

If therapy is continued in presence of severe prolonged lymphopenia, the risk of an opportunistic infection, including Progressive Multifocal Leukoencephalopathy (PML) cannot be ruled out (please refer to subsection PML above for further details).

If a patient develops a serious infection, suspending treatment with TECFIDERA® should be considered and the benefits and risks should be reassessed prior to re-initiation of therapy. Patients receiving TECFIDERA® should be instructed to report symptoms of infections to a physician. Patients with serious infections should not start treatment with TECFIDERA® until the infection(s) is resolved.

6.10 Example 10: Instructing the Patient—Package Leaflet

By way of example, but not limitation, instructions for TECFIDERA® use in a Package Leaflet can be as follows:

Warnings and Precautions

TECFIDERA® may affect your white blood cell counts, your kidneys and liver. Before you start TECFIDERA®, your doctor will do a blood test to count the number of your white blood cells and will check that your kidneys and liver are working properly. Your doctor will test these periodically during treatment. If your number of white blood cells decreases during treatment, your doctor may consider stopping your treatment.

7. INCORPORATION BY REFERENCE

Various references such as patents, patent applications, and publications are cited herein, the disclosures of which are hereby incorporated by reference herein in their entireties.

What is claimed is:

1. A method of treating multiple sclerosis ("MS") by administering treatment to patients for which a complete blood count including lymphocyte count has been obtained, which treatment comprises:

administering a pharmaceutical composition comprising 240 mg dimethyl fumarate ("DMF") twice a day, to an MS patient who has been receiving treatment with DMF for at least 6M, with the provisos that a fumarate salt is not present in the pharmaceutical composition and that no additional fumarate other than DMF is present in the pharmaceutical composition, and wherein the patient:

(i) has had at least one lymphocyte count below $0.5 \times 10^9$/L; and (ii) has not had a lymphocyte count below $0.5 \times 10^9$/L that persists for more than 6M.

2. The method of claim 1, wherein the administering is done orally.

3. The method of claim 1, wherein the administering is not greater than 480 mg daily total DMF.

4. The method of claim 1, further comprising monitoring the MS patient for a sign or symptom suggestive of progressive multifocal leukoencephalopathy ("PML").

5. The method of claim 4, wherein the sign or symptom suggestive of PML is selected from the group consisting of progressive weakness on one side of the body or clumsiness of limbs, disturbance of vision, and changes in thinking, memory, and orientation leading to confusion and personality changes.

6. A method of treating multiple sclerosis ("MS") by administering treatment to patients for which a complete blood count including lymphocyte count has been obtained, which treatment comprises:

administering a pharmaceutical composition comprising fumarate to an MS patient who has been receiving treatment with the pharmaceutical composition for at least 6M, wherein said fumarate is dimethyl fumarate ("DMF"), monomethyl fumarate ("MMF"), or a combination of DMF and MMF, with the provisos that a fumarate salt is not present in the pharmaceutical composition and that no additional fumarate other than DMF or MMF is present in the pharmaceutical composition, and wherein the patient:

(i) has had at least one lymphocyte count below $0.5 \times 10^9$/L; and (ii) has not had a lymphocyte count below $0.5 \times 10^9$/L that persists for more than 6M.

7. The method of claim 6, wherein the fumarate is DMF.

8. The method of claim 6, wherein the fumarate is DMF and MMF.

9. The method of claim 6, wherein the fumarate is MMF.

10. The method of claim 6, wherein the administering is done orally.

11. The method of claim 6, wherein the administering is of 240 mg DMF twice daily orally.

12. The method of claim 6, wherein the administering is of 120 mg DMF twice daily orally for 7 days, followed by 240 mg DMF twice daily orally as a maintenance dose.

13. The method of claim 6, wherein the administering is not greater than 720 mg daily total fumarates.

14. The method of claim 6, wherein the administering is not greater than 480 mg daily total fumarates.

15. The method of claim 6, further comprising monitoring the MS patient for a sign or symptom suggestive of progressive multifocal leukoencephalopathy ("PML").

16. The method of claim 15, wherein the sign or symptom suggestive of PML is selected from the group consisting of progressive weakness on one side of the body or clumsiness of limbs, disturbance of vision, and changes in thinking, memory, and orientation leading to confusion and personality changes.

* * * * *